United States Patent
Ban et al.

(10) Patent No.: US 12,421,272 B2
(45) Date of Patent: Sep. 23, 2025

(54) ARTIFICIAL NUCLEIC ACID, PRODUCTION METHOD THEREFOR, AND USE THEREOF

(71) Applicant: SYSMEX CORPORATION, Kobe (JP)

(72) Inventors: Ikuya Ban, Ibaraki (JP); Haruhisa Yoshikawa, Ibaraki (JP); Ayako Orita, Ibaraki (JP); Takeshi Imanishi, Ibaraki (JP)

(73) Assignee: SYSMEX CORPORATION, Kobe (JP)

( * ) Notice: Subject to any disclaimer, the term of this patent is extended or adjusted under 35 U.S.C. 154(b) by 968 days.

(21) Appl. No.: 17/487,906

(22) Filed: Sep. 28, 2021

(65) Prior Publication Data

US 2022/0089634 A1 Mar. 24, 2022

Related U.S. Application Data

(63) Continuation-in-part of application No. PCT/JP2020/014332, filed on Mar. 27, 2020.

(30) Foreign Application Priority Data

Mar. 29, 2019 (JP) .................. 2019-067564

(51) Int. Cl.
| | | |
|---|---|---|
| C07H 19/06 | (2006.01) | |
| C07H 1/00 | (2006.01) | |
| C07H 19/16 | (2006.01) | |
| C07H 21/00 | (2006.01) | |
| C12Q 1/68 | (2018.01) | |
| C12Q 1/6844 | (2018.01) | |

(52) U.S. Cl.
CPC .............. *C07H 19/06* (2013.01); *C07H 1/00* (2013.01); *C07H 19/16* (2013.01); *C07H 21/00* (2013.01); *C12Q 1/6844* (2013.01)

(58) Field of Classification Search
CPC .......... C07H 19/06; C07H 1/00; C07H 19/16; C07H 21/00; C07H 19/00; C12Q 1/6844
See application file for complete search history.

(56) References Cited

U.S. PATENT DOCUMENTS

| | | |
|---|---|---|
| 5,130,238 A | 7/1992 | Malek et al. |
| 5,359,067 A | 10/1994 | Jähne |
| 5,399,491 A | 3/1995 | Kacian et al. |
| 5,455,166 A | 10/1995 | Walker |
| 6,410,278 B1 | 6/2002 | Notomi et al. |
| 2001/0053518 A1 | 12/2001 | Ishiguro et al. |
| 2003/0073081 A1 | 4/2003 | Mukai et al. |
| 2003/0105309 A1 | 6/2003 | Imanishi et al. |
| 2003/0207841 A1 | 11/2003 | Kaneko et al. |
| 2006/0166908 A1 | 7/2006 | Imanishi et al. |
| 2007/0167387 A1 | 7/2007 | Imanishi et al. |
| 2012/0071646 A1 | 3/2012 | Umemoto et al. |
| 2012/0208991 A1 | 8/2012 | Obika et al. |
| 2015/0240299 A1 | 8/2015 | Imanishi et al. |
| 2015/0266917 A1 | 9/2015 | Obika et al. |
| 2016/0010090 A1 | 1/2016 | Vagle |
| 2017/0044528 A1 | 2/2017 | Obika et al. |
| 2018/0223281 A1 | 8/2018 | Iba et al. |

FOREIGN PATENT DOCUMENTS

| | | |
|---|---|---|
| EP | 0 320 308 A2 | 6/1989 |
| JP | 2016-518826 A | 6/2016 |
| WO | 2017/047097 A1 | 3/2017 |

OTHER PUBLICATIONS

Extended European Search Report dated Nov. 28, 2022 in European Application No. 20782720.5.
First Office Action issued Sep. 26, 2023 for CN Application No. 202080023927.0.
Notice of Reasons for Refusal issued Oct. 24, 2023 for JP Application No. 2021-512077.
International Search Report issued May 26, 2020 in International Application No. PCT/JP2020/014332.
Written Opinion of the International Searching Authority issued May 26, 2020 in International Application No. PCT/JP2020/014332.

(Continued)

*Primary Examiner* — Jezia Riley
(74) *Attorney, Agent, or Firm* — Sughrue Mion, PLLC

(57) ABSTRACT

Disclosed is a compound represented by formula (1) or a salt thereof:

[Formula 1]

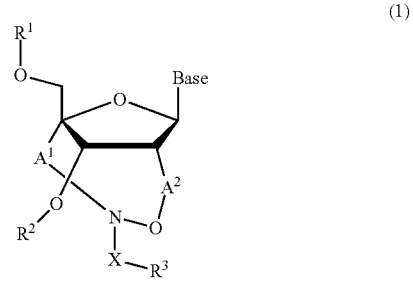

(wherein:
"Base" represents an aromatic heterocyclic group which may have a substituent or an aromatic hydrocarbon ring group which may have a substituent;
$A^1$ represents a linear alkylene group;
$A^2$ represents a single bond or an alkylene group;
X represents an alkylene group, —O— or —S(=O)$_k$—;
$R^1$ and $R^2$ are the same as or different from each other and independently represent a hydrogen atom, etc.; and
$R^3$ represents an amino group which may have a substituent).

14 Claims, 13 Drawing Sheets

Specification includes a Sequence Listing.

(56) References Cited

OTHER PUBLICATIONS

Rahman et al., "Design, Synthesis, and Properties of 2',4'-BNA$^{NC}$: A Bridged Nucleic Acid Analogue", Journal of American Chemical Society, 2008, vol. 130, No. 14, pp. 4886-4896 (11 pages total).

Nielsen, "Peptide Nucleic Acid. A Molecule with Two Identities", Accounts of Chemical Research, 1999, vol. 32, No. 7, pp. 624-630 (7 pages total).

Osawa et al., "Synthesis and properties of oligonucleotides bearing thymidine derivatives with 1,6-dioxaspiro[4.5]decane skeleton", Bioorganic & Medicinal Chemistry, 2021, vol. 31, No. 115966, pp. 1-8 (8 pages total).

Maity et al., "Introduction of Vinyl and Hydroxymethyl Functionalities at C-4 of Glucose-Derived Substrates: Synthesis of Spirocyclic, Bicyclic, and Tricyclic Nucleotides", Journal of Organic Chemistry, 2008, vol. 73, No. 11, pp. 4305-4308 (4 pages total).

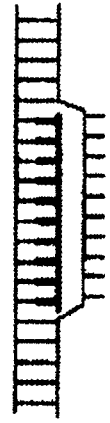
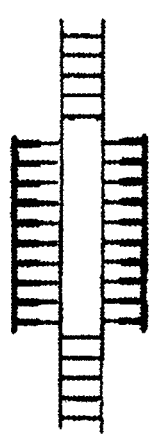
FIG. 1A TRIPLE HELIX (ANTI-GENE METHOD)
FIG. 1B TRIPLE HELIX INVASION
FIG. 1C DOUBLE HELIX INVASION (STRAND INVASION METHOD)
FIG. 1D TWO DOUBLE HELIX INVASIONS FIG. 3A WITHOUT CLAMP
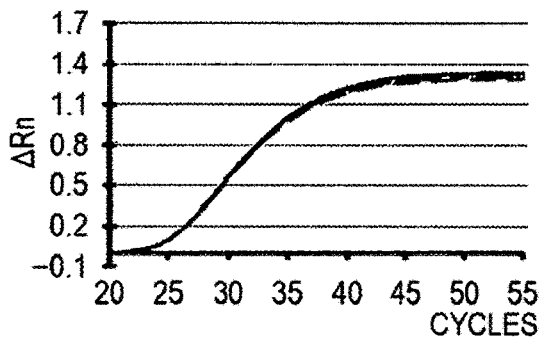
FIG. 3B CLAMP NUCLEIC ACID 1 (AMOUNT USED: 10pmol)
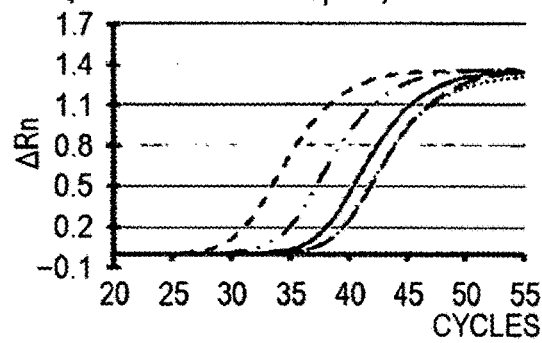
FIG. 3C CLAMP NUCLEIC ACID 2 (AMOUNT USED: 10pmol)
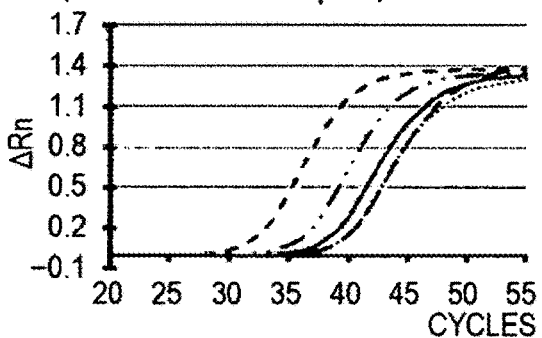
CLAMP NUCLEIC ACID 3 (AMOUNT USED: 10pmol)
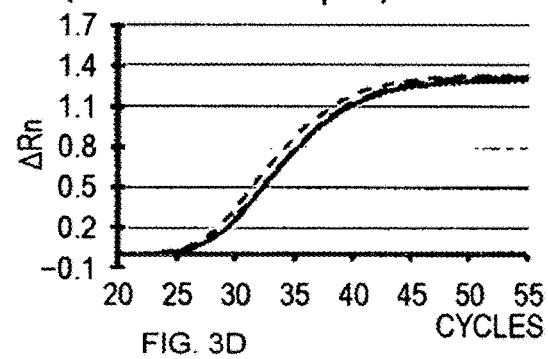
FIG. 3D
FIG. 3E CLAMP NUCLEIC ACID 4 (AMOUNT USED: 10pmol)
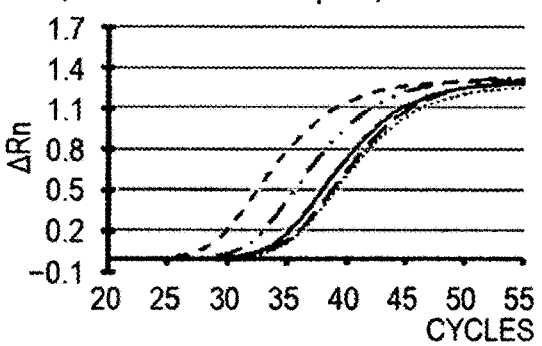
FIG. 3F
| M(M+W) | 10% | 1% | 0.10% | 0.01% | 0% |
|---|---|---|---|---|---|
| LINE | - - - | -·-·- | —— | — — | ······ |

FIG. 3G CLAMP NUCLEIC ACID 1 (AMOUNT USED: 1pmol)
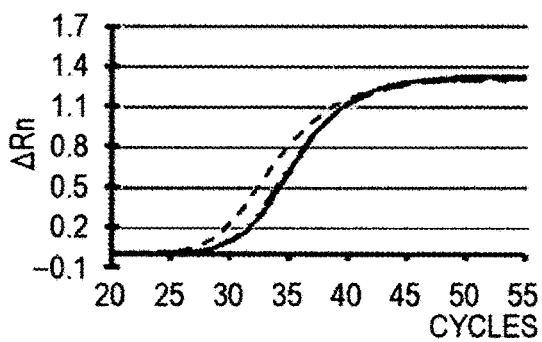
FIG. 3H CLAMP NUCLEIC ACID 2 (AMOUNT USED: 1pmol)
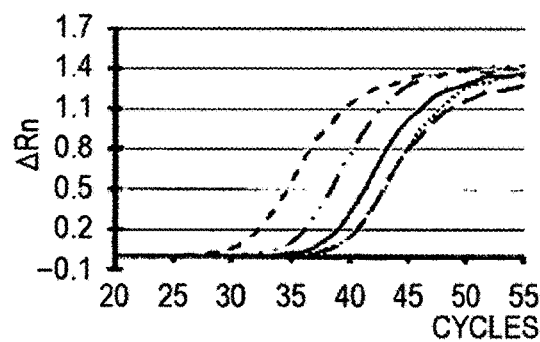
FIG. 3I
| M(M+W) | 10% | 1% | 0.10% | 0.01% | 0% |
|---|---|---|---|---|---|
| LINE | – – – | – · – · | —— | — — | ·········· |

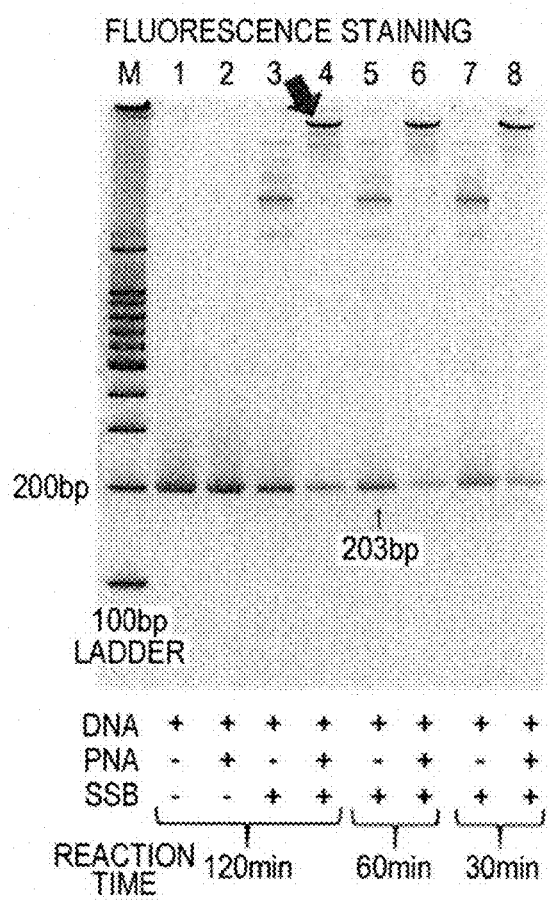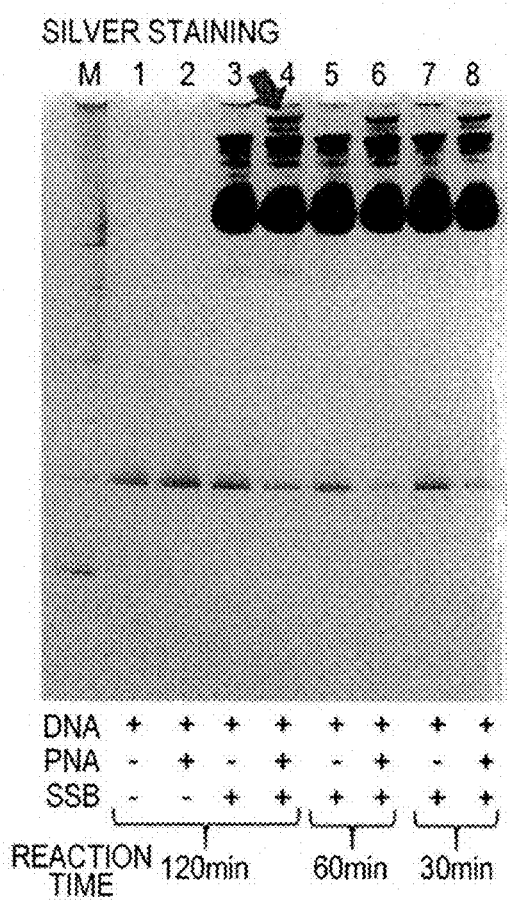

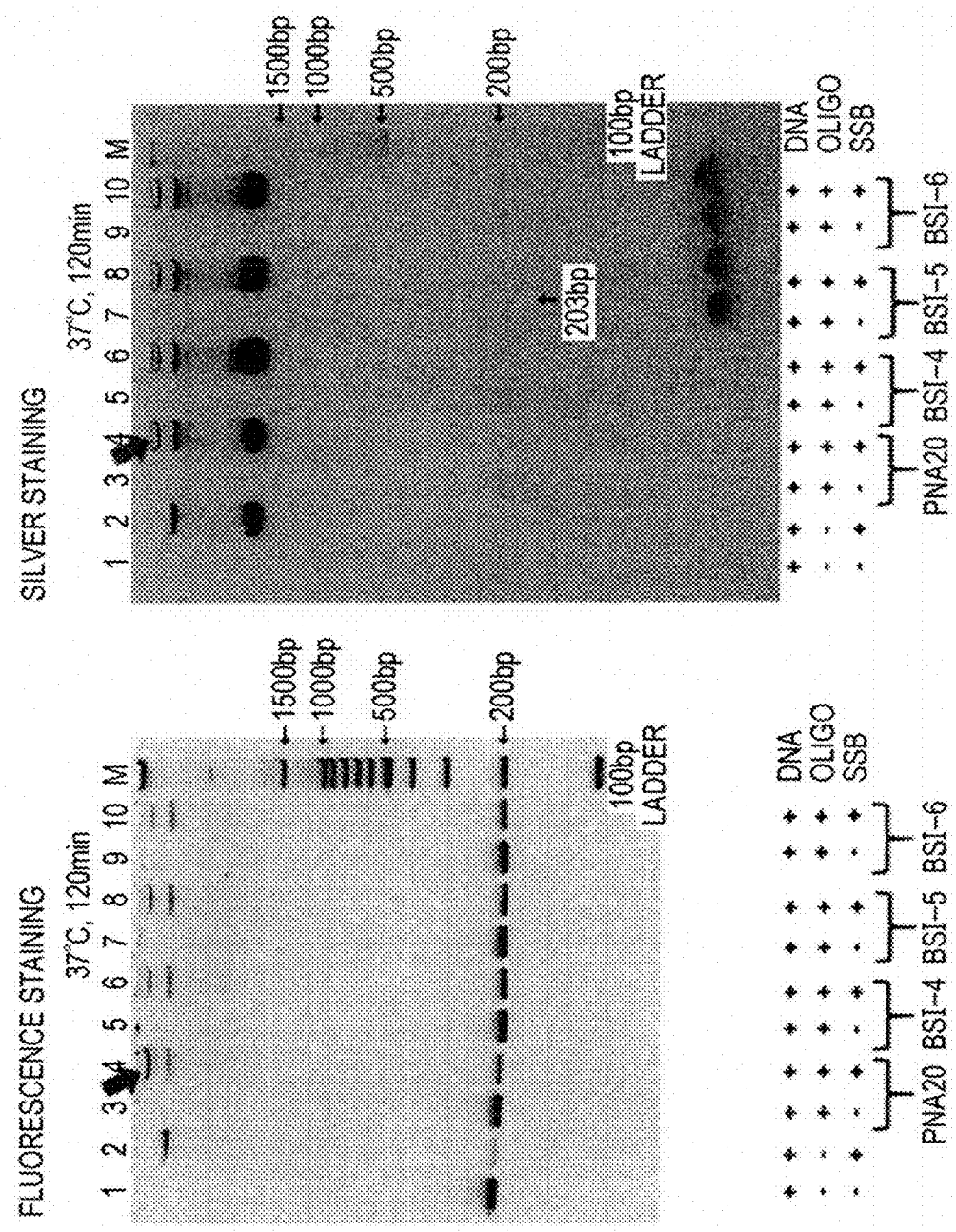

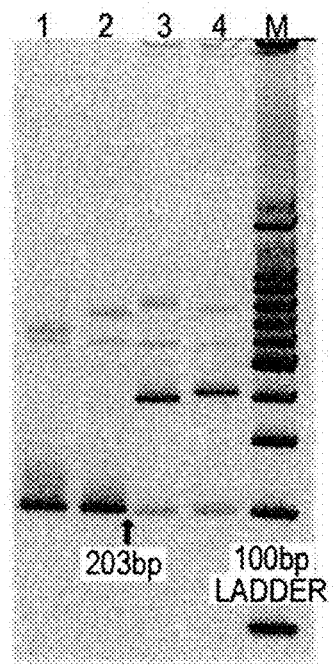
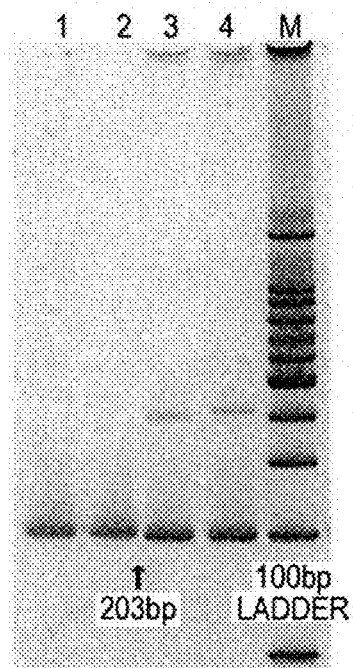
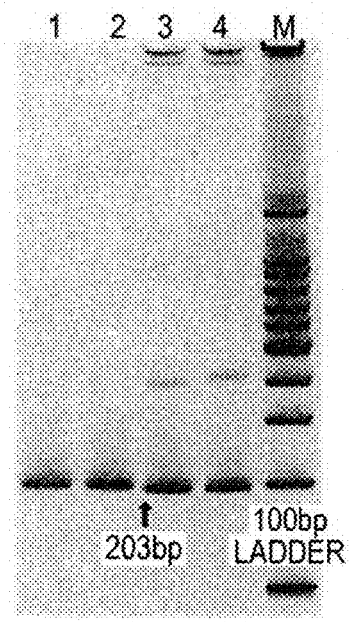
FIG. 6A  
FIG. 6B  
FIG. 6C

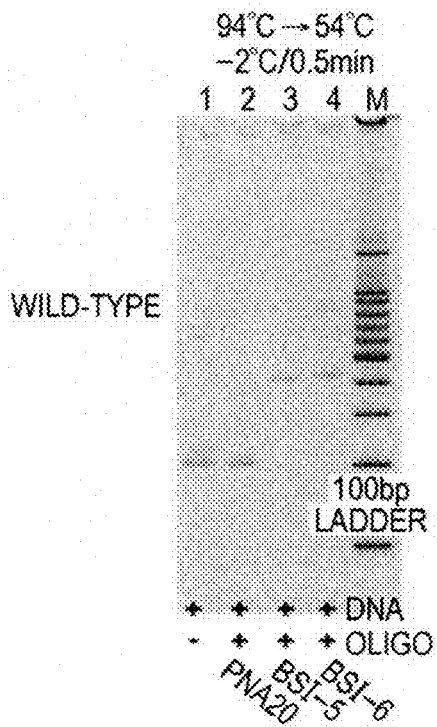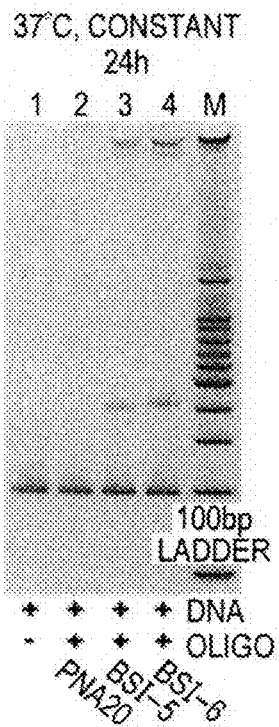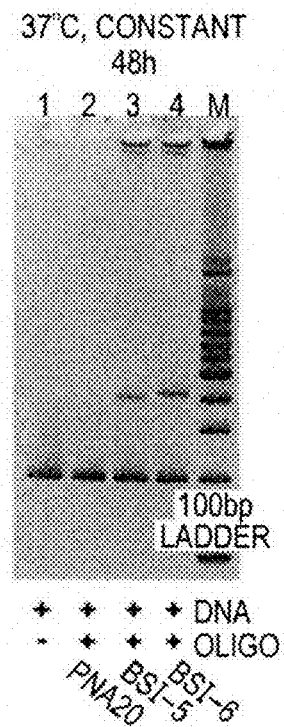

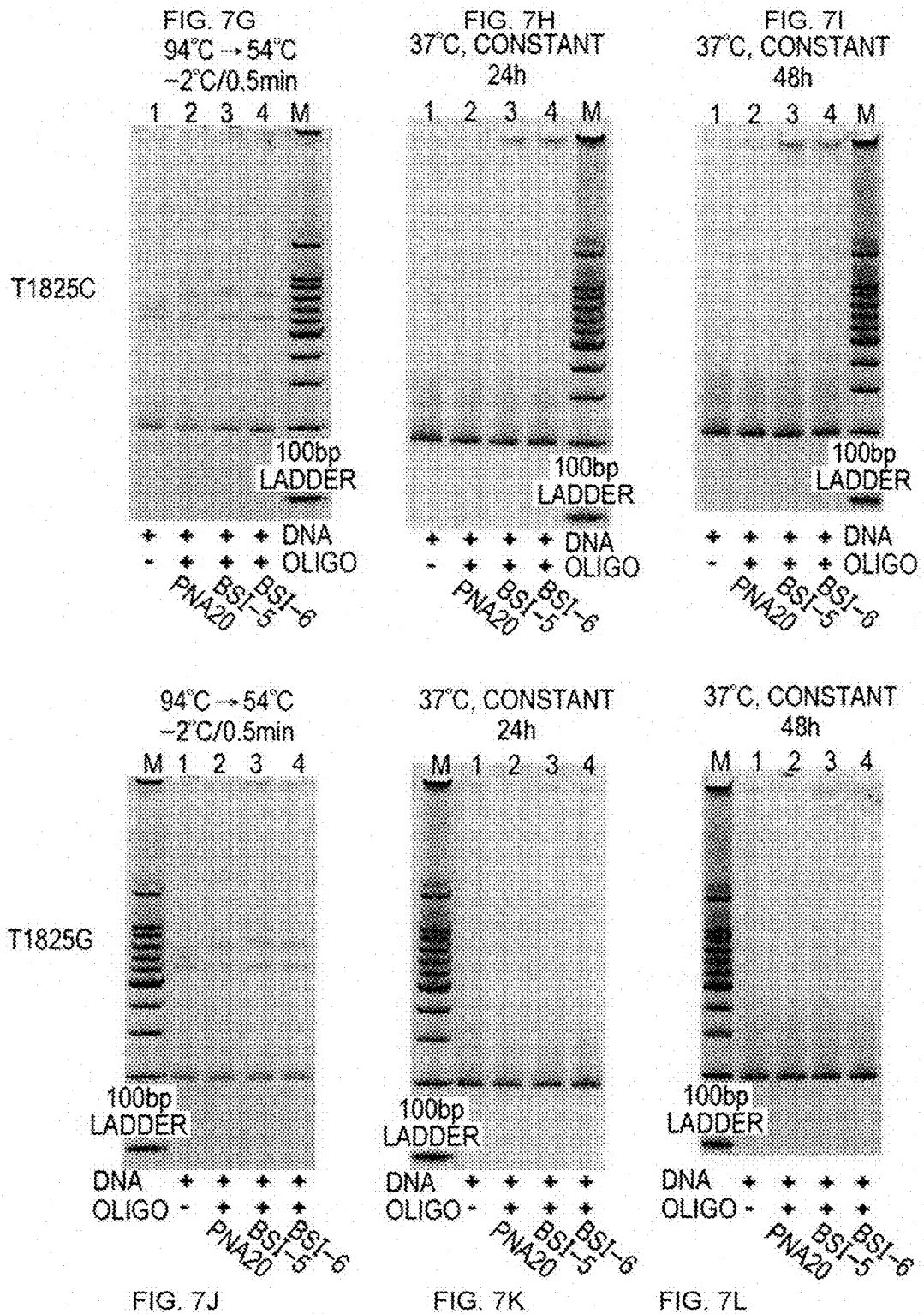

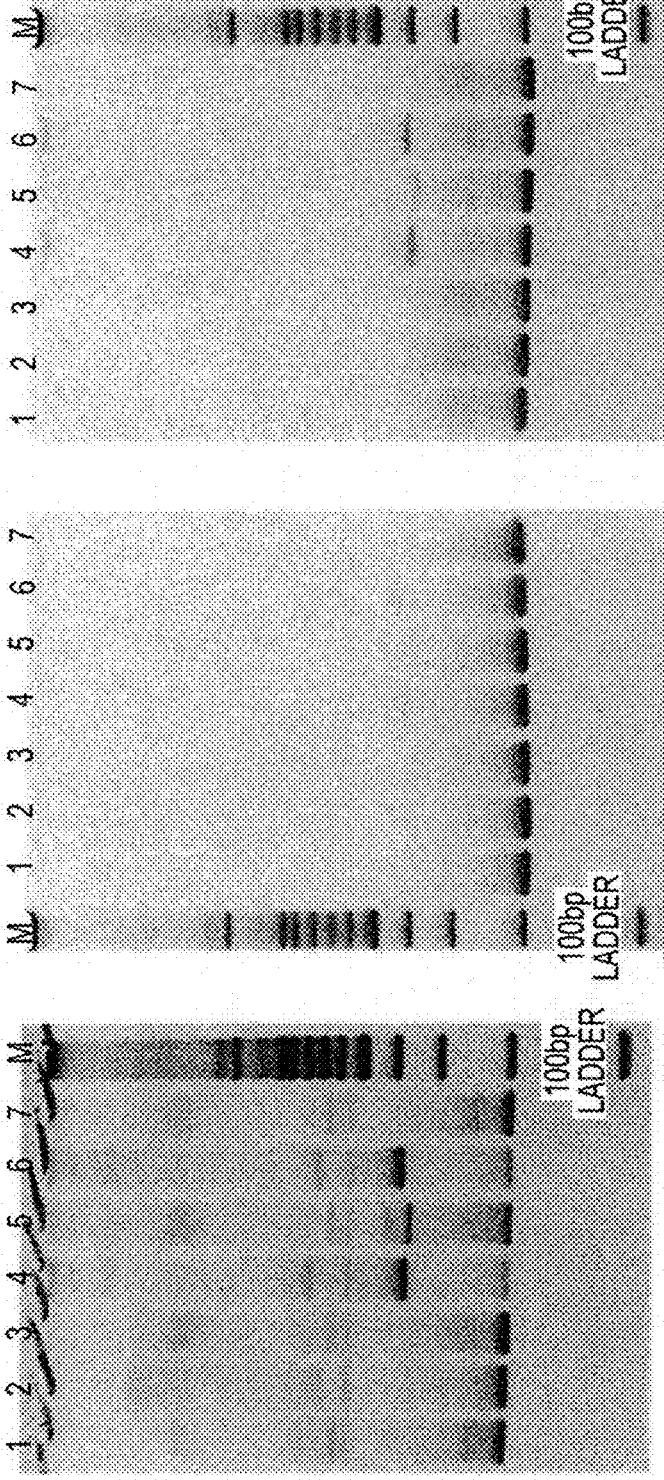
FIG. 8A 94°C→54°C −2°C/0.5min
FIG. 8B 37°C, CONSTANT 2h
FIG. 8C 37°C, CONSTANT 24h

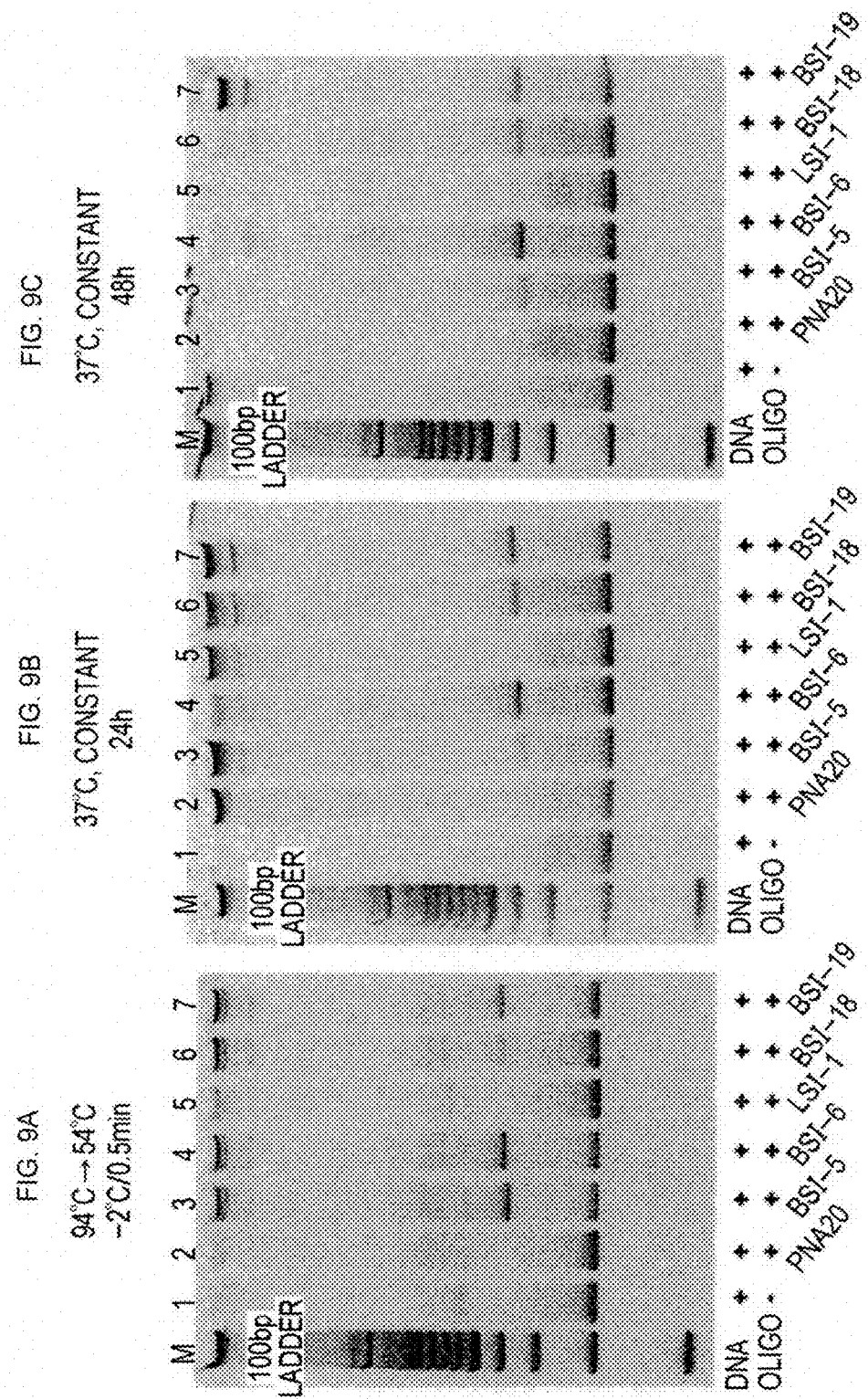

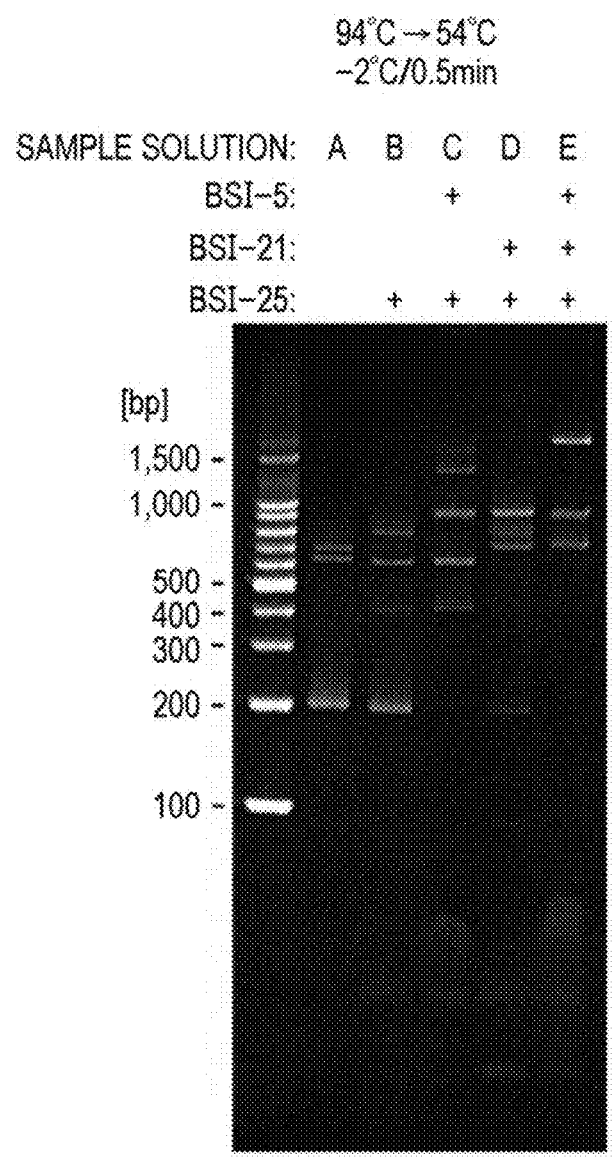

SEQUENCE LISTING

<160> NUMBER OF SEQ ID NOS: 26

<210> SEQ ID NO 1
<211> LENGTH: 12
<212> TYPE: DNA
<213> ORGANISM: Artificial Sequence
<220> FEATURE:
<223> OTHER INFORMATION: Synthetic antisense sequence
<220> FEATURE:
<221> NAME/KEY: modified_base
<222> LOCATION: (6)..(6)
<223> OTHER INFORMATION: n is modified t
<220> FEATURE:
<221> NAME/KEY: misc_feature
<222> LOCATION: (6)..(6)
<223> OTHER INFORMATION: n is a, c, g, or t

<400> SEQUENCE: 1
gcgttntttg ct                                                          12

<210> SEQ ID NO 2
<211> LENGTH: 12
<212> TYPE: DNA
<213> ORGANISM: Artificial Sequence
<220> FEATURE:
<223> OTHER INFORMATION: Synthetic antisense sequence
<220> FEATURE:
<221> NAME/KEY: modified_base
<222> LOCATION: (4)..(4)
<223> OTHER INFORMATION: n is modified t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (6)..(6)

```
<223> OTHER INFORMATION: n is modified t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(8)
<223> OTHER INFORMATION: n is modified t
<220> FEATURE:
<221> NAME/KEY: misc_feature
<222> LOCATION: (8)..(8)
<223> OTHER INFORMATION: n is a, c, g, or t

<400> SEQUENCE: 2
gcgntntntg ct                                                              12

<210> SEQ ID NO 3
<211> LENGTH: 12
<212> TYPE: DNA
<213> ORGANISM: Artificial Sequence
<220> FEATURE:
<223> OTHER INFORMATION: Synthetic antisense sequence
<220> FEATURE:
<221> NAME/KEY: modified_base
<222> LOCATION: (4)..(9)
<223> OTHER INFORMATION: n is modified t
<220> FEATURE:
<221> NAME/KEY: misc_feature
<222> LOCATION: (4)..(9)
<223> OTHER INFORMATION: n is a, c, g, or t

<400> SEQUENCE: 3
gcgnnnnnng ct                                                              12

<210> SEQ ID NO 4
<211> LENGTH: 10
<212> TYPE: DNA
<213> ORGANISM: Artificial Sequence
<220> FEATURE:
<223> OTHER INFORMATION: Synthetic antisense sequence
<220> FEATURE:
<221> NAME/KEY: modified_base
<222> LOCATION: (9)..(9)
<223> OTHER INFORMATION: n is modified t
<220> FEATURE:
<221> NAME/KEY: misc_feature
<222> LOCATION: (9)..(9)
<223> OTHER INFORMATION: n is a, c, g, or t

<400> SEQUENCE: 4 tttttttnt                                                                  10

<210> SEQ ID NO 5
<211> LENGTH: 12
<212> TYPE: DNA
<213> ORGANISM: Artificial Sequence
<220> FEATURE:
<223> OTHER INFORMATION: Synthetic antisense sequence

<400> SEQUENCE: 5 gcgtttttg ct                                                               12

<210> SEQ ID NO 6
<211> LENGTH: 12
<212> TYPE: DNA
<213> ORGANISM: Artificial Sequence
<220> FEATURE:
<223> OTHER INFORMATION: Synthetic sense sequence

<400> SEQUENCE: 6
```

-continued agcaaaaaac gc                                                    12

<210> SEQ ID NO 7
<211> LENGTH: 12
<212> TYPE: RNA
<213> ORGANISM: Artificial Sequence
<220> FEATURE:
<223> OTHER INFORMATION: Synthetic sense sequence

<400> SEQUENCE: 7
agcaaaaaac gc                                                    12

<210> SEQ ID NO 8
<211> LENGTH: 10
<212> TYPE: DNA
<213> ORGANISM: Artificial Sequence
<220> FEATURE:
<223> OTHER INFORMATION: Synthetic oligonucleotide sequence

<400> SEQUENCE: 8
tttttttttt                                                       10

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide sequence, forward
      primer

<400> SEQUENCE: 9
actgaatata aacttgtggt ag                                         22

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide sequence, reverse
      primer

<400> SEQUENCE: 10
attgttggat catattcgtc                                            20

<210> SEQ ID NO 11
<211> LENGTH: 28
<212> TYPE: DNA
<213> ORGANISM: Artificial Sequence
<220> FEATURE:
<223> OTHER INFORMATION: Synthetic oligonucleotide probe sequence

<400> SEQUENCE: 11
cttgacgata cagctaattc agaatcat                                   28

<210> SEQ ID NO 12
<211> LENGTH: 18
<212> TYPE: DNA
<213> ORGANISM: Artificial Sequence
<220> FEATURE:
<223> OTHER INFORMATION: Synthetic sequence, clamp nucleic acid
<220> FEATURE:
<221> NAME/KEY: modified_base
<222> LOCATION: (1)..(1)
<223> OTHER INFORMATION: n is modified g
<220> FEATURE:
<221> NAME/KEY: misc_feature
<222> LOCATION: (1)..(1)

```
<223> OTHER INFORMATION: n is a, c, g, or t
<220> FEATURE:
<221> NAME/KEY: modified_base
<222> LOCATION: (4)..(4)
<223> OTHER INFORMATION: n is modified t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: modified_base
<222> LOCATION: (6)..(6)
<223> OTHER INFORMATION: n is modified c
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (8)..(9)
<223> OTHER INFORMATION: n is modified c
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: modified_base
<222> LOCATION: (11)..(12)
<223> OTHER INFORMATION: n is modified c
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: modified_base
<222> LOCATION: (15)..(15)
<223> OTHER INFORMATION: n is modified c
<220> FEATURE:
<221> NAME/KEY: misc_feature
<222> LOCATION: (15)..(15)
<223> OTHER INFORMATION: n is a, c, g, or t

<400> SEQUENCE: 12
nccnangnna nnagntcc                                                 18

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: modified_base
<222> LOCATION: (1)..(5)
<223> OTHER INFORMATION: n is modified a, c, g, or t
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: modified_base
<222> LOCATION: (7)..(12)
<223> OTHER INFORMATION: n is modified a, c, or t
<220> FEATURE:
<221> NAME/KEY: misc_feature
<222> LOCATION: (7)..(12)
<223> OTHER INFORMATION: n is a, c, g, or t
<220> FEATURE:
<221> NAME/KEY: modified_base
<222> LOCATION: (14)..(19)
<223> OTHER INFORMATION: n is modified a, c, g, or t
<220> FEATURE:
<221> NAME/KEY: misc_feature
<222> LOCATION: (14)..(19)
<223> OTHER INFORMATION: n is a, c, g, or t

<400> SEQUENCE: 13
```
nnnnngnnnn nnannnnnna                               20

<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: modified_base
<222> LOCATION: (1)..(3)
<223> OTHER INFORMATION: n is modified a, c, or t
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: modified_base
<222> LOCATION: (5)..(6)
<223> OTHER INFORMATION: n is modified t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: modified_base
<222> LOCATION: (8)..(14)
<223> OTHER INFORMATION: n is modified a, c, or t
<220> FEATURE:
<221> NAME/KEY: misc_feature
<222> LOCATION: (8)..(14)
<223> OTHER INFORMATION: n is a, c, g, or t
<220> FEATURE:
<221> NAME/KEY: modified_base
<222> LOCATION: (16)..(16)
<223> OTHER INFORMATION: n is modified t
<220> FEATURE:
<221> NAME/KEY: misc_feature
<222> LOCATION: (16)..(16)
<223> OTHER INFORMATION: n is a, c, g, or t

<400> SEQUENCE: 14
nnngnncnnn nnnngn                                   16

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence, wild-type

<400> SEQUENCE: 15
ggcatgttca tcatcagtaa                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic sequence, wild type

<400> SEQUENCE: 16
ttactgatga tgaacatgcc                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence, T1825G

<400> SEQUENCE: 17
ggcatgttca gcatcagtaa    20

<210> SEQ ID NO 18
<211> LENGTH: 20
<212> TYPE: DNA
<213> ORGANISM: Artificial Sequence
<220> FEATURE:
<223> OTHER INFORMATION: Synthetic sequence, T1825G

<400> SEQUENCE: 18
ttactgatgc tgaacatgcc    20

<210> SEQ ID NO 19
<211> LENGTH: 20
<212> TYPE: DNA
<213> ORGANISM: Artificial Sequence
<220> FEATURE:
<223> OTHER INFORMATION: Synthetic sequence, T1825C

<400> SEQUENCE: 19
ggcatgttca ccatcagtaa    20

<210> SEQ ID NO 20
<211> LENGTH: 20
<212> TYPE: DNA
<213> ORGANISM: Artificial Sequence
<220> FEATURE:
<223> OTHER INFORMATION: Synthetic sequence, T1825C

<400> SEQUENCE: 20
ttactgatgg tgaacatgcc    20

<210> SEQ ID NO 21
<211> LENGTH: 20
<212> TYPE: DNA
<213> ORGANISM: Artificial Sequence
<220> FEATURE:
<223> OTHER INFORMATION: Synthetic sequence, T1825A

<400> SEQUENCE: 21
ggcatgttca acatcagtaa    20

<210> SEQ ID NO 22
<211> LENGTH: 20
<212> TYPE: DNA
<213> ORGANISM: Artificial Sequence
<220> FEATURE:
<223> OTHER INFORMATION: Synthetic sequence, T1825A

<400> SEQUENCE: 22
ttactgatgt tgaacatgcc    20

<210> SEQ ID NO 23
<211> LENGTH: 203
<212> TYPE: DNA
<213> ORGANISM: Artificial Sequence
<220> FEATURE:
<223> OTHER INFORMATION: Synthetic sequence, pBR322 plasmid

<400> SEQUENCE: 23
cgaagcgctg gcattgaccc tgagtgattt ttctctggtc ccgccgcatc cataccgcca    60
gttgtttacc ctcacaacgt tccagtaacc gggcatgttc atcatcagta acccgtatcg   120
tgagcatcct ctctcgtttc atcggtatca ttaccccat gaacagaaat cccccttaca   180
cggaggcatc agtgaccaaa cag                                              203

<210> SEQ ID NO 24
<211> LENGTH: 203
<212> TYPE: DNA
<213> ORGANISM: Artificial Sequence
<220> FEATURE:
<223> OTHER INFORMATION: Synthetic sequence, pBR322 plasmid

<400> SEQUENCE: 24
ctgtttggtc actgatgcct ccgtgtaagg gggatttctg ttcatggggg taatgatacc        60
gatgaaacga gagaggatgc tcacgatacg ggttactgat gatgaacatg cccggttact       120
ggaacgttgt gagggtaaac aactggcggt atggatgcgg cgggaccaga gaaaaatcac       180
tcagggtcaa tgccagcgct tcg                                              203

<210> SEQ ID NO 25
<211> LENGTH: 15
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: modified_base
<222> LOCATION: (1)..(2)
<223> OTHER INFORMATION: n is modified a or c
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: modified_base
<222> LOCATION: (4)..(7)
<223> OTHER INFORMATION: n is modified a, c, or t
<220> FEATURE:
<221> NAME/KEY: misc_feature
<222> LOCATION: (4)..(7)
<223> OTHER INFORMATION: n is a, c, g, or t
<220> FEATURE:
<221> NAME/KEY: modified_base
<222> LOCATION: (9)..(9)
<223> OTHER INFORMATION: n is modified g
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (11)..(15)
<223> OTHER INFORMATION: n is modified a, c, or t
<220> FEATURE:
<221> NAME/KEY: misc_feature
<222> LOCATION: (11)..(15)
<223> OTHER INFORMATION: n is a, c, g, or t

<400> SEQUENCE: 25
nngnnnngng nnnnn                                                        15

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: modified_base
<222> LOCATION: (1)..(5)
<223> OTHER INFORMATION: n is modified a, c, g, or t
<220> FEATURE:
<221> NAME/KEY: misc_feature
<222> LOCATION: (1)..(5)

```
<223> OTHER INFORMATION: n is a, c, g, or t
<220> FEATURE:
<221> NAME/KEY: modified_base
<222> LOCATION: (7)..(10)
<223> OTHER INFORMATION: n is modified a, c, or t
<220> FEATURE:
<221> NAME/KEY: misc_feature
<222> LOCATION: (7)..(10)
<223> OTHER INFORMATION: n is a, c, g, or t
<220> FEATURE:
<221> NAME/KEY: modified_base
<222> LOCATION: (12)..(17)
<223> OTHER INFORMATION: n is modified c or t
<220> FEATURE:
<221> NAME/KEY: misc_feature
<222> LOCATION: (12)..(17)
<223> OTHER INFORMATION: n is a, c, g, or t
<220> FEATURE:
<221> NAME/KEY: modified_base
<222> LOCATION: (19)..(20)
<223> OTHER INFORMATION: n is modified t
<220> FEATURE:
<221> NAME/KEY: misc_feature
<222> LOCATION: (19)..(20)
<223> OTHER INFORMATION: n is a, c, g, or t

<400> SEQUENCE: 26
nnnnngnnnn cnnnnnngnn                                                    20
```

ARTIFICIAL NUCLEIC ACID, PRODUCTION METHOD THEREFOR, AND USE THEREOF

CROSS REFERENCE TO RELATED APPLICATIONS

This is the U.S. national stage of application No. PCT/JP2020/014332, filed on Mar. 27, 2020, and this application claims priority from prior Japanese Patent Application No. 2019-067564, filed on Mar. 29, 2019, entitled "NEW ARTIFICIAL NUCLEIC ACID, PRODUCTION METHOD THEREFOR, AND USE THEREOF", the entire contents of which are incorporated herein by reference.

FIELD OF THE INVENTION

The present invention relates to a novel artificial nucleic acid, a method for producing the artificial nucleic acid, a use of the artificial nucleic acid, and others.

BACKGROUND

An oligonucleotide is a short sequence of naturally occurring DNA, naturally occurring RNA or an artificial nucleic acid. It has been shown that an oligonucleotide can regulate the expression of a gene at various gene transcription or translation levels and can examine the state of the sequence for a gene and is therefore very useful for the treatment or diagnosis of a specific disease.

The technique for the regulation of the expression of a gene and the examination/diagnosis of genetic information is roughly classified into two types depending on the types of targets. The first case is a case where a target is single-stranded RNA or single-stranded DNA such as messenger RNA (mRNA) or micro RNA (miRNA), and the second case is a case where the target is double-stranded genomic DNA.

When the target is single-stranded RNA or single-stranded DNA, the process of the translation of a gene can be inhibited (or the genetic diagnosis can be performed) by an antisense method in which an oligonucleotide binds to the single-stranded RNA or the single-stranded DNA complementary to form a double strand. When the oligonucleotide is a double-stranded RNA molecule, the complementary binding of the oligonucleotide to target mRNA can cause the decomposition of the target mRNA with a "slicer" enzyme in an RISC complex (RNA interference method). In the case of RNA interference method, the oligonucleotide may be an oligonucleotide which is equivalent to endogeneous microRNA that can bind to a 3'-UTR region (a 3'-untranslated region) in target mRNA and can inhibit the translation of the target mRNA as the result of the incomplete complementary (microRNA mimics).

An oligonucleotide can induce the activation of a gene or the increase in transcription of the gene through, for example, the complementary binding of the oligonucleotide to long antisense non-coding RNA or the inhibition of complementary microRNA by the oligonucleotide, and, as a result, can increase the translation of target mRNA in the microRNA (anti microRNA).

When the target is double-stranded genomic DNA, a technique can be employed in which an oligonucleotide can interact with (bind to) the double-stranded genomic DNA to regulate (control) the expression of the gene.

FIGS. 1A-1D are diagrams corresponding to FIG. 5 in Acc. Chem. Res. 1999, 32, pp. 624 to 630, in which the modes of binding of an oligonucleotide to double-stranded genomic DNA are shown. The technique is roughly classified into two types depending on the types of binding modes. One is an anti-gene method in which an oligonucleotide binds to the "outside" of double-stranded genomic DNA through Hoogsteen-type hydrogen bonds or reverse-Hoogsteen-type hydrogen bonds to form a triple strand, whereby the expression of a gene can be regulated (FIG. 1A). The other is a strand invasion method in which an oligonucleotide partially loosens a double strand of genomic DNA, then the oligonucleotide strand-invades into the double strand to re-form Watson-Crick-type hydrogen bonds with a single stranded part of the DNA, whereby the expression of a gene can be regulated (FIGS. 1B-1D).

An oligonucleotide which can be used as a functional material for use in a technique for regulating gene expression or examining/diagnosing genetic information has been required to have properties such as excellent sequence-specific binding affinity for a target nucleic acid, high resistance to degradation enzymes and safety in living bodies. DNA and RNA which are naturally occurring materials have poor resistance to degradation enzymes and insufficient binding affinity, and are therefore unsuitable as functional materials. For these reasons, numerous artificial nucleic acids have been developed so far for the purpose of improving the functionalities of oligonucleotides.

Typical examples of the artificial nucleic acid include a peptide nucleic acid (PNA), a crosslinked nucleic acid, a morpholino nucleic acid (PMO), and a phosophorothioate-type nucleic acid (PS oligo) which has such a structure that one of non-binding oxygen atoms in a phosphoric acid diester moiety in a nucleic acid is substituted by a sulfur atom.

Typical examples of the crosslinked nucleic acid include LNA (Structural formula 1), BNA$^{NC}$ (Structural formula 2) and ENA (Structural formula 3).

[Formula 1]

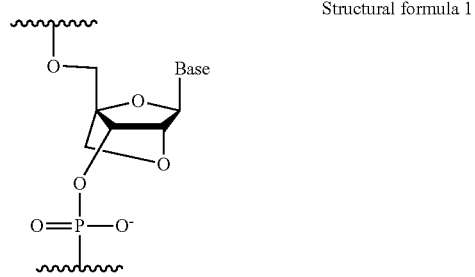

Structural formula 1

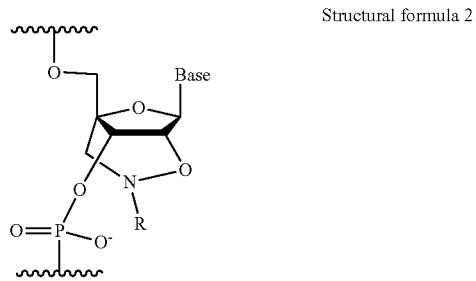

Structural formula 2

R = H, alkyl, aryl, acyl, sulfonyl

3
-continued

Structural formula 3

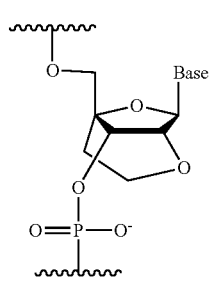

It has been demonstrated that these crosslinked nucleic acids have excellent capability of binding to single-stranded RNA with high sequence selectivity through Watson-Crick-type hydrogen bonds (Patent Documents 1 to 3). As mentioned above, the conventional artificial nucleic acids have been used as functional materials for regulating the expression of a specific gene or for confirming/diagnosing the genetic sequence for the gene with high sensitivity and high accuracy.

However, amid the diversification in use applications of oligonucleotides, there is still a room for improving the functionalities of the already developed artificial nucleic acids and it has been demanded to develop a novel artificial nucleic acid aiming at the further improvement in the functionality of the artificial nucleic acid.

PRIOR ART DOCUMENTS

Patent Document 1: US Patent Application Publication No. 2003/105309

Patent Document 2: US Patent Application Publication No. 2007/167387

Patent Document 3: US Patent Application Publication No. 2003/207841

SUMMARY OF THE INVENTION

The scope of the present invention is defined solely by the appended claims, and is not affected to any degree by the statements within this summary.

An object of the present invention is to provide a novel artificial nucleic acid which is useful in various genome technologies, a method for producing the artificial nucleic acid, a use of the artificial nucleic acid, and others.

The present inventors have studied intensively and extensively in order to achieve the object. As a result, it has been found that an artificial nucleic acid having such a structure that an amino group optionally having a substituent is bound onto a nitrogen atom in BNA$^{NC}$ represented by structural formula 2 through a specific linker has both of highly sequence-selective and stiff bonding capability to single-stranded DNA and excellent resistance capability against digestive enzymes. The present inventors have also found that the artificial nucleic acid is useful in various genome technologies including an antisense method and an anti-gene method (including a strand invasion method). The present inventors have further made studies on the basis of these findings. As a result, the present invention has been accomplished.

4

The present invention includes the following aspects.

Item 1. A compound represented by formula (1) or a salt thereof:

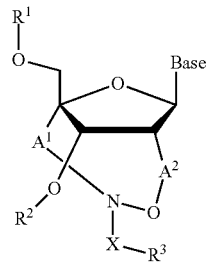

(1)

(wherein:
"Base" represents an aromatic heterocyclic group which may have a substituent or an aromatic hydrocarbon ring group which may have a substituent;
$A^1$ represents a linear alkylene group;
$A^2$ represents a single bond or an alkylene group;
X represents an alkylene group which may have a substituent or a group having such a structure that at least one methylene group moiety in the alkylene group is substituted by —N($R^X$)— (wherein $R^X$ represents a hydrogen atom or an alkyl group), —O— or —S(=O)$_k$— (wherein k represents 0, 1, or 2);
$R^1$ and $R^2$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent, or $R^1$, $R^2$, two oxygen atoms respectively adjacent to $R^1$ and $R^2$ and carbon atoms at position-3 and position-5 in a furanose together form a ring which may have a substituent; and
$R^3$ represents an amino group which may have a substituent).

Item 2. The compound or the salt thereof according to Item 1, wherein $A^1$ represents a methylene group and $A^2$ represents a single bond.

Item 3. The compound or the salt thereof according to Item 1, wherein X represents —$C_nH_{2n}$— (wherein n represents an integer of 1 to 10).

Item 4. The compound or the salt thereof according to Item 1, wherein $R^3$ represents a group represented by formula (A):

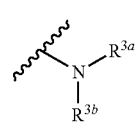

(A)

(wherein $R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and an adjacent nitrogen atom together form a ring which may have a substituent), or a group represented by formula (B):

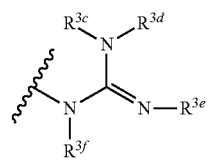

(wherein $R^{3c}$ to $R^{3f}$ are the same as or different from each other and independently represent a hydrogen atom, an alkyl group, or a protecting group for an amino group).

Item 5. The compound or the salt thereof according to Item 4, wherein, in formula (A), $R^{3a}$ and $R^{3b}$ are the same as or different from each other and independently represent a hydrogen atom, an alkyl group, an aryl group, an aralkyl group, or a protecting group for an amino group, or $R^{3a}$, $R^{3b}$ and an adjacent nitrogen atom together form a 5- to 10-membered nitrogenated aliphatic heterocyclic ring which may have an alkyl group as a substituent, and, in formula (B), $R^{3c}$ to $R^{3f}$ are the same as or different from each other and independently represent a hydrogen atom, or a protecting group for an amino group.

Item 6. The compound or the salt thereof according to Item 1, wherein
$R^1$ and $R^2$ are the same as or different from each other and independently represent a hydrogen atom, an alkyl group which may have an alkoxy group as an substituent, an aryl group which may have an alkoxy group as a substituent, an aralkyl group which may have an alkoxy group as a substituent, an alkylcarbonyl group, an arylcarbonyl group, an alkylsulfonyl group, an arylsulfonyl group, a group represented by the formula: $-Si(R^4)_3$ (wherein $R^4$s are the same as or different from each other and independently represent an alkyl group or an aryl group), a group represented by the formula: $-P(R^5)(R^6)$ (wherein $R^5$ and $R^6$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group), a dihydroxyphosphinyl group, or a hydroxymercaptophosphinyl group, or
$R^1$, $R^2$, two oxygen atoms respectively adjacent to $R^1$ and $R^2$ and carbon atoms at position-3 and position-5 in a furanose together form a 6- to 10-membered aliphatic heterocyclic ring which may have an alkyl group as a substituent.

Item 7. The compound or the salt thereof according to Item 1, wherein "Base" represents a 2,4-dioxo-1,2,3,4-tetrahydropyrimidin-1-yl group which may have a substituent, a 2-oxo-1,2-dihydropyrimidin-1-yl group which may have a substituent, a purin-9-yl group which may have a substituent, or a 6-oxo-1,6-dihydro-9H-purin-9-yl group which may have a substituent.

Item 8. The compound or the salt thereof according to Item 1, wherein the compound is represented by any one of formulae (1A) to (1C):

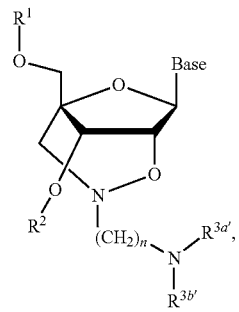

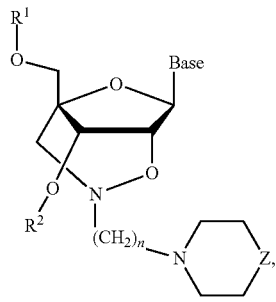

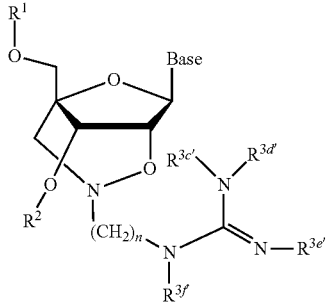

[wherein:
$R^{3a'}$ and $R^{3b'}$ are the same as or different from each other and independently represent a hydrogen atom, an alkyl group or a protecting group for an amino group;

Z represents a single bond, an oxygen atom, $S(=O)_m$ (wherein m represents 0, 1, or 2), $C(R^{13})(R^{14})$ (wherein $R^{13}$ and $R^{14}$ are the same as or different from each other and independently represent a hydrogen atom or an alkyl group), or $NR^{15}$ (wherein $R^{15}$ represents a hydrogen atom, an alkyl group, or a protecting group for an amino group);

$R^{3c'}$ to $R^{3f'}$ are the same as or different from each other and independently represent a hydrogen atom, or a protecting group for an amino group; and "Base", $R^1$, and $R^2$ are as defined above].

Item 9. A method for producing the compound represented by formula (1) or the salt thereof according to Item 1, the method comprising:

(I) reacting a compound represented by formula (2A):

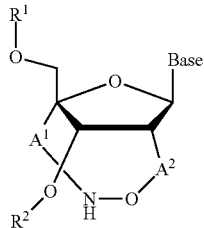
(2A)

(wherein "Base", $A^1$, $A^2$, $R^1$, and $R^2$ are as defined above)

with a compound represented by formula (3A): $L^1$-X—$R^3$ (wherein $L^1$ represents a leaving group; and X and $R^3$ are as defined above); or (II) reacting a compound represented by formula (2B):

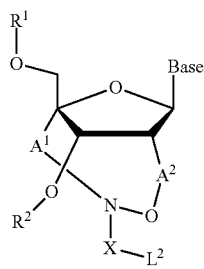
(2B)

(wherein $L^2$ represents a leaving group; and "Base", $A^1$, $A^2$, X, $R^1$, and $R^2$ are as defined above)

with a compound represented by formula (3B): $R^3$—H (wherein $R^3$ is as defined above).

Item 10. A method for producing the compound represented by formula (1) or the salt thereof according to Item 1, wherein $R^3$ represents an amino group which may be protected by a protecting group for an amino group, the method comprising:

(IIIa) reacting a compound represented by formula (2B):

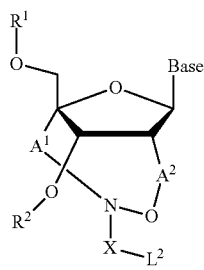
(2B)

(wherein $L^2$ represents a leaving group; and "Base", $A^1$, $A^2$, X, $R^1$, and $R^2$ are as defined above)

with an azide salt to produce a compound represented by formula (1J):

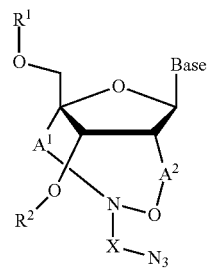
(1J)

(wherein "Base", $A^1$, $A^2$, X, $R^1$, and $R^2$ are as defined above);

(IIIb) reacting the compound represented by formula (1J) with a compound represented by formula (3C):

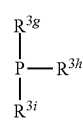
(3C)

(wherein $R^{3g}$ to $R^{3i}$ are the same as or different from each other and independently represent an alkyl group or an aryl group)

and then hydrolyzing the resultant product to produce a compound represented by formula (1L):

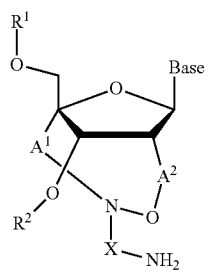
(1L)

(wherein "Base", $A^1$, $A^2$, X, $R^1$, and $R^2$ are as defined above); and (IIIc) optionally protecting an amino group in the compound represented by formula (1L).

Item 11. A method for producing the compound represented by formula (1) or the salt thereof according to Item 1, wherein $R^3$ represents a group represented by formula (B):

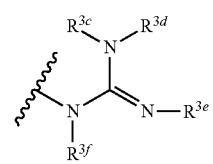
(B)

(wherein $R^{3c}$ to $R^{3f}$ are the same as or different from each other and independently represent a hydrogen atom, an alkyl group, or a protecting group for an amino group), the method comprising guanidinylating a compound represented by formula (1) as recited in Item 1 or a salt thereof wherein $R^3$ represents an amino group.

Item 12. A method for producing the compound represented by formula (1) or the salt thereof according to Item 1, wherein "Base" represents formula (1K') or (1Q'):

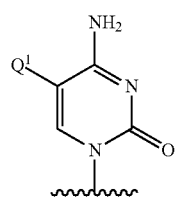

(1K')

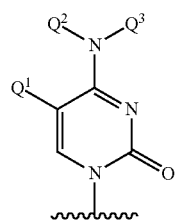

(1Q')

(wherein $Q^1$ represents a hydrogen atom or a substituent; and $Q^2$ and $Q^3$ are the same as or different from each other and independently represent a hydrogen atom or a protecting group for an amino group (provided that a case where each of $Q^2$ and $Q^3$ represents a hydrogen atom is excluded)), the method comprising (VIb) reacting a compound represented by formula (1) as recited in Item 1 or a salt thereof wherein "Base" represents formula (1P'):

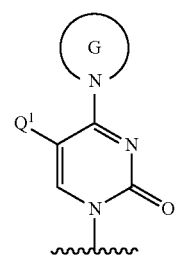

(1P')

(wherein the ring G represents a 5- or 6-membered nitrogenated heterocyclic ring; and $Q^1$ is as defined above)

with ammonia.

Item 13. The method according to Item 12, the method further comprises (VIc) protecting a compound produced by the reaction in the step (VIb) by a protecting group for an amino group.

Item 14. A method for producing the compound represented by formula (1) or the salt thereof according to Item 1, wherein "Base" represents formula (1R') or (1S'):

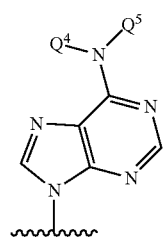

(1R')

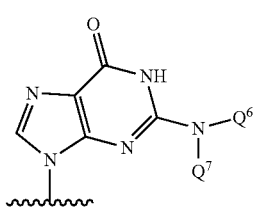

(1S')

(wherein $Q^4$ to $Q^7$ are the same as or different from each other and independently represent a hydrogen atom or a protecting group for an amino group), the method comprising reacting the compound represented by formula (1) according to Item 1, wherein "Base" represents formula (1O'):

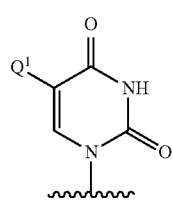

(1O')

(wherein $Q^1$ represents a hydrogen atom or a substituent)

or a salt thereof with a compound represented by formula (3E) or (3F):

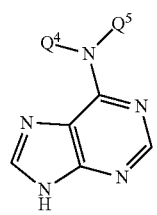

(3E)

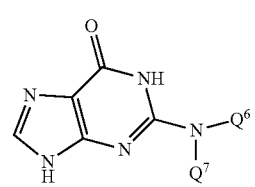

(3F)

(wherein $Q^4$ to $Q^7$ are as defined above).

Item 15. An oligonucleotide comprising a unit represented by formula (4) or a salt thereof:

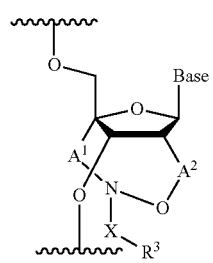

(4)

(wherein
"Base" represents an aromatic heterocyclic group which may have a substituent, or an aromatic hydrocarbon ring group which may have a substituent;
$A^1$ represents a linear alkylene group;
$A^2$ represents a single bond or an alkylene group;
X represents an alkylene group which may have a substituent, or a group having such a structure that at least one methylene group moiety in the alkylene group is substituted by —N($R^X$)— (wherein $R^X$ represents a hydrogen atom or an alkyl group), —O—, or —S(=O)$_k$— (wherein k represents 0, 1, or 2); and
$R^3$ represents an amino group which may have a substituent).

Item 16. A method for detecting a target nucleic acid in a test specimen, the method comprising:
  (I) selectively amplifying a nucleotide sequence containing a target site in the target nucleic acid by a nucleic acid amplification method using a clamp nucleic acid, in which the clamp nucleic acid is the oligonucleotide or the salt thereof according to Item 15; and
  (II) detecting the amplified nucleotide sequence.

Item 17. A composition for detecting a target nucleic acid in a test specimen or for selectively amplifying a nucleotide sequence containing a target site in a target nucleic acid in a test specimen,
  (a) the composition comprising a primer and a probe, in which at least one of the primer and the probe is the oligonucleotide or the salt thereof according to Item 15, or
  (b) the composition comprising a forward primer, a reverse primer and a probe, in which at least one of the forward primer, the reverse primer and the probe is the oligonucleotide or the salt thereof according to Item 15, or
  (c) the composition comprising a clamp nucleic acid and a primer, in which at least one of the clamp nucleic acid and the primer is the oligonucleotide or the salt thereof according to Item 15.

Item 18. A composition for causing an oligonucleotide to strand-invade a target site in double-stranded DNA, the composition containing the oligonucleotide or the salt thereof according to Item 15 which comprises a nucleotide sequence complementary to a nucleotide sequence for the target site.

Item 19. A method for causing an oligonucleotide to strand-invade a target site in isolated double-stranded DNA, the method comprising mixing the oligonucleotide or the salt thereof according to Item 15 which comprises a nucleotide sequence complementary to a nucleotide sequence for the target site.

Item 20. The method according to Item 19, wherein
  the step is (i) mixing the oligonucleotide or the salt thereof with the double-stranded DNA in the presence of a single-stranded DNA-binding protein or (ii) mixing the oligonucleotide or the salt thereof with the double-stranded DNA in the absence of a single-stranded DNA-binding protein, and
  when the step is the step (ii), the method further comprises heating the mixture or retaining the mixture at 25 to 75° C.

BRIEF DESCRIPTION OF THE DRAWINGS

FIGS. 1A-1D are diagrams corresponding to FIG. 5 in Acc. Chem. Res. 1999, 32, pp. 624 to 630, and show the modes of binding of an oligonucleotide to double-stranded genomic DNA;

FIGS. 3A-3E show graphs illustrating the relationship between the number of cycles of PCR and ΔRn (fluorescence intensity). FIG. 3F depicts the percentages designated by the lines in the graphs in FIGS. 3A-3E.

FIGS. 3G and 3H show graphs illustrating the relationship between the number of cycles of PCR and ΔRn (fluorescence intensity). FIG. 3I depicts the percentages designated by the lines in the graphs in FIGS. 3G and 3H;

FIGS. 4A and 4B show diagrams from which the matter that a PNA can strand-invasion under the conditions described in Chem. Commun., 2009, 1225-1227 is confirmed;

FIGS. 5A and 5B show diagrams illustrating that the strand invasion of the oligonucleotides according to the present can occur under the conditions described in Chem. Commun., 2009, 1225-1227;

FIGS. 6A-6C show diagrams illustrating that the strand invasion of the oligonucleotides according to the present invention can occur under specific temperature conditions;

FIGS. 7A-7L show diagrams illustrating that the strand invasion of the oligonucleotide according to the present invention is inhibited due to the difference in a single nucleotide;

FIGS. 8A-8C show diagrams illustrating that the strand invasion of the oligonucleotides according to the present invention can occur under specific temperature conditions;

FIGS. 9A-9C show diagrams illustrating that the strand invasion of the oligonucleotides according to the present invention can occur under specific temperature conditions;

FIG. 10 is a diagram illustrating that strand invasion can be enhanced by using two or more types of oligonucleotides according to the present invention.

DETAILED DESCRIPTION OF THE PREFERRED EMBODIMENTS

Definitions of Terms

Figure 2:
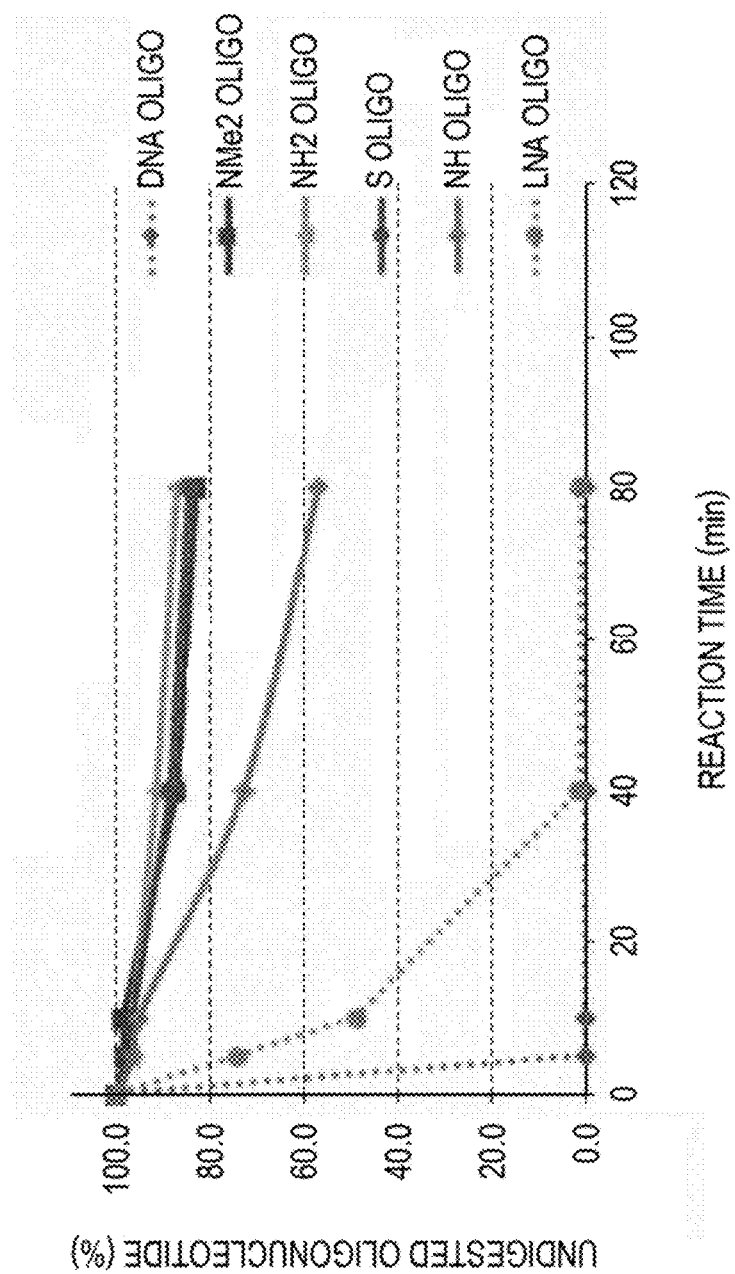
FIG. 2 shows graphs illustrating the relationship between a reaction time of a digestive enzyme and a residual ratio of an undigested oligonucleotide.

In the present description, the term "alkyl group" refers to a monovalent group having such a structure that one hydrogen atom is removed from a linear or branched saturated hydrocarbon.

The number of carbon atoms in the alkyl group is not particularly limited, and is for example 1 to 20, preferably 1 to 10, more preferably 1 to 6, particularly preferably 1 to 4.

Examples of the alkyl group include a methyl group, an ethyl group, a propyl group (e.g., a n-propyl group, an i-propyl group), a butyl group (e.g., a n-butyl group, an i-butyl group, an s-butyl group, a t-butyl group), a pentyl group (e.g., a n-pentyl group, an i-pentyl group, a neopentyl group), a hexyl group, a heptyl group, an octyl group (e.g., a n-octyl group, a 2-ethylhexyl group), and a nonyl group, a decyl group.

In the present description, the term "alkylene group" refers to a bivalent group having such a structure that two hydrogen atoms are removed from a linear or branched saturated hydrocarbon.

The number of carbon atoms in the alkylene group is not particularly limited, and is for example 1 to 10, preferably 1 to 8, more preferably 1 to 6.

Examples of the alkylene group include a $C_1$-alkylene group (e.g., a methylene group), a $C_2$-alkylene group (e.g., a methylmethylene group, a dimethylene group), a $C_3$-alkylene group (e.g., a trimethylene group, a dimethylmethylene group), a $C_4$-alkylene group (e.g., a tetramethylene group), a $C_5$-alkylene group (e.g., a pentamethylene group), and a $C_6$-alkylene group (e.g., a hexamethylene group).

In the present description, the term "alkenyl group" refers to a monovalent group having such a structure that one hydrogen atom is removed from a linear or branched unsaturated hydrocarbon containing a carbon-carbon double bond.

The number of carbon atoms in the alkenyl group is not particularly limited, and is for example 2 to 20, preferably 2 to 10, more preferably 2 to 6.

Examples of the alkenyl group include an ethenyl group (i.e., a vinyl group), a propenyl group (e.g., a 1-propenyl group, an allyl group), a butenyl group, a pentenyl group, a hexenyl group, a geranyl group, and a farnesyl group.

In the present description, the term "alkynyl group" refers to a monovalent group having such a structure that one hydrogen atom is removed from a linear or branched unsaturated hydrocarbon containing a carbon-carbon triple bond.

The number of carbon atoms in the alkynyl group is not particularly limited, and is for example 2 to 20, preferably 2 to 10, more preferably 2 to 6.

Examples of the alkynyl group include an ethynyl group, a propargyl group, and a 1-butynyl group.

In the present description, the term "cycloalkyl group" refers to a monovalent group derived from a saturated aliphatic hydrocarbon ring.

The number of carbon atoms in the cycloalkyl group is not particularly limited, and is for example 3 to 20, preferably 5 to 12, more preferably 5 to 10.

Examples of the cycloalkyl group include a cyclopropyl group, a cyclobutyl group, a cyclopentyl group, a cyclohexyl group, a cycloheptyl group, a cyclooctyl group, a norbornyl group, and an adamantyl group.

In the present description, the term "cycloalkenyl group" refers to a monovalent group derived from an unsaturated aliphatic hydrocarbon ring containing a carbon-carbon double bond.

The number of carbon atoms in the cycloalkenyl group is not particularly limited, and is for example 3 to 20, preferably 5 to 12, more preferably 5 to 10.

Examples of the cycloalkenyl group include a cyclopropenyl group, a cyclobutenyl group, a cyclopentenyl group, a cyclohexenyl group, a norbornenyl group, and an adamantenyl group.

In the present description, the term "aromatic hydrocarbon ring group" refers to a monovalent group derived from an aromatic hydrocarbon ring, and is also referred to as an "aryl group".

The number of constituent atoms in the aromatic hydrocarbon ring is not particularly limited, and is for example 6 to 20, preferably 6 to 14, more preferably 6 to 12, particularly preferably 6 to 10.

The aromatic hydrocarbon ring may be a monocyclic ring or a condensed ring (e.g., a di- to tri-cyclic condensed ring).

Examples of the aromatic hydrocarbon ring group include a phenyl group, an indenyl group, a naphthyl group, a fluorenyl group, a phenanthrenyl group, and an anthracenyl group.

In the present description, the term "heterocyclic ring" is used in the meaning that an "aliphatic heterocyclic ring" and an "aromatic heterocyclic ring" are included.

In the present description, the term "aliphatic heterocyclic ring" refers to an aliphatic ring which contains, as ring constituent atoms, a carbon atom and at least one hetero atom selected from the group consisting of a nitrogen atom, an oxygen atom, a sulfur atom, a silicon atom and the like.

The number of constituent atoms in the aliphatic heterocyclic ring is not particularly limited, and is for example 5 to 20, preferably 5 to 12, more preferably 6 to 10.

The number of hetero atom(s) among the constituent atoms of the aliphatic heterocyclic ring is not particularly limited, and is for example 1 to 4.

Examples of the aliphatic heterocyclic ring include an oxygenated aliphatic heterocyclic ring (e.g., tetrahydrofuran, dioxolane, pyran, tetrahydropyran, dioxane), a sulfur-containing aliphatic heterocyclic ring (e.g., tetrahydrothiophene, thiopyran, tetrahydrothiopyran), a nitrogenated aliphatic heterocyclic ring (e.g., pyrrolidine, piperidine, azepane), a nitrogenated and oxygenated aliphatic heterocyclic ring (e.g., morpholine), a nitrogenated and sulfur-containing aliphatic heterocyclic ring (e.g., thiomorpholine), and an aliphatic heterocyclic ring containing a siloxane bond.

In the present description, the term "aromatic heterocyclic ring" refers to an aromatic ring containing, as ring constituent atoms, a carbon atom and at least one hetero atom selected from the group consisting of a nitrogen atom, an oxygen atom, a sulfur atom and the like.

The number of constituent atoms in the aromatic heterocyclic ring is not particularly limited, and is for example 5 to 20, preferably 5 to 12, more preferably 6 to 10.

The number of hetero atom(s) among the constituent atoms of the aromatic heterocyclic ring is not particularly limited, and is for example 1 to 4.

The aromatic heterocyclic ring may be a monocyclic ring or a condensed ring (e.g., a di- or tri-cyclic condensed ring).

Examples of the aromatic heterocyclic ring include an oxygenated aromatic heterocyclic ring (e.g., furan, benzofuran, isobenzofuran, chromene, benzopyran, xanthene), a sulfur-containing aromatic heterocyclic ring (e.g., thiophene, thianthrene), a nitrogenated aromatic heterocyclic ring (e.g., pyrrole, imidazole, pyrazole, triazole, pyridine, pyrazine, pyrimidine, pyridazine, indole, isoindole, indolizine, purine, quinoline, isoquinoline, 1,8-naphthyridine, quinoxaline, quinazoline, cinnoline, phthalazine, pteridine, carbazole, phenanthridine, acridine, perimidine, phenazine), an oxygenated and sulfur-containing aromatic heterocyclic ring (e.g., phenoxathiin), a nitrogenated and oxygenated aromatic heterocyclic ring (e.g., oxazole, isoxazole, furazan, phenoxazine), and a nitrogenated and sulfur-containing aromatic heterocyclic ring (e.g., thiazole, isothiazole, phenothiazine).

In the present description, the term "heterocyclic group" refers to a monovalent group having such a structure that one hydrogen atom is removed from the heterocyclic ring.

In the present description, the wording "may have a substituent" or "may be substituted by a substituent" is used in the meaning including both of a case where no substituent is contained and a case where one substituent or two or more same-type or different-type substituents are contained in place of an arbitrary hydrogen atom. When a substituent or substituents is/are contained, the number of the substituent (s) is not particularly limited, and is for example 1 to 3, preferably 1 or 2.

In the present description, the term "substituent" refers to an atom or an atomic group which is replaced for a hydrogen atom. Examples of the substituent include a halogen atom (e.g., a fluorine atom, a chlorine atom, a bromine atom, a iodine atom), an oxo group (=O), a thioxo group (=S), a hydroxyl group, a mercapto group, an amino group, a carboxy group, an alkyl group, an alkenyl group, a cycloalkyl group, a cycloalkenyl group, an aryl group, an alkynyl group, an acyl group, an alkylsulfonyl group, an arylsulfonyl group, a cyano group, a heterocyclic group, and a combination of any two or more of them (e.g., a haloalkyl group, a cyanoalkyl group, an aralkyl group, an alkoxy group, an alkylamino group).

The term "a combination of two or more of them" includes an arbitrary combination of the groups which are exemplified as the substituents.

In the present description, the term "Cx-y" means that the number of carbon atom(s) in a group following this term is x to y inclusive. Each of x and y represents a positive integer, in which x and y satisfy the requirement represented by the formula: x<y.

In the present description, the term "haloalkyl group" refers to an alkyl group substituted by one halogen atom or two or more same or different halogen atoms.

A preferred example of the haloalkyl group is a $C_{1-6}$ haloalkyl group, a more preferred example is a $C_{1-4}$ haloalkyl group, and a still more preferred example is a trifluoromethyl group, a trichloromethyl group, or a 2,2,2-trifluoroethyl group.

In the present description, the term "cyanoalkyl group" refers to an alkyl group substituted by one cyano group or two or more cyano groups.

A preferred example of the cyanoalkyl group is a $C_{1-6}$ cyanoalkyl group, a more preferred example is a $C_{1-4}$ cyanoalkyl group, and a still more referred example is a cyanomethyl group or a 2-cyanoethyl group.

In the present description, the term "aralkyl group" refers to an alkyl group substituted by one aryl group or two or more same or different aryl groups.

A preferred example of the aralkyl group is a $C_{6-14}$-aryl-$C_{1-4}$-alkyl group, and a more preferred example is a phenylmethyl group (i.e., a benzyl group), a phenylethyl group (i.e., a phenethyl group), a naphthylmethyl group, a naphthylethyl group, a triphenylmethyl group (i.e., a trityl group), or a fluorenylmethyl group.

In the present description, the term "alkoxy group" refers to a group represented by the formula: —O-alkyl.

A preferred example of the alkoxy group is a $C_{1-6}$ alkoxy group, and a more preferred example is a methoxy group, an ethoxy group, a propoxy group (e.g., a n-propoxy group, an i-propoxy group), or a butoxy group (e.g., a t-butoxy group).

The haloalkoxy group and the cyanoalkoxy group refer to a group represented by the formula: —O-haloalkyl and a group represented by the formula: —O-cyanoalkyl, respectively.

In the present description, the term "alkylthio group" refers to a group represented by the formula: —S-alkyl. A preferred example of the alkylthio group is a $C_{1-6}$ alkylthio group, and a more preferred example is a methyltho group, an ethyltho group, a propylthio group (e.g., a n-propylthio group, an i-propyltho group), or a butyltho group.

A haloalkylthio group and a cyanoalkylthio group refer to a group represented by the formula: —S-haloalkyl and a group represented by the formula: —S-cyanoalkyl, respectively.

In the present description, the term "alkylamino group" refers to an amino group which is substituted by one or two same or different alkyl groups.

The alkylamino group includes a monoalkylamino group and a dialkylamino group.

A preferred example of the monoalkylamino group is a mono-$C_{1-6}$ alkylamino group, and a more preferred example is a monomethylamino group, a monoethylamino group, a monopropylamino group (e.g., a mono(n-propyl)amino group, a mono(i-propyl)amino group), or a monobutylamino group.

A preferred example of the dialkylamino group is a di-$C_{1-6}$ alkylamino group, and a more preferred example is a dimethylamino group, a diethylamino group, a dipropylamino group (e.g., a di(n-propyl)amino group, a di(i-propyl)amino group), or a dibutylamino group.

In the present description, the term "phosphino group which has a substituent" refers to a group having such a structure that at least one hydrogen atom in a phosphino group (—$PH_2$) is substituted by another atom or atomic group.

An example of the phosphino group which has a substituent is a group represented by the formula: —P($R^5$)($R^6$) (wherein $R^5$ and $R^6$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group).

In the present description, the term "dihydroxyphosphinyl group which may have a substituent" refers to a dihydroxyphosphinyl group (i.e., a phosphono group) (—P(=O)(OH)$_2$) or a dihydroxyphosphinyl group in which at least one hydrogen atom is substituted by another atom or an atomic group (e.g., a protecting group for a hydroxyl group).

The latter group includes a group represented by the following formula:

[Formula 19]

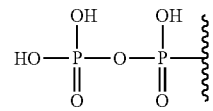

which may have a substituent (hereinafter, also referred to as a "diphosphate group"), and a group represented by the following formula:

[Formula 20]

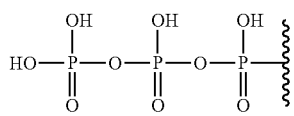

which may have a substituent (hereinafter, also referred to as a "triphosphate group").

In the present description, the term "hydroxymercaptophosphinyl group which may have a substituent" refers to a hydroxymercaptophosphinyl group (—P(=O)(OH)(SH)) or a hydroxymercaptophosphinyl group in which at least one hydrogen atom is substituted by another atom or an atomic group (e.g., a protecting group for a hydroxyl group).

In the present description, the term "protecting group for a hydroxyl group" refers to a monovalent group which can prevent a hydroxyl group from being involved in a reaction for the synthesis of a compound or a salt thereof or a reaction for the synthesis of an oligonucleotide or a salt thereof.

An example of the protecting group for a hydroxyl group is, but is not limited to, a group which is stable under an acidic or neutral condition and can be cleaved by a method such as a hydrogenolysis, a hydrolysis, an electrolysis and a photodissociation.

Specific examples of the protecting group for a hydroxyl group include an acyl group which may have a substituent, a sulfonyl group which has a substituent, and a silyl group which has a substituent.

In the present description, the term "acyl group" refers to a group represented by the formula: —C(=O)—R (wherein R represents a hydrocarbon group). The hydrocarbon group represented by R may be a linear or branched hydrocarbon group (e.g., an alkyl group), or may be a saturated or unsaturated hydrocarbon ring group (e.g., a cycloalkyl group, an aryl group), or may be a combination thereof (e.g., an aralkyl group).

Examples of the acyl group include an alkylcarbonyl group, an arylcarbonyl group, and an aralkylcarbonyl group.

A preferred example of the alkylcarbonyl group is a ($C_{1-10}$-alkyl)carbonyl group, and a more preferred example is an acetyl group, a propionyl group, a butyryl group, an isobutyryl group, a pentanoyl group, a pivaloyl group, a valeryl group, an isovaleryl group, an octanoyl group, a nonanoyl group, or a decanoyl group.

A preferred example of the arylcarbonyl group is a ($C_{6-14}$-aryl)carbonyl group, and a more preferred example is a benzoyl group, or a naphthoyl group (i.e., an α-naphthoyl group, a β-naphthoyl group).

A preferred example of the aralkylcarbonyl group is a ($C_{6-14}$-aryl-$C_{1-4}$-alkyl)carbonyl group, and a more preferred example is a benzylcarbonyl group.

With respect to the acyl group in the "acyloxy group", the "acylthio group" and the "acylamino group", the same groups as mentioned above can be exemplified.

In the present description, the term "sulfonyl group which has (having) a substituent" refers to a group represented by the formula: —S(=O)$_2$R (wherein R is as defined above).

The sulfonyl group which has a substituent includes a sulfonyl group which has an alkyl group which may have a substituent, and a sulfonyl group which has an aryl group which may have a substituent.

A preferred example of the sulfonyl group having an alkyl group is a $C_{1-6}$-alkylsulfonyl group, and a more preferred example is a methanesulfonyl group or an ethanesulfonyl group.

A preferred example of the sulfonyl group having an aryl group is a $C_{6-14}$-arylsulfonyl group, and a more preferred example is a benzenesulfonyl group or a p-toluenesulfonyl group.

In the present description, the term "silyl group which has (having) a substituent" refers to a silyl group having such a structure that at least one hydrogen atom in a silyl group (—SiH$_3$) is substituted by another atom or an atomic group.

A typical example of the "silyl group which has (having) a substituent" is a group represented by the formula: —Si(R$^4$)$_3$ (wherein R$^4$'s are the same as or different from each other and independently represent an alkyl group or an aryl group). Examples of the group include a trialkylsilyl group (e.g., a tri-$C_{1-6}$-alkylsilyl group such as a trimethylsilyl group, a triethylsilyl group, a triisopropylsilyl group and a t-butyldimethylsilyl group), a dialkylarylsilyl group (e.g., a di-$C_{1-6}$-alkyl-$C_{6-14}$-arylsilyl group such as a dimethyl(phenyl)silyl group), an alkyldiarylsilyl group (e.g., a $C_{1-6}$-alkyl-di-$C_{6-14}$-arylsilyl group such as a t-butyldiphenylsilyl group), and a triarylsilyl group (e.g., a tri-$C_{6-14}$-arylsilyl group such as a triphenylsilyl group).

In the present description, the term "protecting group for an amino group" refers to a monovalent group which can prevent an amino group from being involved in a reaction in the synthesis of a compound or a salt thereof or the synthesis of an oligonucleotide or a salt thereof.

The protecting group for an amino group is, for example, but is not limited to, a group which is stable under an acidic or neutral condition and can be cleaved by a method such as a hydrogenolysis, a hydrolysis, an electrolysis and a photodissociation.

Examples of the protecting group for an amino group include an acyl group which may have a substituent (e.g., an alkylcarbonyl group which may have a substituent, an arylcarbonyl group which may have a substituent, an aralkylcarbonyl group which may have a substituent), an N,N-dialkylformamidyl group which may have a substituent, an alkoxycarbonyl group which may have a substituent, an alkenyloxycarbonyl group which may have a substituent, an aryloxycarbonyl group which may have a substituent, an aralkyloxycarbonyl group which may have a substituent, and a sulfonyl group which has a substituent.

In the present description, the term "formamidyl group" refers to a group represented by the formula: =CH—NH$_2$. A preferred example of an N,N-dialkylformamidyl group is an N,N-di($C_{1-6}$-alkyl)formamidyl group, a more preferred example is an N,N-di($C_{1-4}$-alkyl)formamidyl group, and a still more preferred example is an N,N-dimethylformamidyl group or an N,N-diethylformamidyl group.

In the present description, the term "alkoxycarbonyl group" refers to a group represented by the formula: —C(=O)—O-alkyl.

A preferred example of the alkoxycarbonyl group is a ($C_{1-6}$-alkoxy)carbonyl group, and a more preferred example is a methoxycarbonyl group, an ethoxycarbonyl group, a propoxycarbonyl group, or a butoxycarbonyl group (e.g., a t-butoxycarbonyl group).

In the present description, the term "alkenyloxycarbonyl group" refers to a group represented by the formula: —C(=O)—O-alkenyl.

A preferred example of the alkenyloxycarbonyl group is a ($C_{2-9}$-alkenyloxy)carbonyl group, and a more preferred example is an allyloxycarbonyl group.

In the present description, the term "aryloxycarbonyl group" refers to a group represented by the formula: —C(=O)—O-aryl.

A preferred example of the aryloxycarbonyl group is a (C$_{6-14}$-aryloxy)carbonyl group, and a more preferred example is a phenoxycarbonyl group or a naphthoxycarbonyl group.

In the present description, the term "aralkyloxycarbonyl group" refers to a group represented by the formula: —C(=O)—O-aralkyl.

A preferred example of the aralkyloxycarbonyl group is a (C$_{6-14}$-aryl-C$_{1-4}$-alkoxy)carbonyl group, and a more preferred example is a benzyloxycarbonyl group or a fluorenylmethyloxycarbonyl group.

In the present description, the wording "hybridize" refers to a matter that the full length or a part of a given polynucleotide or oligonucleotide and the full length or a part of another polynucleotide or oligonucleotide together form a double strand through hydrogen bonds under a stringent condition. The "stringent condition" may be one which has been commonly employed by a person skilled in the art in the hybridization of a polynucleotide or an oligonucleotide. For example, when there is at least 50%, preferably at least 75%, more preferably at least 90% sequence identity between two polynucleotide or oligonucleotide molecules, the "stringent condition" may be a condition where one of the polynucleotide or oligonucleotide molecules can hybridize with the other specifically. It is known that the stringency in the hybridization is a function of a temperature, a salt concentration, a nucleotide length and a GC content in a polynucleotide or oligonucleotide, and the concentration of a chaotropic agent in a hybridization buffer solution. For example, as the stringent condition, a condition described in Sambrook, J. et. al., 1998, Molecular Cloning: A Laboratory Manual (second edition), Cold Spring Harbor Laboratory Press, New York can be employed.

In the present description, the term "test" refers to the matter that an analyte, e.g., a nucleic acid, in a specimen is examined for the purpose of diagnosis, research or the like. The term "test specimen" refers to a specimen to be subjected to a test.

In the present description, the upper limit and the lower limit of a numerical range may be combined arbitrarily.

<<Compound or Salt Thereof>>

The compound or a salt thereof according to the present invention is a compound represented by formula (1) or a salt thereof:

[Formula 21]

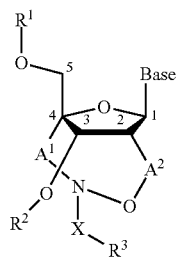

(1)

(wherein "Base", A$^1$, A$^2$, X, R$^1$, R$^2$ and R$^3$ are as defined above; and position numbers are assigned to carbon atoms in the furanose).

Hereinbelow, a compound represented by formula (N) or a salt thereof refers to a "compound (N)".

A compound (1) is referred to as a "nucleotide" when R$^1$ or R$^2$ represents a dihydroxyphosphinyl group which may have a substituent or a hydroxymercaptophosphinyl group which may have a substituent, and is referred to as a "nucleoside" when R$^1$ or R$^2$ represents another group.

Preferred examples of "Base" include an aromatic heterocyclic group which may have a substituent.

The aromatic heterocyclic group is preferably a nitrogenated aromatic heterocyclic group.

The nitrogenated aromatic heterocyclic group is preferably a 6- to 10-membered nitrogenated aromatic heterocyclic group. The 6- to 10-membered nitrogenated aromatic heterocyclic group is preferably a 2,4-dioxo-1,2,3,4-tetrahydropyrimidin-1-yl group, a 2-oxo-1,2-dihydropyrimidin-1-yl group, a purin-9-yl group, or a 6-oxo-1,6-dihydro-9H-purin-9-yl group.

A preferred example of the substituent which replaces in the aromatic heterocyclic group is at least one residue selected from the group consisting of an alkyl group, an acyl group, and an amino group which may be substituted by a protecting group for an amino group. The number of the substituent(s) is not particularly limited, and is for example 1 to 3.

A more preferred example of "Base" is a thyminyl group which may have a substituent, a cytosinyl group which may have a substituent, an adenyl group which may have a substituent, or a guanyl group which may have a substituent. The substituent is preferably at least one residue selected from the group consisting of an alkyl group, an acyl group, and an N,N-dialkylformamidyl group, more preferably a Cia-alkyl group, a (C$_{1-4}$-alkyl)carbonyl group, a (C$_{6-14}$-aryl) carbonyl group, or an N,N-di(C$_{1-4}$-alkyl)formamidyl group. The number of the substituent(s) is preferably 1 to 3.

A still more preferred example of "Base" is a group selected from the group consisting of:

a 2,4-dioxo-5-methyl-1,2,3,4-tetrahydropyrimidin-1-yl group (e.g., a thymin-1-yl group), a 2-oxo-4-amino-1,2-dihydropyrimidin-1-yl group (i.e., a cytosin-1-yl group), a 2-oxo-4-acylamino-1,2-dihydropyrimidin-1-yl group (i.e., an N-acyl-cytosin-1-yl group), a 2-oxo-4-amino-5-methyl-1,2-dihydropyrimidin-1-yl group (i.e., a 5-methylcytosin-1-yl group), a 2-oxo-4-acylamino-5-methyl-1,2-dihydropyrimidin-1-yl group (i.e., an N-acyl-5-methylcytosin-1-yl group), a 6-amino-9H-purin-9-yl group (i.e., an adenin-9-yl group), a 6-acylamino-9H-purin-9-yl group (i.e., an N-acyl-adenin-9-yl group), a 2-amino-6-oxo-1,6-dihydro-9H-purin-9-yl group (e.g., guanin-9-yl group), a 2-acylamino-6-oxo-1,6-dihydro-9H-purin-9-yl group (e.g., an N-acyl-guanin-9-yl group), and a 2-(N,N-dialkylformamidyl)amino-6-oxo-1,6-dihydro-9H-purin-9-yl group (e.g., an N-(N,N-dialkylformamidyl)-guanin-9-yl group).

A most preferred example of "Base" is a group selected from the group consisting of:

a thymin-1-yl group, a 5-methylcytosin-1-yl group, an N-acetyl-5-methylcytosin-1-yl group, an N-isobutyryl-5-methylcytosin-1-yl group, an N-benzoyl-5-methylcytosin-1-yl group, an adenin-9-yl group, an N-acetyl-adenin-9-yl group, an N-isobutyryl-adenin-9-yl group, an N-benzoyl-adenin-9-yl group, a guanin-9-yl group, an N-acetyl-guanin-9-yl group, an N-isobutyrylguanin-9-yl group, an N-benzoyl-guanin-9-yl group, and
an N-(N,N-dimethylformamidyl)-guanin-9-yl group.

$A^1$ is a linear alkylene group (e.g., a methylene group, a dimethylene group, a trimethylene group, a tetramethylene group).

A preferred example of $A^1$ is a linear $C_{1-4}$ alkylene group.

A more preferred example of $A^1$ is a linear $C_{1-2}$ alkylene group.

A most preferred example of $A^1$ is a methylene group.

A preferred example of $A^2$ is a single bond or a linear $C_{1-2}$ alkylene group (e.g., a methylene group, a dimethylene group).

A more preferred example of $A^2$ is a single bond.

A preferred example of X is an alkylene group, or a group having such a structure that at least one of methylene group moieties excluding a methylene group moiety bound to a nitrogen atom in the alkylene group and a methylene group moiety bound to $R^3$ in the methylene group is replaced by —N($R^X$)— (wherein $R^X$ represents a hydrogen atom or an alkyl group), —O—, or —S(=O)$_k$— (wherein k represents 0, 1 or 2). Alternatively, a preferred example of X is an alkylene group, or a group having such a structure that —N($R^X$)— (wherein $R^X$ is as defined above), —O—, or —S(=O)$_k$— (wherein k is 0, 1, or 2) is inserted between adjacent two carbon atoms in the alkylene group.

A more preferred example of X is a group selected from the group consisting of:
 a group represented by the formula: —$C_nH_{2n}$— (wherein n represents an integer of 1 to 10);
 a group represented by the formula: —(CH$_2$)$_{n1}$—(N(R$^{X1}$)—(CH$_{2n2}$)$_{n3}$— (wherein $R^{X1}$ represents a hydrogen atom or a $C_{1-4}$ alkyl group; n1 represents an integer of 2 to 10; n2 represents an integer of 2 to 4; n3 represents an integer of 1 to 5; when n3 represents an integer of 2 or more, $R^{X1}$'s may be the same as or different from each other and n2's may be the same as or different from each other);
 a group represented by the formula: —(CH$_2$)$_{n4}$—(O—(CH$_2$)$_{n5}$)$_{n6}$— (wherein n4 represents an integer of 2 to 10; n5 represents an integer of 2 to 4; n6 represents an integer of 1 to 5; when n6 represents an integer of 2 or more, n5's may be the same as or different from each other); and
 a group represented by the formula: —(CH$_2$)$_{n7}$—(S—(CH$_2$)$_{n8}$)$_{n9}$— (wherein n7 represents an integer of 2 to 10; n8 represents an integer of 2 to 4; n9 represents an integer of 1 to 5; when n9 represents an integer of 2 or more, n8's may be the same as or different from each other).

A most preferred example of X is a group selected from the group consisting of:
 a group represented by the formula: —(CH$_2$)$_{n10}$— (wherein n10 represents an integer of 1 to 6);
 a group represented by the formula: —C$_2$H$_4$—(N(R$^{X2}$)—C$_2$H$_4$)$_{n11}$— (wherein $R^{X2}$ represents a hydrogen atom or a $C_{1-4}$ alkyl group; n11 represents an integer of 1 to 5; when n11 represents an integer of 2 or more, $R^{X2}$'s may be the same as or different from each other);
 a group represented by the formula: —C$_2$H$_4$—(O—C$_2$H$_4$)$_{n12}$— (wherein n12 represents an integer of 1 to 5); and
 a group represented by the formula: —C$_2$H$_4$—(S—C$_2$H$_4$)$_{n13}$— (wherein n13 represents an integer of 1 to 5).

The substituent which can substitute arbitrarily on a carbon atom in the alkylene group is preferably a halogen atom, a hydroxyl group, an alkoxy group, a mercapto group, an alkylthio group, an amino group, a monoalkylamino group, a dialkylamino group, an acyloxy group, an acylamino group or an acylthio group. The number of substituent(s) may vary depending on the number of carbon atoms in the alkylene group, and is for example an integer of 1 to 3, preferably 2 or 3.

A preferred example of $R^1$ is a group selected from the group consisting of:
 a hydrogen atom;
 an alkyl group which may have a substituent;
 an aryl group which may have a substituent;
 a protecting group for a hydroxyl group;
 a phosphino group which has a substituent;
 a dihydroxyphosphinyl group which may have a substituent; and
 a hydroxymercaptophosphinyl group which may have a substituent.

The "alkyl group which may have a substituent" represented by $R^1$ is preferably an alkyl group which may have at least one substituent selected from the group consisting of a halogen atom, an alkoxy group and an aryl group, more preferably an alkyl group which may be substituted by an alkoxy group or an aralkyl group which may be substituted by an alkoxy group. The number of the substituent(s) is preferably 1 to 3.

The "aryl group which may have a substituent" represented by $R^1$ is preferably an aryl group which may have at least one substituent selected from the group consisting of a halogen atom, an alkyl group and an alkoxy group, more preferably an aryl group which may be substituted by an alkoxy group. The number of the substituent(s) is preferably 1 to 3.

The "protecting group for a hydroxyl group" represented by $R^1$ is preferably an alkylcarbonyl group, an arylcarbonyl group, an alkylsulfonyl group, an arylsulfonyl group, or a group represented by the formula: —Si($R^4$)$_3$ (wherein $R^4$'s are the same as or different from each other and independently represent an alkyl group or an aryl group).

The "phosphino group which has a substituent" represented by $R^1$ is preferably a group represented by the formula: —P($R^5$)($R^6$) (wherein $R^5$ and $R^6$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group). A more preferred example of the group is a phosphino group represented by the formula:

[Formula 22]

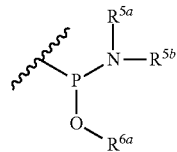

(wherein $R^{5a}$ and $R^{5b}$ are the same as or different from each other and independently represent a hydrogen atom or an alkyl group; and $R^{6a}$ represents a hydrogen atom, an alkyl group, a haloalkyl group, or a cyanoalkyl group).

The "dihydroxyphosphinyl group which may have a substituent" represented by $R^1$ is preferably a dihydroxyphosphinyl group, a diphosphate group, or a triphosphate group, more preferably a dihydroxyphosphinyl group. These groups may have a protecting group for a hydroxyl group as a substituent, in which each of all or some of hydrogen atoms may be substituted by a protecting group for a hydroxyl group.

The "hydroxymercaptophosphinyl group which may have a substituent" represented by $R^1$ is preferably a hydroxymercaptophosphinyl group.

A most preferred example of $R^1$ is a hydrogen atom, a methyl group, an ethyl group, a propyl group, a butyl group, an allyl group, a benzyl group, a trityl group, a methoxymethyl group, a p-methoxybenzyl group, a monomethoxytrityl group, a dimethoxytrityl group, an acetyl group, an isobutyryl group, a benzoyl group, a methanesulfonyl group, a p-toluenesulfonyl group, a trimethylsilyl group, a triethylsilyl group, a triisopropylsilyl group, a t-butyldimethylsilyl group, a t-butyldiphenylsilyl group, a phosphino group represented by either one of the formulae:

[Formula 23]

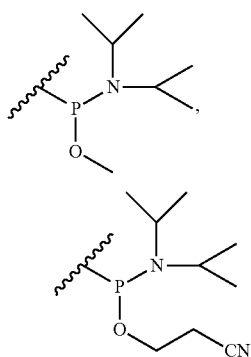

a dihydroxyphosphinyl group, or a hydroxymercaptophosphinyl group.

Preferred examples of $R^2$ are the same as those of $R^1$.

A preferred example of the combination of $R^1$ and $R^2$ is a combination in which $R^1$ is a hydrogen atom or a dimethoxytrityl group (e.g., a 4,4'-dimethoxytrityl group) and $R^2$ is a phosphino group represented by the formula:

[Formula 24]

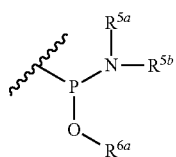

(wherein $R^{5a}$ and $R^{5b}$ are the same as or different from each other and independently represent a hydrogen atom or an alkyl group; and $R^{6a}$ represents a hydrogen atom, an alkyl group, a haloalkyl group, or a cyanoalkyl group).

When $R^1$ and $R^2$, two oxygen atoms respectively adjacent to $R^1$ and $R^2$ and carbon atoms located at position-3 and position-5 in a furanose together form a ring, a preferred example of the ring is a 6- to 10-membered aliphatic heterocyclic ring which may have a substituent, in which a preferred example of the substituent is an alkyl group.

A more preferred example of the ring is an aliphatic heterocyclic ring represented by either one of the formulae:

[Formula 25]

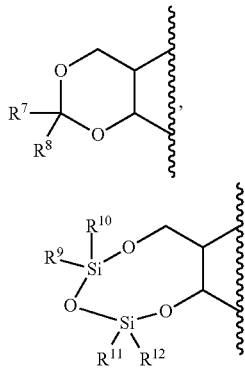

(wherein $R^7$ and $R^8$ are the same as or different from each other and independently represent a hydrogen atom or an alkyl group; and $R^9$ to $R^{12}$ are the same as or different from each other and independently represent an alkyl group).

A still more preferred example of the ring is a ring represented by any one of the formulae:

[Formula 26]

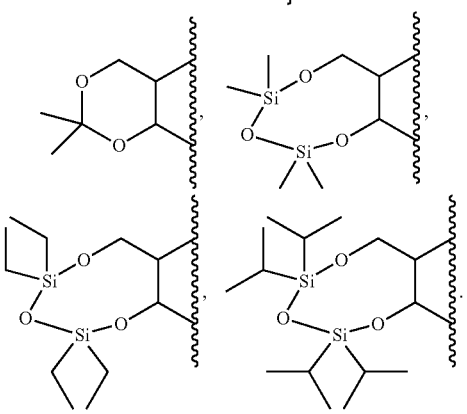

A preferred example of $R^3$ is a group represented by formula (A):

[Formula 27]

(A)

(wherein $R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and the adjacent nitrogen atom together form a ring which may have a substituent).

$R^{3a}$ is preferably a hydrogen atom, an alkyl group, an aryl group, an aralkyl group, or a protecting group for an amino group, more preferably a hydrogen atom, an alkyl group, or a protecting group for an amino group.

The "protecting group for an amino group" represented by $R^{3a}$ is preferably a $(C_{1-4}$-alkyl)carbonyl group or a $(C_{1-4}$-haloalkyl)carbonyl group, more preferably an acetyl group or a trifluoromethylcarbonyl group.

Preferred examples of $R^{3b}$ are the same as those of $R^{3a}$.

A preferred example of the combination of $R^{3a}$ and $R^{3b}$ is a combination in which each of $R^{3a}$ and $R^{3b}$ is a hydrogen atom, a combination in which $R^{3a}$ is a hydrogen atom and $R^{3b}$ is an acetyl group or a trifluoromethylcarbonyl group, a combination in which each of $R^{3a}$ and $R^{3b}$ is a methyl group, or a combination in which each of $R^{3a}$ and $R^{3b}$ is an acetyl group or a trifluoromethylcarbonyl group.

When $R^{3a}$, $R^{3b}$ and the adjacent nitrogen atom together form a ring, a preferred example of the ring is a 5- to 10-membered nitrogenated aliphatic heterocyclic ring which may have a substituent, in which a preferred example of the substituent is an alkyl group or an acyl group.

A more preferred example of the ring is an aliphatic heterocyclic ring represented by either one of the formulae:

[Formula 28]

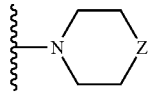

[wherein Z represents a single bond, an oxygen atom, $S(=O)_m$ (wherein m represents 0, 1 or 2), $C(R^{13})(R^{14})$ (wherein $R^{13}$ and $R^{14}$ are the same as or different from each other and independently represent a hydrogen atom or an alkyl group), or $NR^{15}$ (wherein $R^{15}$ represents a hydrogen atom, an alkyl group, or an acyl group).

A still more preferred example of the ring is a ring represented by any one of the formulae:

[Formula 29]

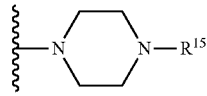

[wherein $R^{15}$ represents a hydrogen atom, a linear or branched $C_{1-4}$ alkyl group (e.g., a methyl group, an ethyl group, a propyl group, a butyl group), or a (linear or branched $C_{1-4}$-alkyl)carbonyl group (e.g., a methylcarbonyl group, an ethylcarbonyl group, a propylcarbonyl group, a butylcarbonyl group)].

A most preferred example of the ring is a 4-methylpiperazin-1-yl group.

Another preferred example of $R^3$ is a group represented by the formula (B):

[Formula 30]

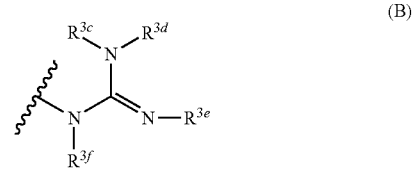

(wherein $R^{3c}$ to $R^{3f}$ are the same as or different from each other and independently represent a hydrogen atom, an alkyl group, or a protecting group for an amino group).

A preferred example of each of $R^{3c}$ to $R^{3f}$ is a hydrogen atom, or a protecting group for an amino group.

$R^{3c}$ is preferably a hydrogen atom.

$R^{3d}$ is preferably a protecting group for an amino group, more preferably an alkoxycarbonyl group, a haloalkoxycarbonyl group, or a cyanoalkoxycarbonyl group, particularly preferably a $(C_{1-4}$-alkoxy)carbonyl group, a $(C_{1-4}$-haloalkoxy)carbonyl group, or a $(C_{1-4}$-cyanoalkoxy)carbonyl group.

$R^{3e}$ is preferably a protecting group for an amino group, more preferably an alkoxycarbonyl group, a haloalkoxycarbonyl group, or a cyanoalkoxycarbonyl group, particularly preferably a $(C_{1-4}$-alkoxy)carbonyl group, a $(C_{1-4}$-haloalkoxy)carbonyl group, or a $(C_{1-4}$-cyanoalkoxy)carbonyl group.

$R^{3f}$ is preferably a hydrogen atom.

A most preferred example of $R^3$ is a group selected from the following group:

[Formula 31]

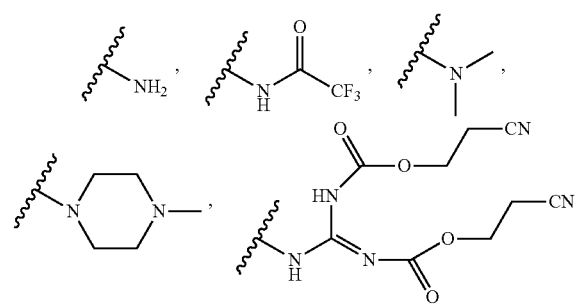

A preferred example of the compound (1) is any one of compounds (1A) to (1C):

[Formula 32]

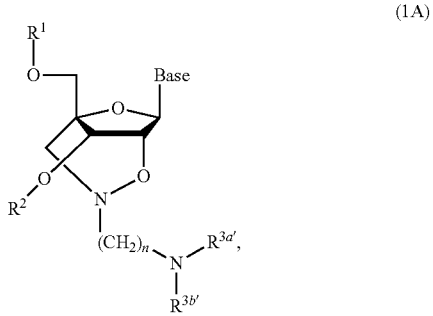

(1B)

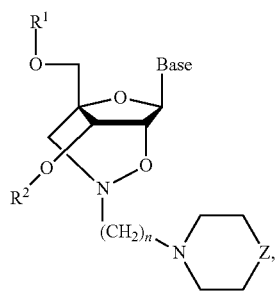

(1C)

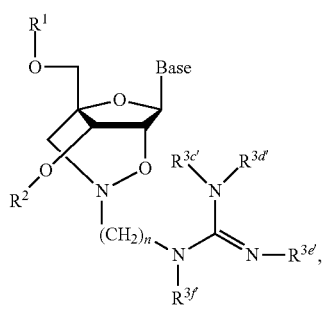

[wherein:
$R^{3a'}$ and $R^{3b'}$ are the same as or different from each other and independently represent a hydrogen atom, an alkyl group, or a protecting group for an amino group;

Z represents a single bond, an oxygen atom, $S(=O)_m$ (wherein m represents 0, 1 or 2), $C(R^{13})(R^{14})$ (wherein $R^{13}$ and $R^{14}$ are the same as or different from each other and independently represent a hydrogen atom or an alkyl group), or $NR^{15}$ (wherein $R^{15}$ represents a hydrogen atom, an alkyl group, or a protecting group for an amino group);

$R^{3c'}$ to $R^{3f'}$ are the same as or different from each other and independently represent a hydrogen atom, or a protecting group for an amino group; and "Base", $R^1$, $R^2$, and n are as defined above].

A more preferred example of the compound (1) is any one of compounds (1D) to (1I):

[Formula 33]

(1D)

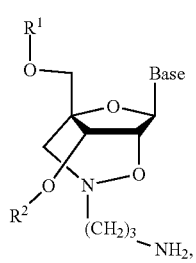

(1E)

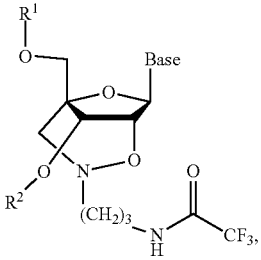

(1F)

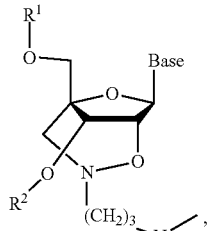

(1G)

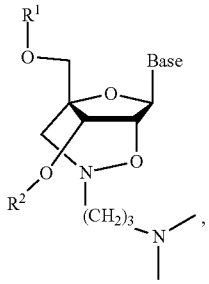

(1H)

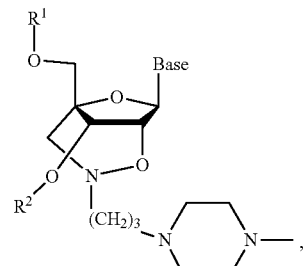

(1I)

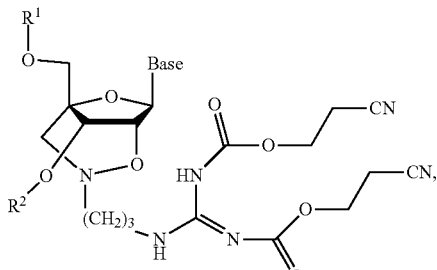

(wherein "Base", $R^1$, and $R^2$ are as defined above).

The salt may be a pharmaceutically acceptable salt or may not be a pharmaceutically acceptable salt. The salt may be an inorganic salt or an organic salt.

Examples of the salt include an alkali metal salt (e.g., a sodium salt, a potassium salt, a lithium salt), an alkaline earth metal salt (e.g., a calcium salt, a magnesium salt), another metal salt (e.g., an aluminum salt, an iron salt, a zinc salt, a copper salt, a nickel salt, a cobalt salt), an ammonium salt, a tetramethylammonium salt, an amine salt (e.g., a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tris(hydroxymethyl)aminomethane salt), an inorganic acid salt (e.g., a hydrofluoric acid salt, a hydrochloric acid salt, a hydrobromic acid salt, a hydroiodic acid salt, a nitric acid salt, a perchloric acid salt, a sulfuric acid salt, a phosphoric acid salt), an organic acid salt (e.g., a methanesulfonic acid salt, a trifluoromethanesulfonic acid salt, an ethanesulfonic acid salt, a benzenesulfonic acid salt, a p-toluenesulfonic acid salt, an acetic acid salt, a malic acid salt, a fumaric acid salt, a succinic acid salt, a citric acid salt, a tartaric acid salt, an oxalic acid salt, a maleic acid salt), and an amino acid salt (e.g., a glycine acid, a lysine acid, an arginine salt, an ornithine salt, a glutamic acid salt, an aspartic acid salt).

<<Method for Producing Compound (1)>>

The compound (1) can be produced by, for example, a reaction scheme 1 shown below.

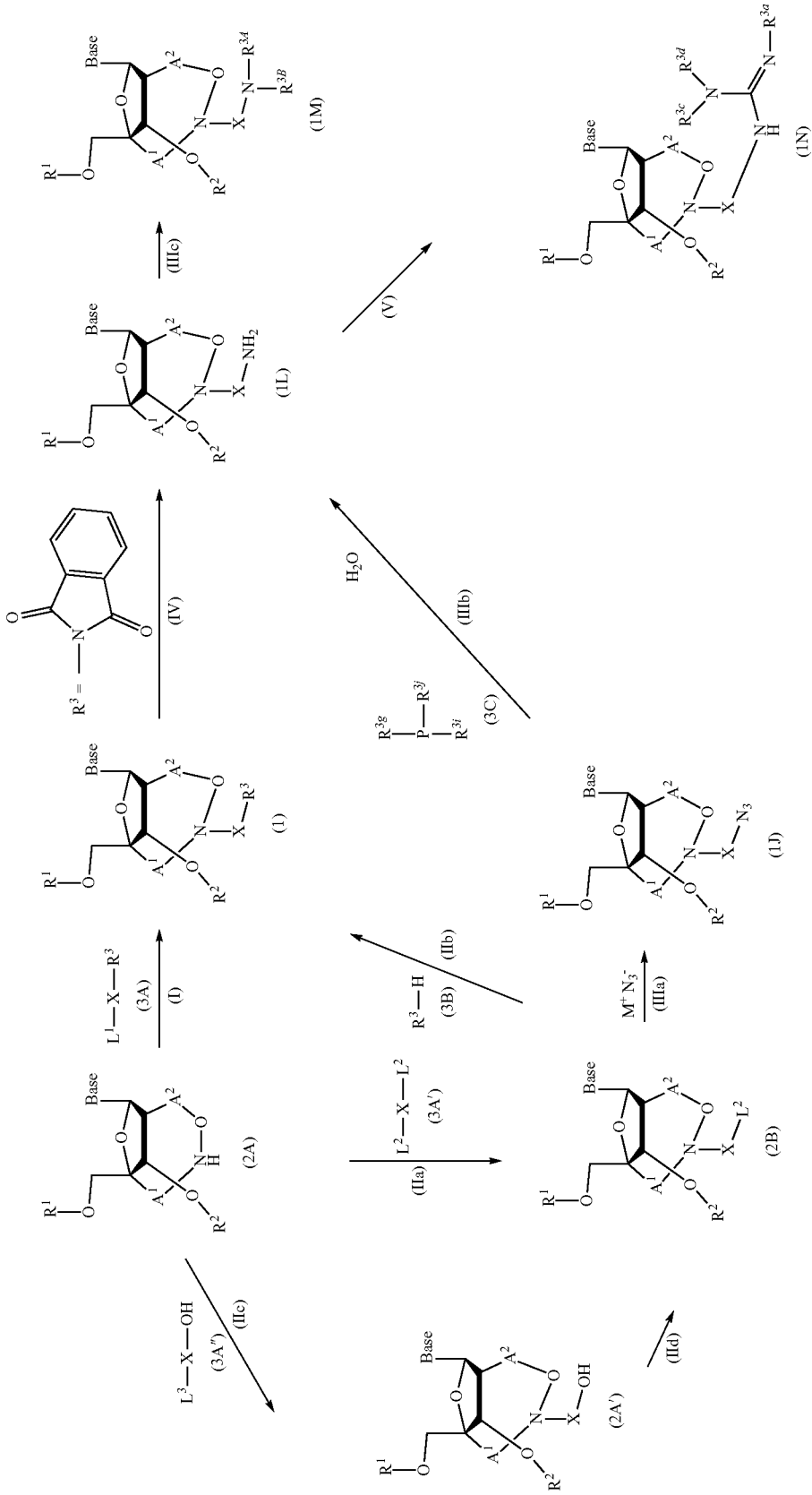

(wherein $L^1$, $L^2$'s and $L^3$ are the same as or different from each other and independently represent a leaving group; M represents an alkali metal or ammonium; $R^{3A}$ and $R^{3B}$ are the same as or different from each other and independently represent a hydrogen atom or a protecting group for an amino group (wherein a case where each of $R^{3A}$ and $R^{3B}$ represents a hydrogen atom is excluded); and "Base", $A^1$, $A^2$, X, $R^1$, $R^2$, $R^3$, $R^{3c}$ to $R^{3e}$ and $R^{3g}$ to $R^{3i}$ are as defined above.)

[Reaction Scheme 1]

<Step (I)>

Step (I) is a step of reacting a compound (2A) with a compound represented by the formula (3A): $L^1$-X—$R^3$ to produce a compound (1).

The compound (2A) can be produced by a known method, for example the method described in the description of US Patent Application Publication No. 2007/167387.

In the compound (3A), an example of the leaving group represented by $L^1$ is a halogen atom (e.g., a chlorine atom, a bromine atom, an iodine atom), an alkylsulfonyloxy group (e.g., a mesyloxy group), a haloalkylsulfonylocy group (e.g., a trifluoromethylsulfonyloxy group), or an arylsulfonylocy group (e.g., a tosylocy group).

The amount of the compound (3A) to be used is generally 1 to 10 moles, preferably 3 to 6 moles, relative to 1 mole of the compound (2A).

The reaction is preferably carried out in the presence of a solvent.

Examples of the solvent include an ether-type solvent (e.g., tetrahydrofuran), a nitrile-type solvent (e.g., acetonitrile), an aromatic hydrocarbon-type solvent (e.g., toluene, xylene), and a mixed solvent composed of two or more of these solvents. Among these solvents, an aromatic hydrocarbon-type solvent is preferred, and at least one solvent selected from the group consisting of toluene and xylene is more preferred.

The reaction is preferably carried out in the presence of a base.

Examples of the base include an inorganic base [e.g., a carbonate salt of an alkali metal (e.g., sodium carbonate, cesium carbonate), a hydrogen carbonate salt of an alkali metal (e.g., sodium hydrogen carbonate), a carbonate salt of an alkaline earth metal (e.g., calcium carbonate), a hydroxide of an alkali metal (e.g., sodium hydroxide, potassium hydroxide), a hydroxide of an alkaline earth metal (e.g., calcium hydroxide), a metal alkoxide (e.g., sodium methoxide, sodium ethoxide)], an organic base [e.g., a tertiary amine (e.g., trialkylamine), a cyclic amine (e.g., 4-(dimethylamino)pyridine, diazabicycloundecene (DBU), diazabicyclononene (DBN))], and a combination of two or more of these bases. Among these bases, a tertiary amine is preferred, and a tri-$C_{1-4}$-alkylamine is more preferred.

The amount of base to be used is generally 2 to 10 moles, preferably 5 to 8 moles, relative to 1 mole of the compound (2A).

The reaction temperature for the reaction is not particularly limited as long as the reaction can proceed, and is for example 30 to 150° C., preferably 50 to 120° C.

The reaction time for the reaction is not particularly limited, and is for example 1 to 24 hours, preferably 1 to 12 hours.

<Step (IIa)>

Step (IIa) is a step of reacting the compound (2A) with a compound represented by the formula (3A'): $L^2$-X-$L^2$ to produce a compound (2B).

In the compound (3A'), examples of the leaving group represented by $L^2$ are the same as those of $L^1$.

The amount of the compound (3A') to be used is generally 1 to 20 moles, preferably 1 to 5 moles, relative to 1 mole of the compound (2A).

As in the case of step (I), the reaction can be carried out in the presence of a solvent and/or a base.

<Step (IIb)>

Step (IIb) is a step of reacting the compound (2B) with a compound represented by the formula (3B): $R^3$—H to produce a compound (1).

The amount of the compound (3B) to be used is generally 1 to 20 moles, preferably 1 to 5 moles, relative to 1 mole of the compound (2B).

As in the case of step (I), the reaction can be carried out in the presence of a solvent and/or a base.

<Step (IIc)>

Step (IIc) is a step of reacting the compound (2A) with a compound represented by the formula (3A"): $L^3$-X—OH to produce a compound (2A').

The amount of the compound (3A") to be used is generally 1 to 20 moles, preferably 1 to 5 moles, relative to 1 mole of the compound (2A).

As in the case of step (I), the reaction can be carried out in the presence of a solvent and/or a base.

<Step (IId)>

Step (IId) is a step of converting the hydroxyl group in the compound (2A') to a leaving group $L^2$ to produce a compound (2B).

A typical example of step (IId) is a step of reacting the compound (2A') with a sulfonyl halide (e.g., an alkanesulfonic acid halide, a haloalkanesulfonic acid halide, an arenesulfonic acid halide). According to this step, the hydroxyl group in the compound (2A') can be converted to an alkylsulfonylocy group, a haloalkylsulfonylocy group, or an arylsulfonylocy group.

The amount of the sulfonyl halide to be used is generally 0.5 to 5 moles, preferably 1 to 2 moles, relative to 1 mole of the compound (2A').

As in the case of step (I), the reaction can be carried out in the presence of a solvent and/or a base.

<Step (IIIa)>

Step (IIIa) is a step of reacting the compound (2B) with an azide salt represented by the formula: $M^+N_3^-$ to produce a compound (1J).

Examples of the azide salt include sodium azide, potassium azide, and ammonium azide.

The amount of the azide salt to be used is generally 1 to 5 moles, preferably 1 to 2 moles, relative to 1 mole of the compound (2B).

The reaction is preferably carried out in the presence of a solvent.

Examples of the solvent include a nitrile-type solvent (e.g., acetonitrile), an ether-type solvent (e.g., tetrahydrofuran), an amide-type solvent (e.g., N,N-dimethylformamide, N,N-dimethylacetamide, N-methylpyrrolidone), and a mixed solvent composed of two or more of these solvents. Among these solvents, an amide-type solvent is preferred, and N,N-dimethylformamide is more preferred.

The reaction temperature for the reaction is not particularly limited as long as the reaction can proceed, and is for example 30 to 150° C., preferably 50 to 120° C.

<Step (IIIb)>

Step (IIIb) is a step of reacting the compound (1J) with a compound represented by the formula (3C:

[Formula 35]

(3C)

and then subjecting a resultant product to hydrolysis to produce a compound (1L).

In the compound (3C), each of $R^{3g}$ to $R^{3i}$ is preferably an aryl group, more preferably a $C_{6-10}$ aryl group.

The amount of the compound (3C) to be used is generally 1 to 10 moles, preferably 1 to 3 moles, relative to 1 mole of the compound (1J).

The reaction is preferably carried out in the presence of a solvent.

Examples of the solvent include a nitrile-type solvent (e.g., acetonitrile), an ether-type solvent (e.g., a cyclic ether such as tetrahydrofuran and dioxane), and a mixed solvent composed of two or more of these solvents. Among these solvents, an ether-type solvent is preferred, a cyclic ether is more preferred, and at least one solvent selected from tetrahydrofuran and dioxane is preferred.

The reaction temperature for the reaction is not particularly limited as long as the reaction can proceed, and is for example 15 to 30° C.

Alternatively, step (IIIb) may be a step of reducing the compound (1J) with a reducing agent (e.g., lithium aluminum hydride) to produce a compound (1L).

<Step (IIc)>

Step (IIIc) is a step of protecting an amino group in the compound (1L) by a protecting group for an amino group to produce a compound (1M).

As the method for protecting the amino group by a protecting group for an amino group, a known or conventional method can be employed. For example, the step of introducing a trifluoromethylcarbonyl group as a protecting group for an amino group in the compound (1L) is a step of reacting the compound (1L) with trifluoroacetic acid or a derivative thereof (e.g., trifluoroacetic anhydride). The reaction is preferably carried out in the presence of a solvent. A preferred example of the solvent is a cyclic amine (e.g., pyridine).

<Step (IV)>

Step (IV) is a step of producing a compound (1L) which is a compound (1) wherein $R^3$ is an amino group.

Step (IV) is a step of reacting a compound which is a compound (1) wherein $R^3$ is a phthalimide residue represented by the formula:

[Formula 36]

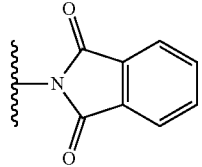

with a hydrazine compound (e.g., hydrazine monohydrate).

The amount of the hydrazine compound to be used is generally 1 to 10 moles, preferably 1.1 to 3.5 moles, relative to 1 mole of the compound which is a compound (1) wherein $R^3$ is a phthalimide residue.

The reaction is preferably carried out in the presence of a solvent.

Examples of the solvent include water, an alcohol-type solvent (e.g., methanol, ethanol), and a mixed solvent composed of two or more of these solvents. Among these solvents, an alcohol-type solvent is preferred.

Alternatively, step (IV) may be a step of hydrolyzing a compound which is a compound (1) wherein $R^3$ is a phthalimide residue.

<Step (V)>

Step (V) is a step of guanidinylating the compound (1L) and optionally protecting an amino group by a protecting group to produce a compound (1N).

The guanidinylation is generally carried out by the reaction with a guanidinylating agent. Examples of the guanidinylating agent include a nitrogen-based guanidinylating agent and a sulfur-based guanidinylating agent.

Examples of the nitrogen-based guanidinylating agent include compounds represented by the following formulae:

[Formula 37]

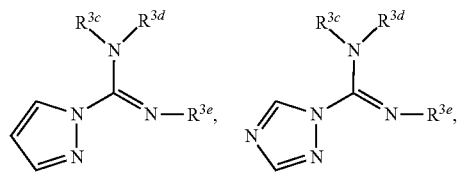

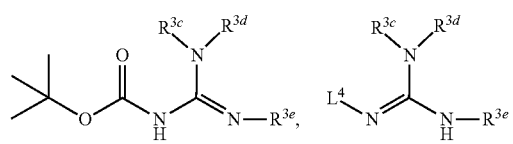

(wherein $L^4$ represents a leaving group; and $R^{3c}$ to $R^{3e}$ are as defined above).

Examples of the leaving group represented by $L^4$ are the same as those of $L^1$.

The nitrogen-based guanidinylating agent is preferably 1-amidinopyrazole hydrochloride, 1-carbamimidoyl-1,2,4-triazole hydrochloride, 1-(N-t-butoxy-amidino)pyrazole, 1-(N-benzyloxy-amidino)pyrazole, 1-[N,N'-(di-t-butoxy)amidino]pyrazole, 1-[N,N'-(di-benzyloxy)amidino]pyrazole, 1,2,3-tris(t-butoxycarbonyl)guanidine, or Goodman's reagent.

Examples of the sulfur-based guanidinylating agent include compounds represented by the following formulae:

[Formula 38]

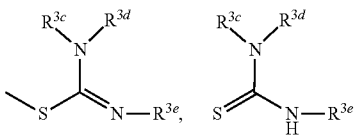

(wherein $R^{3c}$ to $R^{3e}$ are as defined above).

The sulfur-based guanidinylating agent is preferably N,N'-di-t-butoxy-S-methylisothiourea, or 1,3-di-t-butoxythiourea.

The amount of the guanidinylating agent to be used is generally 0.5 to 10 moles, preferably 0.8 to 2.0 moles, relative to 1 mole of the compound (1L).

The reaction of the compound (1L) with the guanidinylating agent is preferably carried out in the presence of a solvent.

Examples of the solvent include a halogenated hydrocarbon-type solvent (e.g., dichloromethane), an amide-type solvent (e.g., N,N-dimethylformamide, N,N-dimethylacetamide, N-methylpyrrolidone), and a mixed solvent composed of two or more of these solvents. Among these solvents, an amide-type solvent is preferred, and N,N-dimethylformamide is more preferred.

The reaction temperature for the reaction is not particularly limited as long as the reaction can proceed, and is for example 15 to 30° C.

The method for producing a compound which is a compound (1N) wherein $R^{3c}$ to $R^{3e}$ independently represent a hydrogen atom or a salt thereof may be a method comprising a step of reacting the compound (1L) with a 2-halo-4,6-dialkoxypyrimidine represented by the following formula:

[Formula 39]

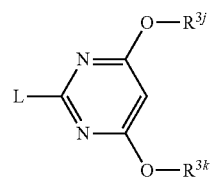

(wherein L represents a halogen atom; and $R^{3j}$ and $R^{3k}$ are the same as or different from each other and independently represent an alkyl group)

to produce a compound represented by formula (1L'):

[Formula 40]

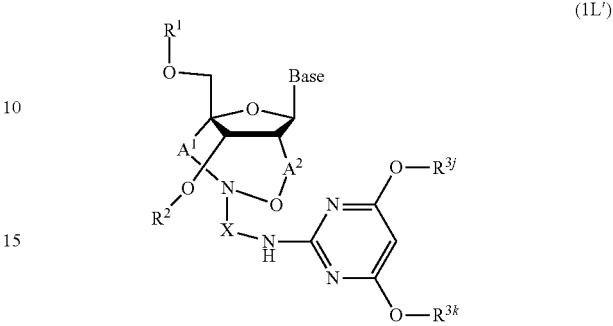

(wherein $R^{3j}$ and $R^{3k}$ are as defined above)

and a step of cleaving (or hydrolyzing) a pyrimidine ring in the compound (1L').

With respect to details about this method, see, for example, Tetrahedron Letters, 56, 2015, pp. 4990 to 4992.

The method for producing a compound which is a compound (1N) wherein $R^{3c}$ to $R^{3e}$ independently represent a hydrogen atom or a salt thereof may be a method comprising a step of reacting the compound (1L) with O-methylisourea.

With respect to details about this method, see, for example, Anal Chem., 85(18), 2013, pp. 1 to 17.

The method for producing a compound which is a compound (1N) wherein $R^{3c}$ and $R^{3d}$ independently represent a hydrogen atom and $R^{3e}$ represents a benzyloxycarbonyl group or a salt thereof may be a method comprising a step of reacting the compound (1L) with a compound represented by the following formula:

[Formula 41]

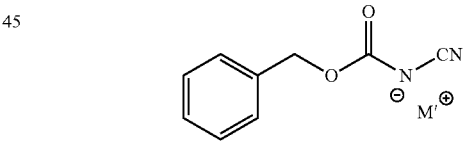

(wherein M' represents an alkali metal)

and a trialkylsilyl chloride (e.g., a tri-$C_{1-4}$-alkylsilyl chloride such as trimethylsilyl chloride).

With respect to details about this method, see, for example, J. Org. Chem., 76, 2011, pp. 6967 to 6971.

A benzyloxycarbonyl group may be deprotected from the compound produced by this method wherein $R^{3e}$ represents a benzyloxycarbonyl group by a conventional method to produce a compound wherein $R^{3e}$ represents a hydrogen atom.

The "Base" in each of the compounds (1), (1J), (1L), (1M), (1N), (2A), (2A') and (2B) can be converted by, for example, a reaction scheme 2 shown below.

Scheme 2

[Formula 42]

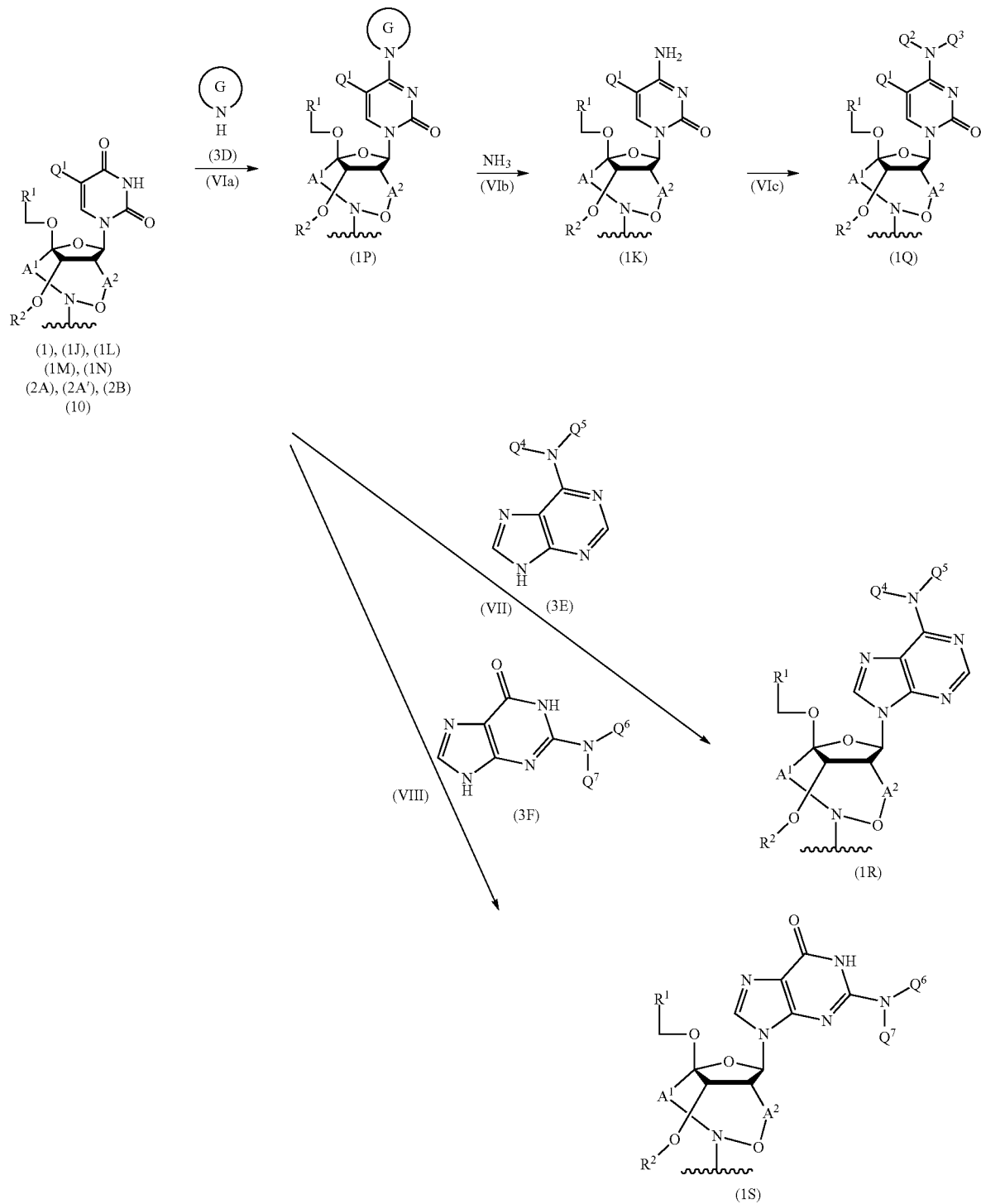

(wherein $Q^1$ represents a hydrogen atom or a substituent; $Q^2$ and $Q^3$ are the same as or different from each other and independently represent a hydrogen atom or a protecting group for an amino group (provided that a case where each of $Q^2$ and $Q^3$ represents a hydrogen atom is excluded); $Q^4$ to $Q^7$ are the same as or different from each other and independently represent a hydrogen atom or a protecting group for an amino group; the ring G represents a 5- or 6-membered nitrogenated heterocyclic ring; and $A^1$, $A^2$, $R^1$, and $R^2$ are as defined above.)

[Reaction Scheme 2]

<Step (VI)>

Step (VI) is a step of converting the "Base" from "a 2,4-dioxo-1,2,3,4-tetrahydropyrimidin-1-yl group which may have a substituent" to "a 2-oxo-1,2-dihydropyrimidin-1-yl group which may have a substituent" in each of the compounds (1), (1J), (1L), (1M), (1N), (2A), (2A'), and (2B), and includes step (VIa) to step (VIc).

<Step (VIa)>

Step (VIa) is a step of reacting a compound (1O) wherein "Base" represents "a 2,4-dioxo-1,2,3,4-tetrahydropyrimidin-1-yl group which may have a substituent" with a compound represented by formula (3D) and a phosphoric acid halide to produce a compound (1P).

In the compound (1O), $Q^1$ is preferably a hydrogen atom or an alkyl group, more preferably a hydrogen atom or a $C_{1-4}$ alkyl group.

The compound (3D) is preferably a 5-membered nitrogenated heterocyclic ring compound, more preferably triazole.

The amount of the compound (3D) to be used is generally 5 to 20 moles, preferably 7 to 9 moles, relative to 1 mole of the compound (1O).

The phosphoric acid halide is preferably phosphoric trichloride.

The amount of the phosphoric acid halide to be used is generally 1 to 5 moles, preferably 1 to 3 moles, relative to 1 mole of the compound (1O).

The reaction is preferably carried out in the presence of a solvent.

Examples of the solvent include a nitrile-type solvent (e.g., acetonitrile), an ether-type solvent (e.g., tetrahydrofuran), a halogen-based solvent (e.g., a haloalkane), and a mixed solvent composed of two or more of these solvents. Among these solvents, a nitrile-type solvent (e.g., acetonitrile) is preferred.

The reaction is preferably carried out in the presence of a base.

Examples of the base include an inorganic base [e.g., a carbonate salt of an alkali metal (e.g., sodium carbonate, cesium carbonate), a hydrogen carbonate salt of an alkali metal (e.g., sodium hydrogen carbonate), a carbonate salt of an alkaline earth metal (e.g., calcium carbonate), a hydroxide of an alkali metal (e.g., sodium hydroxide, potassium hydroxide), a hydroxide of an alkaline earth metal (e.g., calcium hydroxide), a metal alkoxide (e.g., sodium methoxide, sodium ethoxide)], an organic base [e.g., a tertiary amine (e.g., trialkylamine), a cyclic amine (e.g., 4-(dimethylamino)pyridine, diazabicycloundecene (DBU), diazabicyclononene (DBN))], and a combination of two or more of these bases. Among these bases, a tertiary amine is preferred, and a tri-$C_{1-4}$-alkylamine is more preferred.

The amount of the base to be used is generally 5 to 20 moles, preferably 10 to 15 moles, relative to 1 mole of the compound (1O).

The reaction temperature for the reaction is not particularly limited as long as the reaction can proceed, and is for example −5° C. to 10° C.

For example, as the reaction, the method described in the description of U.S. Pat. No. 5,359,067 may be employed.

<Step (VIb)>

Step (VIb) is a step of reacting the compound (1P) with ammonia to produce a compound (1K).

The amount of ammonia to be used is generally 5 to 100 moles, preferably 20 to 50 moles, relative to 1 mole of the compound (1P).

The reaction is preferably carried out in the presence of a solvent.

Examples of the solvent include an amide-type solvent (e.g., N,N-dimethylformamide, N,N-dimethylacetamide, N-methylpyrrolidone), an ether-type solvent (e.g., a cyclic ether such as tetrahydrofuran and dioxane), and a mixed solvent composed of two or more of these solvents. Among these solvents, an ether-type solvent is preferred, and a cyclic ether is more preferred, and at least one solvent selected from tetrahydrofuran and dioxane is still more preferred.

The reaction temperature for the reaction is not particularly limited as long as the reaction can proceed, and is for example 15 to −30° C.

<Step (VIc)>

Step (VIc) is a step of protecting an amino group in the compound (1K) by a protecting group to produce a compound (1Q). As the method for protecting the amino group by the protecting group, a known method (for example, the method described in the description of US Patent Application Publication No. 2007/167387) or a conventional method may be employed.

<Step (VII)>

Step (VII) is a step of converting the "Base" from "a 2,4-dioxo-1,2,3,4-tetrahydropyrimidin-1-yl group which may have a substituent" to "a purin-9-yl group which may have a substituent" in each of the compounds (1), (1J), (1L), (1M), (1N), (2A), (2A'), and (2B).

More specifically, step (VII) is a step of reacting the compound (1O) wherein "Base" is "a 2,4-dioxo-1,2,3,4-tetrahydropyrimidin-1-yl group which may have a substituent" with a compound represented by formula (3E) to produce a compound (1R).

The amount of the compound (3E) to be used is generally 1 to 5 moles, preferably 1 to 3 moles, relative to 1 mole of the compound (1O).

The reaction is preferably carried out in the presence of a Lewis acid.

An example of the Lewis acid is trimethylsilyl trifluoromethanesulfonate.

The amount of the Lewis acid to be used is generally 0.5 to 5 moles, preferably 1 to 3 moles, relative to 1 mole of the compound (1O).

The reaction is preferably carried out in the presence of a silylating agent.

Examples of the silylating agent include N,O-bis(trimethylsilyl)acetamide (BSA), N,O-bis-silyltrifluoroacetamide (BSTFA), hexamethyldisilazane (HMD), N,O-bis-tert-butyldimethylsilylacetamide, N-(trimethylsilyl)diethylamine, N-(trimethylsilyl)dimethylamine, N-methoxy-N,O-bis(trimethylsilylL)carbamate, N-methyl-N-trimethylsilylacetamide, N-methyl-N-trimethylsilylheptafluorobutyramide, N-methyl-N-trimethylsilyltrifluoroacetamide, N-trimethylsilylacetamide, and a combination of two or more of these compounds. Among these compounds, N,O-bis(trimethylsilyl)acetamide (BSA) is preferred.

The amount of the silylating agent to be used is generally 1 to 20 moles, preferably 3 to 8 moles, relative to 1 mole of the compound (1O).

The reaction temperature for the reaction is not particularly limited as long as the reaction can proceed, and is for example 30 to 150° C., preferably 50 to 120° C.

For example, tor the reaction, the method described in the description of US Patent Application Publication No. 2012/071646 may be employed.

<Step (VIII)>

Step (VIII) is a step of converting "Base" from "a 2,4-dioxo-1,2,3,4-tetrahydropyrimidin-1-yl group which may have a substituent" to "a 6-oxo-1,6-dihydro-9H-purin-9-yl group which may have a substituent" in each of the compounds (1), (1J), (1L), (1M), (1N), (2A), (2A'), and (2B). More specifically, step (VIII) is a step of reacting a compound wherein "Base" is "a 2,4-dioxo-1,2,3,4-tetrahydropyrimidin-1-yl group which may have a substituent" with a compound represented by formula (3F) to produce a compound (1S).

More specifically, step (VIII) is a step of reacting the compound wherein "Base" is "a 2,4-dioxo-1,2,3,4-tetrahydropyrimidin-1-yl group which may have a substituent" with a compound represented by formula (3F) to produce a compound (1S).

The reaction can be carried out under the same conditions as those employed for step (VII).

If necessary, the method for producing the compound (1) may further include a step of purifying an intermediate product and a final product by a conventional method, such as concentration, recrystallization and silica gel column chromatography.

<<Composition Containing Compound (1)>>

The composition according to the present invention contains the above-mentioned compound (1).

The composition may contain one compound (1) or two or more compounds (1). For example, the composition may contain one, two, three or four compounds selected from the group consisting of:

a compound (1) wherein "Base" is a thymin-1-yl group;

a compound (1) wherein "Base" is a 5-methylcytosin-1-yl group, an N-acetyl-5-methylcytosin-1-yl group, an N-isobutyryl-5-methylcytosin-1-yl group, or an N-benzoyl-5-methylcytosin-1-yl group;

a compound (1) wherein "Base" is an adenin-9-yl group, an N-acetyl-adenin-9-yl group, an N-isobutyryl-adenin-9-yl group, or an N-benzoyl-adenin-9-yl group; and a compound (1) wherein "Base" is a guanin-9-yl group, an N-acetyl-guanin-9-yl group, an N-isobutyrylguanin-9-yl group, an N-benzoyl-guanin-9-yl group, or an N-(N, N-dimethylformamidyl)-guanin-9-yl group.

An example of the form of the composition is a liquid form.

When the composition has a liquid form, the composition generally contains a solvent. As the solvent, a known solvent can be used, and preferred examples of the solvent include a halogenated hydrocarbon-type solvent (e.g., dichloromethane), a nitrile-type solvent (e.g., acetonitrile), an aromatic hydrocarbon-type solvent (e.g., toluene, xylene), water, and a TE buffer. Among these solvents, dichloromethane, toluene, and acetonitrile are more preferred.

The composition is generally provided to a user in a form packed in a container.

The composition can be used for the below-mentioned synthesis of an oligonucleotide or a salt thereof. The composition can also be used as a pharmaceutical composition.

<<Oligonucleotide or Salt Thereof>>

The oligonucleotide or a salt thereof according to the present invention has a unit represented by formula (4):

[Formula 43]

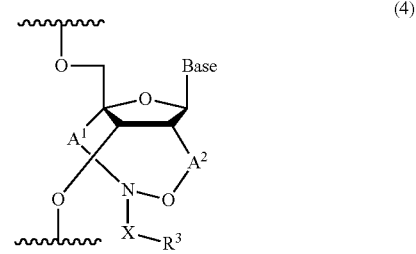

(4)

(wherein "Base", $A^1$, $A^2$, X, and $R^3$ are as defined above).

The unit is preferably a unit represented by formula (4a):

[Formula 44]

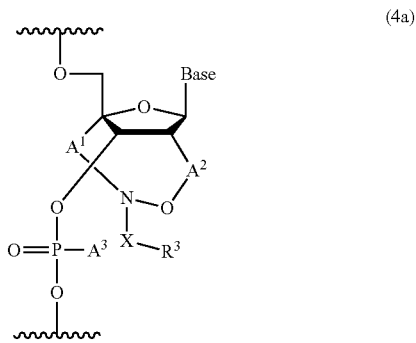

(4a)

(wherein $A^3$ represents OH or SH; and "Base", $A^1$, $A^2$, X, and $R^3$ are as defined above).

Hereinbelow, an oligonucleotide having a unit represented by formula (4) or (4a) or a salt thereof is referred to as an "oligonucleotide (4)".

When the oligonucleotide (4) has at least two units represented by formula (4) or (4a), the structures of the units may be the same as or different from each other.

The oligonucleotide (4) may further contain another unit, in addition to the unit represented by formula (4) or (4a).

An example of the other unit is at least one unit selected from units respectively represented by formulae (5) to (8):

[Formula 45]

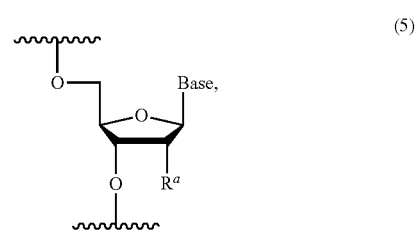

(5)

-continued (6)
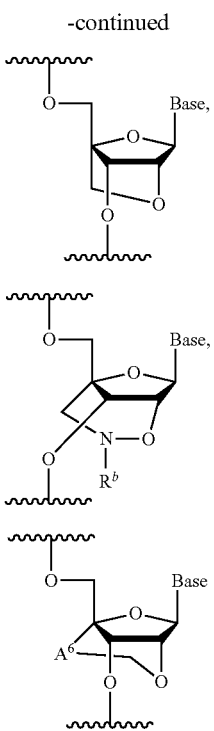

(7)

(8)

(wherein $A^6$'s are the same as or different from each other and independently represent a single bond or an alkylene group which may have a substituent; $R^a$ represents a hydrogen atom or a hydroxyl group; $R^b$ represents a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group; and "Base" is as defined above).

The other unit is preferably at least one unit selected from units respectively represented by formulae (5a) to (8a):

[Formula 46]

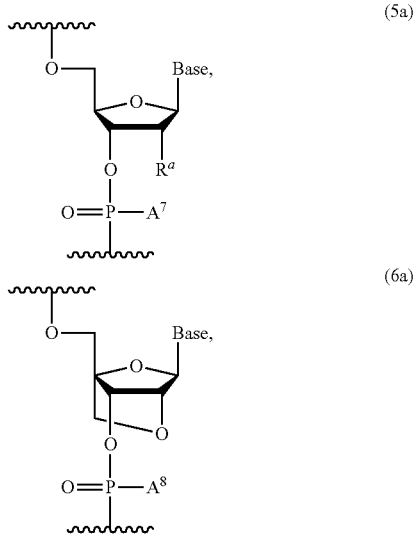

(5a)

(6a)

-continued (7a)

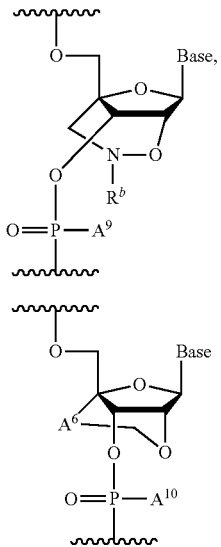

(8a)

(wherein $A^7$ to $A^{10}$ are the same as or different from each other and independently represent OH or SH; and "Base" and $A^6$ are as defined above).

For example, the other unit may be a unit derived from any one of the nucleotides described in the descriptions of US Patent Application Publication No. 2003/105309, US Patent Application Publication No. 2017/044528, US Patent Application Publication No. 2006/166908, US Patent Application Publication No. 2012/208991, US Patent Application Publication No. 2015/266917, and US Patent Application Publication No. 2003/207841.

The nucleotide sequence for the oligonucleotide (4) is not particularly limited, as long as the nucleotide sequence is complementary to (the full length or a part of) the nucleotide sequence for target DNA or target RNA.

The length of the oligonucleotide (4) is not particularly limited, and can be selected depending on the length of the nucleotide sequence for a target. The lower limit of the length of the oligonucleotide (4) is, for example 5-mer, preferably 10-mer, more preferably 15-mer, and the upper limit of the length of the oligonucleotide (4) is, for example 200-mer, preferably 100-mer, more preferably 50-mer, still more preferably 30-mer. The length of the oligonucleotide (4) is, for example 5- to 200-mer, preferably 5- to 50-mer, more preferably 10- to 40-mer, more preferably 15- to 30-mer. The binding force of the oligonucleotide (4) to the nucleotide sequence for a target becomes stronger with the increase in the length of the oligonucleotide (4).

In the oligonucleotide (4), the ratio of the number of units represented by formula (4) to the total number of nucleotide units is not particularly limited, and can be designed appropriately depending on the intended use (e.g., as a primer, a probe, a clamp nucleic acid, a medicine).

The oligonucleotide (4) may be in the form of a salt. In other words, at least one nucleotide unit among the nucleotide units constituting the oligonucleotide (4) may be in the form of a salt. The salt may be a pharmaceutically acceptable salt or may not be a pharmaceutically acceptable salt. The salt may be an inorganic salt or an organic salt. As in the case of the salt exemplified for the compound (1), examples of the salt include an alkali metal salt, an alkaline earth metal salt, another metal salt, an ammonium salt, a tetramethylammonium salt, an amine salt, an inorganic acid salt, an organic acid salt, and an amino acid salt.

The oligonucleotide (4) may be modified with a labeling substance. The labeling substance is not particularly limited, and may be a substance known in the art as a label to be attached to a nucleic acid, such as a fluorescent substance, a hapten (e.g., biotin, digoxigenin, DNP), and a radioisotope.

The oligonucleotide (4) has high sequence-specificity.

With respect to the oligonucleotide (4), a Tm value which indicates a capability of forming a double strand with single-stranded RNA is higher than that of DNA having the same "Base" (formula (5) wherein $R^a$=H).

With respect to the oligonucleotide (4), a Tm value which indicates a capability of forming a double strand with single-stranded DNA is also higher than that of DNA having the same "Base" (formula (5) wherein $R^a$=H).

The oligonucleotide (4) can have high capability of forming a double strand not only with single-stranded RNA but also with single-stranded DNA. In this respect, the oligonucleotide (4) is superior to the conventional oligonucleotides. The oligonucleotide (4) can be utilized suitably as a probe for examining the nucleotide sequence for single-stranded RNA or single-stranded DNA or for detecting single-stranded RNA or single-stranded DNA in a highly sequence-selective manner.

The oligonucleotide (4) is less likely to be decomposed with a nuclease, and therefore can exist in a living body for a long period after the administration to the living body. For example, the oligonucleotide (4) can form a double strand with sense RNA to inhibit the transcription of mRNA for a biological component (a protein) that may act as a causal factor of a disease. The oligonucleotide (4) can also inhibit the proliferation of a virus that has infected.

The oligonucleotide (4) is useful as a medicine, e.g., an anti-tumor agent and anti-viral agent, which can inhibit the activity of a gene to treat a disease.

The oligonucleotide (4) also has a stable and excellent activity for use as an antisense or anti-gene or an aptamer, or has an excellent activity for use as a detecting drug for a specific gene or a primer for the initiation of the amplification of a specific gene.

The oligonucleotide (4) is useful as a physiological/bioactive substance, a material for a medicine, a functional material for a double-stranded oligonucleotide for use in an RNA interference method, a decoy method or the like, a functional material such as a DNA chip that targets a single-stranded nucleic acid (e.g., cDNA), a molecular beacon or the like, a functional material for use in various antisense methods (including a ribozyme or a DNA-zyme), anti-gene methods or genetic homologous recombination methods, a material which can be used in combination with a fluorescence or a light-emitting substance in a highly sensitive analysis of a biological trace component, or a material for use in the development of a reagent for research use (e.g., the elucidation of the function of a gene).

<<Method for Producing Oligonucleotide (4)>>

The oligonucleotide (4) can be synthesized in accordance with a conventional method such as a phosphoramidite protocol.

For example, the method for producing the oligonucleotide (4) includes:

(I) a step of reacting a compound represented by formula (4A):

[Formula 47]

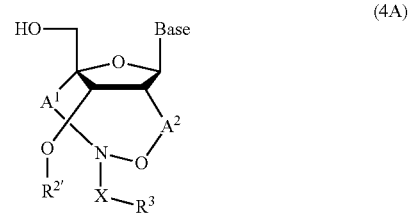

(4A)

(wherein $R^{2'}$ represents an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent; and "Base", $A^1$, $A^2$, X, and $R^3$ are as defined above)

or a salt thereof with at least one compound selected from compounds respectively represented by formulae (4B) to (8B):

[Formula 48]

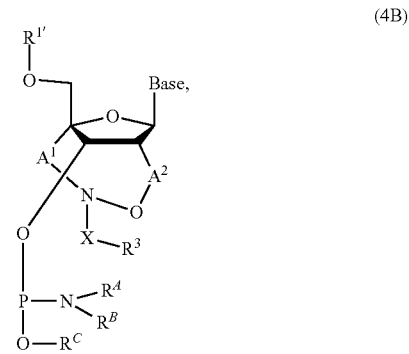

(4B)

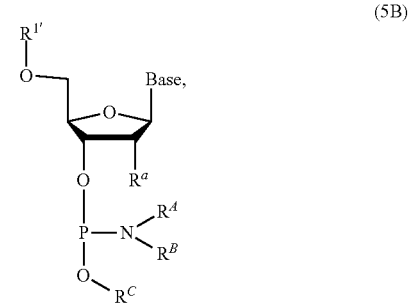

(5B)

-continued

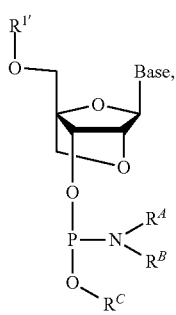 (6B)

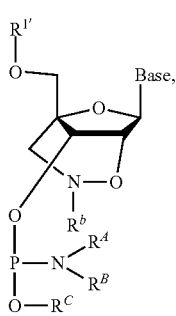 (7B)

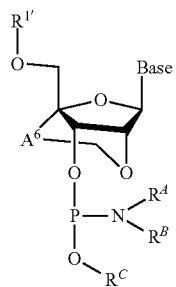 (8B)

(wherein
R$^{1'}$ represents a hydrogen atom, an alkyl group which may have a substituent, an alkenyl group which may have a substituent, a cycloalkyl group which may have a substituent, a cycloalkenyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent;

R$^A$ and R$^B$ are the same as or different from each other and independently represent a hydrogen atom or an alkyl group;

R$^C$ represents a hydrogen atom, an alkyl group, a haloalkyl group, or a cyanoalkyl group; and "Base", A$^1$, A$^2$, A$^6$, X, R$^3$, R$^a$, and R$^b$ are as defined above)

or salts thereof; and/or (II) a step of reacting a compound represented by formula (4B):

[Formula 49]

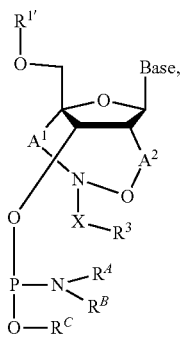 (4B)

(wherein "Base", A$^1$, A$^2$, X, R$^{1'}$, R$^3$, R$^A$, R$^B$, and R$^C$ are as defined above)

or a salt thereof with at least one compound selected from compounds respectively represented by formulae (4A) to (8A):

[Formula 50]

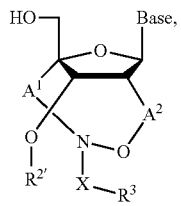 (4A)

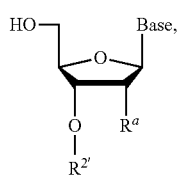 (5A)

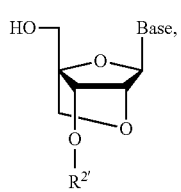 (6A)

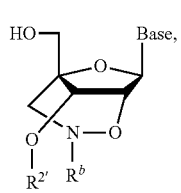 (7A)

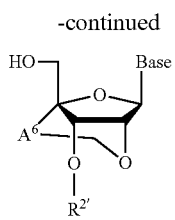

(8A)

(wherein "Base", $A^1$, $A^2$, $A^6$, X, $R^{2'}$, $R^3$, $R^a$, and $R^b$ are as defined above)

or salts thereof; and (III) a step of oxidizing (particularly oxidizing a phosphorus atom in) the compound produced in step (I) and/or step (II).

If necessary, the method for producing the oligonucleotide (4) optionally includes a step of purifying the intermediate product and the final product by a conventional method, e.g., concentration, recrystallization, silica gel column chromatography, gel filtration, ethanol precipitation, preparative HPLC.

<<Composition Containing Oligonucleotide (4)>>

The composition according to the present invention contains the above-mentioned oligonucleotide (4).

The composition may contain only one oligonucleotide (4) or may contain two or more oligonucleotides (4).

Examples of the form of the composition include a liquid form and a solid form.

When the composition has a liquid form, the composition generally contains a solvent. As the solvent, a known solvent can be used, and preferably a halogenated hydrocarbon-type solvent (e.g., dichloromethane), a nitrile-type solvent (e.g., acetonitrile), an aromatic hydrocarbon-type solvent (e.g., toluene, xylene) or water is used. Among these solvents, water is more preferred, water containing a buffer (a buffer solution) is more preferred. Examples of the buffer include tris(hydroxymethyl)aminomethane (Tris buffer solution), tris(hydroxymethyl)aminomethane-hydrochloric acid (Tris-HCl buffer solution), tris(hydroxymethyl)aminomethane-EDTA (TE buffer solution), sodium phosphate, 2-morpholinoethanesulfonic acid (MES), N-(2-acetamido) iminodiacetic acid (ADA), piperazine-1,4-bis(2-ethanesulfonic acid), N-(2-acetamido)-2-aminoethanesulfonic acid (ACES), cholamine chloride, N,N-bis(2-hydroxyethyl)-2-aminoethanesulfonic acid (BES), N-tris(hydroxymethyl)methyl-2-aminoethanesulfonic acid (TES), 2-[4-(2-hydroxyethyl)-1-piperazinyl]ethanesulfonic acid (HEPES), acetaminoglycine, tricine, glycinamide, and bicine.

The composition may further contain a salt. The salt includes a metal chloride, and examples of the metal chloride include NaCl, $MgCl_2$, and KCl.

The composition may further contain an additive and a co-solvent. For example, dimethyl sulfoxide (DMSO), glycerol, formamide, bovine serum albumin, ammonium sulfate, polyethylene glycol (PEG), gelatin, and a nonionic surfactant may be contained. Examples of the nonionic surfactant include Tween20 (registered trademark) and Triton X-100 (registered trademark).

When the composition has a solid form, the composition may have, for example, such a form that the oligonucleotide (4) is supported on a solid support. Examples of the solid support include an inorganic material and an organic material which can support a biopolymer. Preferred examples include a glass (e.g., a porous glass (a CPG)), silica gel, and a resin (e.g., a crosslinked non-swellable polystyrene resin (a HPS)). Among these materials, a HPS and a CPG is more preferred.

The composition is generally provided to a user in a form packed in a container.

The composition can be used for the detection of a target nucleic acid, strand invasion and the like as mentioned below. The composition can also be used as a pharmaceutical composition.

<<Method for Detecting Target Nucleic Acid in Test Specimen>>

The present invention includes a method for detecting a target nucleic acid in a test specimen. The method includes:

(I) a step of selectively amplifying a nucleotide sequence containing a target site in the target nucleic acid (including the full-length nucleotide sequence for the target nucleic acid) by a nucleic acid amplification method using a clamp nucleic acid, in which the clamp nucleic acid is the oligonucleotide (4); and (II) a step of detecting the amplified nucleotide sequence.

The test specimen is not particularly limited, as long as a nucleic acid is contained. The test specimen is typically a specimen collected from a living body. In general, a specimen produced by a pre-treatment such as the removal of contaminants from a specimen collected from a living body, the extraction/purification of nucleic acid and pre-amplification is used. More specifically, blood, plasma, serum, pleural effusion, a broncho-alveolar lavage fluid, bone marrow fluid, lymphatic fluid, urine, stool, a bowel lavage fluid, and an excised tissue can be used. Alternatively, a specimen obtained by subjecting the above-mentioned specimen to a pretreatment can also be used. The method according to the present invention can detect a mutation in a nucleic acid with very high sensitivity. Therefore, it is possible to use a solid specimen (e.g., cancer) directly collected from a lesion or to use a liquid specimen (e.g., blood) in which a specimen to be detected is contained in a trace amount. The test specimen is preferably a solution containing a target nucleic acid. When it is intended to detect a target nucleic acid in a cell contained in blood or an excised tissue, the cell may be lysed by a known method.

The target nucleic acid may be DNA or RNA, and is preferably DNA. The target nucleic acid may be a gene or a specific region on genomic DNA (e.g., a promoter region in a gene). The detection method according to the present invention can be used for the detection of a mutation in a target site, the detection of polymorphism or the like. The detection method according to the present invention can also be used for the determination of an allele. It also becomes possible to detect as to what type of an allele is contained in a test specimen. The detection method according to the present invention can also be used for the detection of methylation. When the detection method according to the present invention is applied after a bisulphite treatment of a target nucleic acid, the presence or absence of methylated cytosine in the target nucleic acid can be detected.

A gene containing a mutation (hereinafter, also referred to as a "mutant gene") has a difference in nucleotide sequence from a wild-type gene, i.e., a mutation. The difference is caused by at least one mutation selected from the group consisting of substitution, insertion, deletion, inversion, duplication and translocation or a combination thereof.

In general, the difference is often associated with the onset (development) and/or therapeutic sensitivity of a specific disease. The term "onset (development)" includes the actual onset (development) of a disease as well as the risk of onset (development) and the like. The term "therapeutic sensitivity" includes the efficacy of a treatment with a drug or the like as well as the level of an adverse side effect. Examples of the disease include, but are not limited to, cancer, a myelodysplastic syndrome and an infectious disease. A preferred example of the disease is cancer.

A preferred example of the gene is ABL/BCR fusion gene, HER2 gene, EGFR gene, c-KIT gene, KRAS gene, BRAF gene, PIK3CA gene, FLT3 gene, MYC gene, MYCN gene, MET gene, BCL2 gene, or EML4/ALK fusion gene.

In general, a clamp nucleic acid can clamp a non-target nucleic acid (e.g., a wild-type gene) in a test specimen stronger compared with a target nucleic acid (e.g., a mutant gene) in a test specimen. A target nucleic acid can be amplified selectively by binding a clamp nucleic acid to a non-target nucleic acid stronger to inhibit the amplification of the non-target nucleic acid. For example, for the detection of a mutation in a specific gene, the amplification of a nucleic acid is carried out in the presence of a clamp nucleic acid having a nucleotide sequence absolutely complementary to that of a wild-type gene. As a result, the amplification of the wild-type nucleic acid is inhibited, while the mutant nucleic acid is amplified selectively.

More specifically, for example, when a target site in a target nucleic acid is defined as a mutating site in a mutant gene and a nucleotide sequence containing the mutating site (the target site in the target nucleic acid) is defined as "sequence A", a clamp nucleic acid is absolutely complementary to a nucleotide sequence corresponding to the sequence A in a wild-type gene that is a non-target nucleic acid.

The oligonucleotide (4) has high sequence-selectivity. Therefore, the binding capability of the clamp nucleic acid to a nucleotide sequence having even one base different from the clamp nucleic acid is extremely weak, and can bind to an absolutely complementary nucleotide sequence specifically. The oligonucleotide (4) has a high Tm value, and therefore can form a stable double strand. That is, the clamp nucleic acid can strongly bind to a non-target nucleic acid specifically to exhibit a high clamping capability.

The length of the clamp nucleic acid is not particularly limited, and is for example 5- to 30-mer.

The nucleic acid amplification method is not particularly limited, as long as the target site can be amplified and this amplification can be inhibited selectively by the binding of the clamp nucleic acid. Examples of the nucleic acid amplification method include a PCR method (including, e.g., a hot-start PCR method, a multiplex PCR method, a nested PCR method, a RT-PCR method, a real-time PCR method, a digital PCR method), a NASBA method (see the description of U.S. Pat. No. 5,130,238), a TMA method (see the description of U.S. Pat. No. 5,399,491), a TRC method (see the description of US Patent Application Publication No. 2001/0053518), a LAMP method (see the description of U.S. Pat. No. 6,410,278), an ICAN method (see the description of US Patent Application Publication No. 2003/073081), a LCR method (see the description of EP Patent Application No. 320328), and a SDA method (see the description of U.S. Pat. No. 5,455,166).

As the method for detecting the amplified target nucleic acid, any method can be employed.

A preferred example of the detection method is a method using a detection probe that is a single-stranded nucleic acid having a nucleotide sequence complementary to a nucleotide sequence containing a target site in a target nucleic acid (e.g., a mutating site in a mutant gene). Specific examples of the method include a southern hybridization method, a TaqMan™ probe method, and a cycling probe method.

A preferred example of the detection probe is a hydrolysis probe in which one terminal (generally 5'-terminal) is labeled with a fluorescent group (reporter) and the other terminal (generally 3'-terminal) is labeled with a quenching group. In the case where this probe is used, when an extension reaction with a DNA polymerase proceeds in PCR, a fluorescent probe is hydrolyzed due to the exonuclease activity and, as a result, a reporter dye is released, resulting in the emission of fluorescence. The nucleic acid can be quantified by monitoring the intensity of the fluorescence.

As a method for detecting the amplified target nucleic acid, a nucleotide sequence analysis method is exemplified. The target nucleic acid can be detected by analyzing the nucleotide sequence of the amplified target nucleic acid using a known sequence analysis device (sequencer).

For example, as the method for detecting the target nucleic acid in a test specimen, the method described in the description of US Patent Application Publication No. 2015/240299 may be employed.

As mentioned above, the target nucleic acid in the test specimen can be detected with high sequence selectivity by using the oligonucleotide (4).

<<Composition and Kit for Detecting Target Nucleic Acid in Test Specimen or for Selectively Amplifying Nucleotide Sequence Containing Target Site in Target Nucleic Acid in Test Specimen>>

A composition for detecting a target nucleic acid in a test specimen or for selectively amplifying a nucleotide sequence containing a target site in a target nucleic acid in a test specimen (hereinafter, also referred to as a "test composition") contains the oligonucleotide (4). In general, the oligonucleotide (4) is included in a kit in the form of a composition.

In the test composition, the oligonucleotide (4) can be used as a primer, a probe and/or a clamp nucleic acid for use in the detection of a target nucleic acid, as mentioned above. The primer, the probe and/or the clamp nucleic acid can be designed appropriately depending on the types of the nucleotide sequence of a target nucleic acid or a non-target nucleic acid.

One embodiment of the test composition contains a primer and a probe. At least one of them is the oligonucleotide (4). The primer and the probe may be included in a single container, or may be included in different containers separately.

Figure 11A:
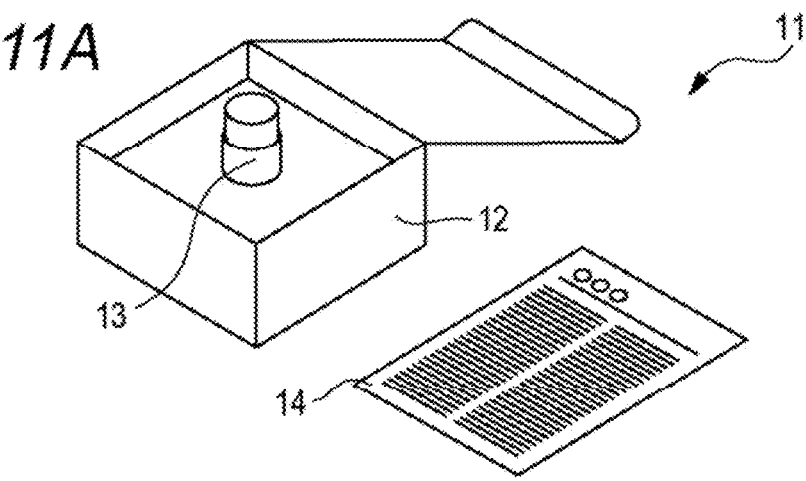
FIGS. 11A-11C are diagrams illustrating examples of a kit for detecting a target nucleic acid in a test specimen according to the present invention.

FIG. 11A is a schematic diagram of one example of a kit in which the primer and the probe, which constitute the test composition, are included in a single container. The kit 11 includes an outer packaging box 12, a container support which is arranged in the outer packaging box 12 and has a depressed part formed on the surface thereof, a container 13 which is installed in the depressed part and in which a primer and a probe are contained, and a package insert 14. On the package insert 14, a method for handling the kit 11, the conditions for storage of the kit 11, the validity date of the kit 11 and the like can be written.

Figure 11B:
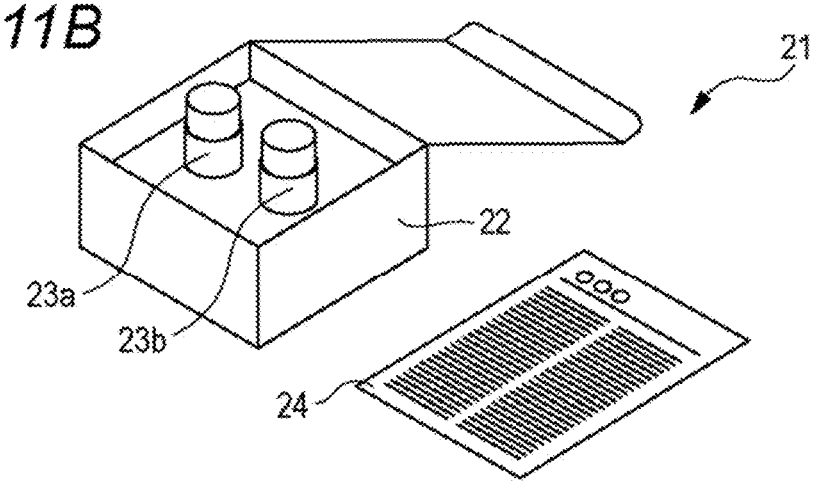

FIG. 11B is a schematic diagram of one example of a kit in which the primer and the probe, which constitute the test composition, are included separately in different containers. The kit 21 includes an outer packaging box 22, a container support which is arranged in the outer packaging box 22 and has a first depressed part and a second depressed part formed apart from each other on the surface thereof along the length direction, a container 23a which is installed in the first depressed part and in which the primer is contained, a container 23*b* which is installed in the second depressed part and in which the probe is contained, and a package insert 24.

Another embodiment of the test composition contains a forward primer, a reverse primer and a probe. At least one of them is the oligonucleotide (4). The three components, i.e., the forward primer, the reverse primer and the probe, may be contained in a single container (e.g., a kit shown in FIG. 11A), or any two of them may be contained in a single container (e.g., a kit shown in FIG. 11B), or all of the three components are contained in different containers separately.

Figure 11C:
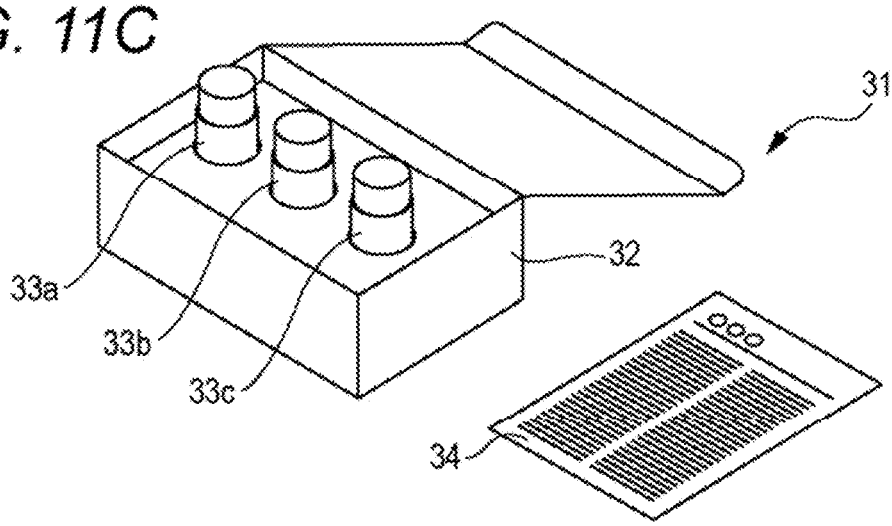

FIG. 11C is a schematic diagram of one example of the kit in which all of the forward primer, the reverse primer and the probe are contained in different containers separately. The kit 31 includes an outer packaging box 32, a container support which is arranged in the outer packaging box 32 and has first to third depressed parts formed apart from each other on the surface thereof along the length direction, a container 33*a* which is installed in the first depressed part and in which the forward primer is contained, a container 33*b* which is installed in the second depressed part and in which the reverse primer is contained, a container 33*c* which is installed in the third depressed part and in which the probe is contained, and a package insert 34.

Another embodiment of the test composition includes a clamp nucleic acid and a primer. At least one of them is the oligonucleotide (4). The test composition may be one for amplifying only a target nucleic acid. The clamp nucleic acid and the primer may be contained in a single container (e.g., a kit shown in FIG. 11A), or may be contained in different containers separately (e.g., a kit shown in FIG. 11B).

Still another embodiment of the test composition contains a clamp nucleic acid, a primer and a probe. At least one of them is the oligonucleotide (4). The three components, i.e., the clamp nucleic acid, the primer and the probe, may be contained in a single container (e.g., a kit shown in FIG. 11A), or any two of them may be contained in a single container (e.g., a kit shown in FIG. 11B), or all of the three components are contained in different containers separately (e.g., a kit shown in FIG. 11C).

In the kit, a DNA polymerase, deoxynucleoside triphosphates (dNTPs), a reaction buffer, a salt, a restriction enzyme and the like may also be contained.

The present invention includes a use of an oligonucleotide (4) for detecting a target nucleic acid in a test specimen or for selectively amplifying a nucleotide sequence including a target site in a target nucleic acid in a test specimen. The oligonucleotide (4) has the same characteristic properties as, for example, those of the oligonucleotide (4) contained in the test composition.

<<Composition for Strand Invasion of Oligonucleotide into Target Site in Double-Stranded DNA>>

The present invention includes a composition for causing the strand invasion of an oligonucleotide into a target site in double-stranded DNA (hereinafter, also referred to as a "composition for strand invasion").

The composition for strand invasions contains an oligonucleotide (4) having a nucleotide sequence complementary to the nucleotide sequence for the target site.

The composition for strand invasion may contain only one oligonucleotide (4) or may contain two or more oligonucleotides (4). In one embodiment, each of two or more oligonucleotides (4) can hybridize with one of the strands of double-stranded DNA. In another embodiment, the two or more oligonucleotides (4) include an oligonucleotide capable of hybridizing with one strand of the double-stranded DNA and an oligonucleotide capable of hybridizing with the other strand of the double-stranded DNA. When two or more oligonucleotides (4) are used, the strand invasion can be further enhanced.

The composition for strand invasion may further contain a single-stranded DNA binding protein. However, it is found for the first time from the below-mentioned experiments that, when the oligonucleotide (4) according to the present invention is used, strand invasion can be caused without the need to add a single-stranded DNA binding protein. Therefore, an embodiment in which the composition for strand invasion does not contain a single-stranded DNA binding protein is also preferred.

The composition for strand invasion may contain at least one component selected from water containing a buffer (or a buffer solution), a salt, and co-solvent. As these components, those exemplified in the section "composition containing oligonucleotide (4)" can be used.

In the composition for strand invasion, the concentration of the oligonucleotide (4) can be adjusted appropriately with taking the sequences or nucleotide lengths of the oligonucleotide (4) and the target double-stranded DNA into consideration. When a strand invasion reaction is carried out in vitro, the concentration of the like of the target double-stranded DNA in a sample can be taken into consideration. When the strand invasion reaction is carried out in vivo, the kinetics (more specifically, the concentration in blood, a half life in blood) of the oligonucleotide (4) in a living body can be taken into consideration. The lower limit of the concentration of the oligonucleotide (4) in the composition for strand invasion is, for example 50 nM, preferably 100 nM, and the upper limit of the concentration of the oligonucleotide (4) is for example 3000 nM, preferably 2500 nM, more preferably 2000 nM, more preferably 1500 nM, particularly preferably 1000 nm. The concentration of the oligonucleotide (4) is for example 50 to 2000 nM, preferably 100 to 1000 nM.

The oligonucleotide (4) has high sequence-selectivity. Therefore, the composition for strand invasions can bind specifically only to the nucleotide sequence for the target site which has a complementary nucleotide sequence. The oligonucleotide (4) has a high Tm value and, therefore, can bind to the nucleotide sequence for the target site strongly to form a stable strand invasion. Furthermore, the oligonucleotide (4) is less likely to be decomposed with a nuclease. Therefore, the oligonucleotide (4) can be used suitably in the composition for strand invasion.

The present invention includes a use of the oligonucleotide (4) for causing the strand invasion of an oligonucleotide into a target site in double-stranded DNA. The oligonucleotide (4) to be used has the same characteristic properties as, for example, those of the oligonucleotide (4) contained in the composition for strand invasion.

<<Method for Strand-Invading Oligonucleotide into Target Site in Double-Stranded DNA>>

The present invention includes a method for strand-invading an oligonucleotide into a target site in double-stranded DNA (hereinafter, also referred to as a "strand invasion method").

The strand invasion method includes a step of mixing an oligonucleotide (4) having a nucleotide sequence complementary to the nucleotide sequence for the target site in the double-stranded DNA with the double-stranded DNA.

In one embodiment, the mixing step is a step of mixing the oligonucleotide (4) with the double-stranded DNA in the presence of a single-stranded DNA binding protein.

This step may be carried out in the presence of a buffer and/or a salt. The buffer and the salt may be selected from, for example, those described in the section "composition containing oligonucleotide (4)".

The mixing step may be carried out in the absence of a single-stranded DNA binding protein. That is, in another embodiment, the strand invasion method includes: a step of mixing the oligonucleotide (4) with the double-stranded DNA in the absence of a single-stranded DNA binding protein to prepare a mixture; and a step of heating the mixture.

The mixing step in the absence of a single-stranded DNA binding protein may be carried out in the presence of a buffer and/or a salt. The buffer and the salt may be selected from, for example, those described in the section "composition for strand invasion".

In the step of heating the mixture, the heating temperature can be selected from, for example, a range higher than 75° C. The lower limit of the heating temperature is preferably 80° C., more preferably 85° C., still more preferably 90° C., and the upper limit of the heating temperature is preferably 100° C. The heating temperature is preferably 80 to 100° C., more preferably 85 to 100° C., particularly preferably 90 to 100° C. The heating time is not particularly limited. The lower limit of the heating time is for example 7 minutes, preferably 8 minutes, more preferably 9 minutes, particularly preferably 10 minutes, and the upper limit of the heating time is for example 12 hours, preferably 6 hours, more preferably 3 hours, still more preferably 1 hour, particularly preferably 30 minutes. The heating temperature is for example 7 minutes to 12 hours, preferably 8 minutes to 6 hours, more preferably 9 minutes to 1 hour, particularly preferably 10 minutes to 30 minutes.

This method may further include a step of cooling the heated mixture. In this cooling, the lower limit of the cooling achieving temperature is for example 30° C., preferably 35° C., more preferably 40° C., still more preferably 45° C., and the upper limit of the cooling achieving temperature is preferably 60° C. The cooling achieving temperature is for example 30 to 60° C., preferably 40 to 60° C., still more preferably 45 to 60° C. The coiling rate is not particularly limited. The lower limit of the cooling rate is for example 1° C./min., preferably 2° C./min., and the upper limit of the cooling rate is for example 10° C./min., preferably 9° C./min., more preferably 8° C./min. The cooling rate is for example 1 to 10° C./min., preferably 2 to 8° C./min.

That is, in another embodiment, the strand invasion method includes: a step of mixing the oligonucleotide (4) with the double-stranded DNA in the absence of a single-stranded DNA binding protein to prepare a mixture; and a step of retaining the mixture at 25 to 75° C.

As mentioned above, the mixing step in the absence of a single-stranded DNA binding protein may be carried out in the presence of a buffer and/or a salt. The buffer and the salt may be selected from, for example, those described in the section "composition for strand invasion".

In the step of retaining the mixture in a specific temperature range, the retaining time is not particularly limited. The lower limit of the retaining time is for example 2 hours, preferably 4 hours, more preferably 6 hours, and the upper limit of the retaining time is for example 60 hours, preferably 48 hours, still more preferably 24 hours. The retaining time is for example 2 to 60 hours, preferably 4 to 48 hours, more preferably 6 to 24 hours.

As mentioned above, when the oligonucleotide (4) is used, it becomes possible to cause strand invasion in a wide temperature range regardless the presence or absence of a single-stranded DNA binding protein.

<Pharmaceutical Composition (or Preparation)>

The pharmaceutical composition (or preparation) according to the present invention contains the compound (1) or the oligonucleotide (4). An example of the pharmaceutical composition (or preparation) containing the compound (1) is a low-molecular-weight medicine such as azidothymidine (AZT) that is a nucleoside analogue reversetranscriptase inhibitor: NRTI). An example of the pharmaceutical composition (or preparation) containing the oligonucleotide (4) is a nucleic acid medicine of a middle-molecular-weight molecule such as an antisense, siRNA (small interfering RNA), an aptamer, a decoy nucleic acid and a CpG oligo or a high-molecular-weight molecule.

The pharmaceutical composition may be any one of a liquid preparation (e.g., an injection, eye drops, nasal drops, a suspension), a solid preparation (e.g., tables, granules, a powder), a semi-solid preparation (e.g., an ointment, a suppository), and other preparation form known to persons skilled in the art.

A preferred example of the pharmaceutical composition is a preparation for parenteral administration (e.g., a preparation for subcutaneous administration, a preparation of transnasal administration, a preparation for intrathecal administration, a preparation for intraventricular administration, a preparation for intravitreous administration).

Another preferred example of the pharmaceutical composition is a topical preparation.

In general, the pharmaceutical composition further contains a pharmaceutically acceptable carrier or an additive.

The carrier includes a solid carrier and a liquid carrier. Examples of the solid carrier include starch, lactose, calcium sulfate dihydrate, sucrose, talc, gelatin, agar, pectin, gum arabic, magnesium stearate, and stearic acid. An example of the liquid carrier is water (including physiological saline).

The additive includes a stabilizing agent, and examples of the stabilizing agent include: a para-hydroxybenzoic acid ester such as methylparaben and propylparaben; an alcohol such as benzyl alcohol; and a phenol compound such as phenol and cresol.

The oligonucleotide (4) has high sequence selectivity and a high Tm value, and is therefore less likely to be decomposed with a nuclease. Accordingly, the pharmaceutical composition (or preparation) containing the compound (1) or the oligonucleotide (4) can recognize a target (e.g., a target gene) in a living body with high sequence selectivity and can act on the target.

EXAMPLES

Hereinbelow, the present invention will be described in more detail with reference to examples. However, the present invention is not limited by these examples.

Compound (1) Synthesis Examples

Symbols and abbreviated words used in Synthesis Examples are as follows.
Bz: benzoyl
DMTr: dimethoxytrityl
Ph: phenyl
i-Pr: isopropyl
Ts: tosyl
BSA: N,O-bis(trimethylsilyl)acetamide
DIPEA: diisodiisopropylethylamine
DMAP: dimethylaminopyridine
DMF: dimethylformamide
$PPh_3$: triphenylphosphine Et$_3$N: triethylamine
MeOH: methanol
TBAF: tetra-n-butylammonium fluoride
TFA: trifluoromethylcarbonyl
TFAA: trifluoroacetic anhydride
THF: tetrahydrofuran
TMSOTf: trimethylsilyl trifluoromethanesulfonate
rt: room temperature
d: day
h: hour
min: minute Synthesis Example 1

A compound (1) in which "Base" was a thymin-1-yl group, $A^1$ was a methylene group, $A^2$ was a single bond, X was a n-propylene group, $R^1$ was DMTr, $R^2$ was —P(N(i-Pr)$_2$)(OC$_2$H$_4$CN), and $R^3$ was a trifluoromethylcarbonylamino group (hereinafter, also referred to as "compound AP-T-6") was synthesized according to the reaction scheme shown below.

[Formula 51]
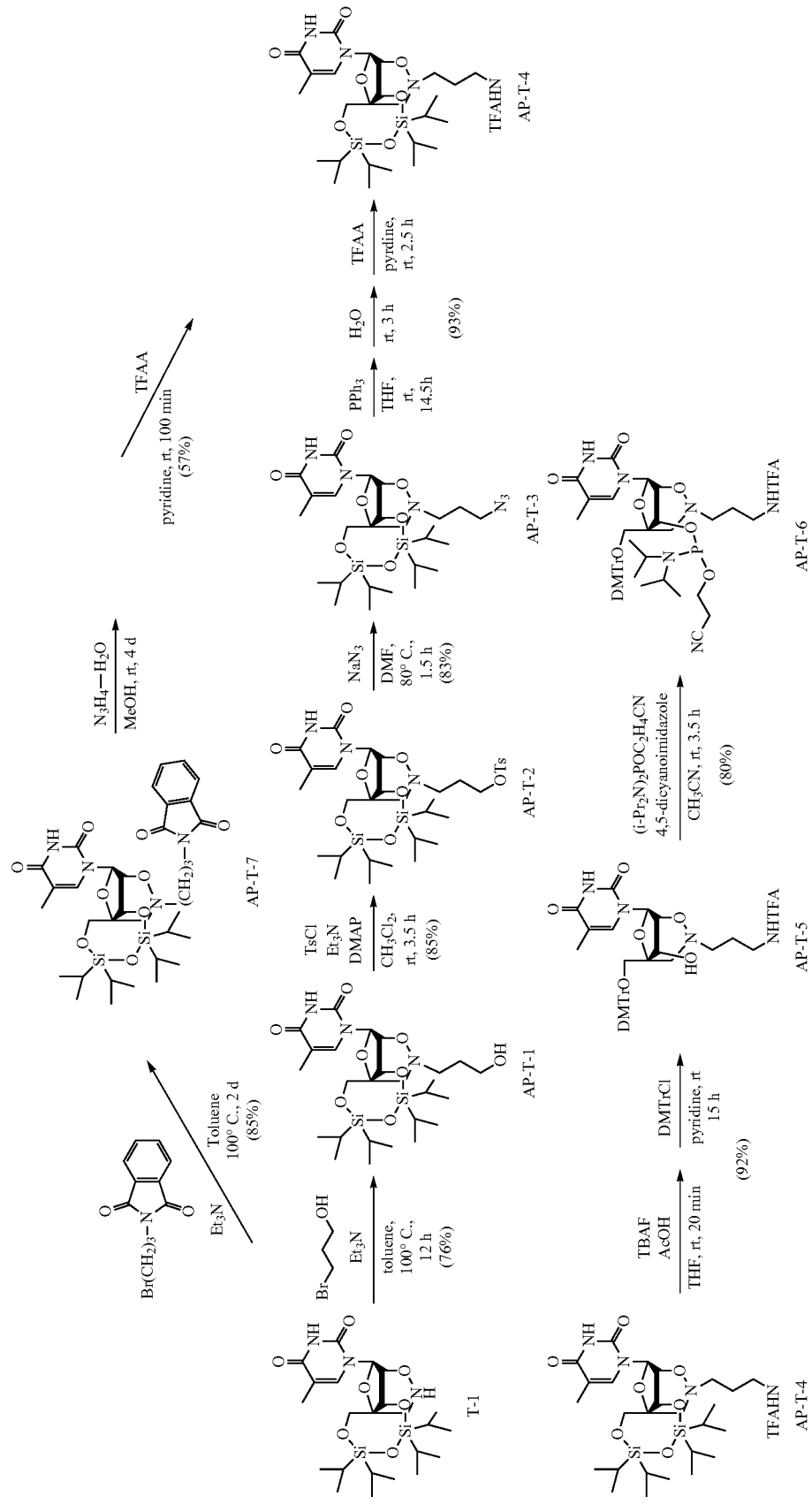

(Synthesis of Compound AP-T-1)

Under a nitrogen stream, compound T-1 (4.72 g, 8.93 mmol) was dissolved in toluene (80 mL), then triethylamine (7.5 mL, 53.58 mmol) and 3-bromo-1-propanol (3.5 mL, 40.19 mmol) were added in this order to the resultant solution at room temperature, and then the resultant solution was stirred at 100° C. for 12 hours. The reaction solution was cooled, then the reaction was terminated with an aqueous sodium bicarbonate solution, then the resultant solution was diluted with ethyl acetate and water, and then the diluted solution was fractionated into an organic layer and an aqueous layer. The aqueous layer was subjected to back-extraction with ethyl acetate. The organic layer obtained in the first fractionation was combined with the organic layer obtained in the back-extraction, the resultant solution was washed with saturated saline, and then the washed solution was dried over anhydrous sodium sulfate and was then distilled under reduced pressure. A crude product thus produced was purified by silica gel column chromatography (hexane:ethyl acetate=1:1 to 1:3) to produce compound AP-T-1 (4.15 g, yield: 76%) as a white solid substance. $^1$H NMR (CDCl$_3$) δ 0.94-1.12 (28H, m), 1.79-1.87, 1.96-2.03 (2H, m), 1.92 (3H, d, J=1 Hz), 2.37 (1H, t, J=5 Hz), 2.65, 2.97 (2H, ABq, J=11 Hz), 2.86-2.93, 3.05-3.12 (2H, m), 3.67, 4.04 (2H, ABq, J=13 Hz), 3.76-3.83 (2H, m), 3.97 (1H, d, J=3 Hz), 4.35 (1H, d, J=3 Hz), 6.21 (1H, s), 7.70 (1H, d, J=2 Hz), 8.70 (1H, s).

(Synthesis of Compound AP-T-2)

Under a nitrogen stream, compound AP-T-1 (4.13 g, 7.05 mmol) was dissolved in methylene chloride (43 mL), then p-toluenesulfonyl chloride (1.59 g, 8.36 mmol), triethylamine (1.7 mL, 12.36 mmol) and 4-dimethylaminopyridine (0.177 g, 1.45 mmol) were then added in this order to the resultant solution under ice cooling, and then the resultant solution was stirred at room temperature for 4 hours. The reaction solution was cooled, then the reaction was terminated with an aqueous sodium bicarbonate solution, then the resultant solution was diluted with methylene chloride and water, and the diluted solution was then fractionated into an organic layer and an aqueous layer. The aqueous layer was subjected to back-extraction with ethyl acetate. The organic layer obtained in the first fractionation and the organic layer obtained in the back-extraction were then washed with saturated saline separately, then the organic layers were combined together, and the resultant solution was dried over anhydrous sodium sulfate and was then distilled under reduced pressure. A crude product thus produced was purified by silica gel column chromatography (hexane:ethyl acetate=1:1 to 1:2) to produce compound AP-T-2 (4.65 g, 88%) as a white foam-like solid substance. $^1$H NMR (CDCl$_3$) δ 0.94-1.12 (28H, m), 1.92 (3H, d, J=1 Hz), 1.95-1.99, 2.06-2.15 (2H, m), 2.42 (3H, s), 2.48, 2.93 (2H, ABq, J=11 Hz), 2.77-2.84, 2.86-2.91 (2H, m), 3.65, 4.02 (2H, ABq, J=13 Hz), 3.93 (1H, d, J=3 Hz), 4.10-4.15, 4.18-4.24 (2H, m), 4.25 (1H, d, J=3 Hz), 5.97 (1H, s), 7.32-7.34 (2H, m), 7.78-7.80 (2H, m), 7.70 (1H, d, J=1 Hz), 8.30 (1H, s).

(Synthesis of Compound AP-T-3)

Under a nitrogen stream, compound AP-T-2 (4.65 g, 6.28 mmol) was dissolved in N,N-dimethylformamide (49 mL), then sodium azide (0.52 g, 7.94 mmol) was added to the solution at room temperature, and the resultant solution was stirred at 90° C. for 2 hours. The reaction solution was cooled, then the reaction was terminated with an aqueous sodium bicarbonate solution, then the resultant solution was diluted with ethyl acetate and water, and the diluted solution was fractionated to obtain an organic layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=3:1 to 2:1) to produce compound AP-T-3 (3.38 g, 83%) as a white foam-like solid substance. $^1$H NMR (CDCl$_3$) δ 0.91-1.12 (28H, m), 1.80-1.93, 1.99-2.09 (2H, m), 1.89 (3H, d, J=2 Hz), 2.59, 2.97 (2H, ABq, J=11 Hz), 2.76-2.83, 2.92-2.99 (2H, m), 3.35-3.49 (2H, m), 3.64, 4.02 (2H, ABq, J=13 Hz), 3.96 (1H, d, J=3 Hz), 4.32 (1H, d, J=3 Hz), 6.20 (1H, s), 7.68 (1H, d, J=1 Hz), 8.33 (1H, s).

(Synthesis of Compound AP-T-4)

Under a nitrogen stream, compound AP-T-3 (3.40 g, 5.57 mmol) was dissolved in tetrahydrofuran (48 mL), triphenylphosphine (3.74 g, 14.26 mmol) was then added to the solution, and the resultant solution was stirred at room temperature for 14.5 hours. Subsequently, water (3 mL) was added to the reaction solution at room temperature, and the solution was further stirred for 3 hours. The resultant reaction solution was subjected to distillation under reduced pressure to produce an intermediate. The intermediate was azeotropically dehydrated with a pyridine:toluene (=1:1) mixed solution and pyridine in this order. Subsequently, under a nitrogen stream, the resultant product was dissolved in pyridine (48 mL), then trifluoroacetic anhydride (2.1 mL, 14.90 mmol) was added to the resultant solution under ice cooling, and the solution was at room temperature for 2.5 hours. The reaction solution was cooled, then the reaction was terminated with an aqueous sodium bicarbonate solution, then the resultant solution was diluted with ethyl acetate and water, and then the resultant solution was fractionated into an organic layer and an aqueous layer. The aqueous layer was subjected to back-extraction with ethyl acetate, then the organic layer obtained in the first fractionation and the organic layer obtained in the back-extraction were washed with saturated saline separately, then the organic layers were combined together, and the resultant solution was dried over anhydrous sodium sulfate and was then distilled under reduced pressure. A crude product thus produced was purified by silica gel column chromatography (hexane:ethyl acetate=2:1 to 3:2) to produce compound AP-T-4 (3.53 g, 93%) as a pale yellow solid substance. $^1$H NMR (CDCl$_3$) δ 0.94-1.12 (28H, m), 1.83-1.89, 2.01-2.12 (2H, m), 1.92 (3H, d, J=1 Hz), 2.60, 2.98 (2H, ABq, J=11 Hz), 2.73-2.82, 3.02-3.08 (2H, m), 3.48-3.55 (2H, m), 3.67, 4.04 (2H, ABq, J=13 Hz), 3.97 (1H, d, J=3 Hz), 4.33 (1H, d, J=3 Hz), 6.22 (1H, s), 7.40 (1H, m), 7.69 (1H, d, J=1 Hz), 9.24 (1H, s).

(Synthesis of Compound AP-T-5)

Compound AP-T-4 (3.53 g, 5.17 mmol) was dissolved in tetrahydrofuran (47 mL), then acetic acid (0.49 mL, 8.54 mmol) and tetra-n-butylammonium fluoride (a 1-M tetrahydrofuran solution, 12.0 mL, 12.0 mmol) were added in this order to the solution, and the resultant solution was stirred at room temperature for 20 minutes. The resultant reaction solution was subjected to distillation under reduced pressure, and a reaction residue was removed by silica gel column chromatography (ethyl acetate:methanol=20:1 to 10:1) to produce an intermediate. The intermediate was azeotropically dried with pyridine. Subsequently, under a nitrogen stream, the resultant produce was dissolved in pyridine (30 mL). 4,4'-Dimethoxytrityl chloride (2.50 g, 7.40 mmol) was added to the solution, and the resultant solution was stirred at room temperature for 15 hours. The reaction solution was cooled, then the reaction was terminated with cold water, and the solution was diluted with ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=1:1 to 1:3) to produce compound AP-T-5 (3.91 g, 92%) as a yellow foam-like solid substance. ¹H NMR (CDCl₃) δ 1.47 (3H, s), 1.82-1.91, 1.99-2.08 (2H, m), 2.62 (1H, d, J=8 Hz), 2.70-2.78, 2.94-3.02 (2H, m), 2.76, 2.86 (2H, ABq, J=12 Hz), 3.33, 3.39 (2H, ABq, J=11 Hz), 3.46-3.51 (2H, m), 4.26 (1H, d, J=8 Hz), 4.38 (1H, br), 6.09 (6H, s), 6.33 (1H, s), 6.85 (4H, d, J=8 Hz), 7.22-7.46 (10H, m), 7.74 (1H, s), 9.22 (1H, s).

(Synthesis of Compound AP-T-6)

Under a nitrogen stream, compound AP-T-5 (3.90 g, 5.26 mmol) was azeotropically dried with acetonitrile, and was then dissolved in acetonitrile (47 mL). 4,5-Dicyanoimidazole (0.69 g, 5.85 mmol) and 2-cyanoethyl N,N,N',N'-tetraisopropylphosphordiamidite (2.5 mL, 7.45 mmol) were added in this order to the solution under ice cooling, and the resultant solution was stirred at room temperature for 3.5 hours. The reaction solution was cooled, then the reaction was terminated with an aqueous sodium bicarbonate solution, then the resultant solution was diluted with ethyl acetate and water, and the diluted solution was fractionated to obtain an organic layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=3:2 to 1:2) to produce compound AP-T-6 (4.02 g, 80%) as a white foam-like solid substance. ³¹P NMR (CDCl₃) δ 149.4, 150.1.

HRMS (MALDI): calcd for $C_{46}H_{56}F_3N_6NaO_{10}P$ [M+Na⁺] 963.3640, found 963.3656.

(Synthesis of Compound AP-T-7)

N-(3-Bromopropyl)phthalimide (15.3 g, 57.0 mmol) and triethylamine (12.4 mL, 89.2 mmol) were added to a solution of compound T-1 (6.70 g, 12.7 mmol) in toluene (80 mL) at room temperature, and the resultant solution was warmed to 100° C. and was then stirred for 2 days. Water was added to the solution under ice cooling, the resultant solution was extracted with ethyl acetate, and an organic layer thus obtained was washed with saturated saline and was then dried over anhydrous sodium sulfate. Anhydrous sodium sulfate was removed by filtration, then a filtrate was subjected to distillation under reduced pressure to produce a crude product, and the crude product was purified by silica gel column chromatography (hexane:ethyl acetate=4:1 to 2:1) to produce compound AP-T-7 (7.68 g, 85%) as a white solid substance.

¹H NMR (CDCl₃) δ 0.95-1.11 (28H, m), 1.91 (3H, s), 1.95-2.16 (2H, m), 2.58 (1H, d, J=11 Hz), 2.68-2.75 (1H, m), 2.93 (1H, d, J=11 Hz), 2.99-3.05 (1H, m), 3.65 (1H, d, J=13 Hz), 3.77-3.87 (2H, m), 3.94 (1H, d, J=3 Hz), 4.03 (1H, d, J=13 Hz), 4.32 (1H, d, J=3 Hz), 6.16 (1 H, s), 7.68-7.71 (3H, m), 7.81-7.86 (2H, m), 8.25 (1H, brs).

(Synthesis of Compound AP-T-4 (Via Compound AP-T-7))

Hydrazine monohydrate (0.016 mL, 0.33 mmol) was added to a solution of compound AP-T-7 (100 mg, 0.14 mmol) in methanol (2 mL), and the resultant solution was stirred at room temperature overnight. Subsequently, hydrazine monohydrate (0.008 mL, 0.16 mmol) was added to the solution, and the resultant solution was stirred at room temperature for 3 days. Dichloromethane was added to a residue obtained by the distillation of the solvent away under reduced pressure, and then an insoluble matter was filtrated off. A filtrate was subjected to distillation under reduced pressure to obtain a residue, the residue was dissolved in pyridine (3 mL), then trifluoroacetic anhydride (0.045 mL, 0.32 mmol) was added to the solution under ice cooling, and the resultant solution was stirred at room temperature for 1 hour and 40 minutes. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure, and a crude product thus produced was purified by silica gel column chromatography (hexane:ethyl acetate=2:1 to 3:2) to produce compound AP-T-4 (82.9 mg, 87%) as a white solid substance.

Synthesis Example 2

A compound (1) in which "Base" was an N-benzoyl-5-methylcytosin-1-yl group, $A^1$ was a methylene group, $A^2$ was a single bond, X was a n-propylene group, $R^1$ was DMTr, $R^2$ was —P(N(i-Pr)₂)(OC₂H₄CN), and $R^3$ was a trifluoromethylcarbonylamino group (hereinafter, also referred to as "compound AP-C-3") was synthesized according to the reaction scheme shown below.

[Formula 52]

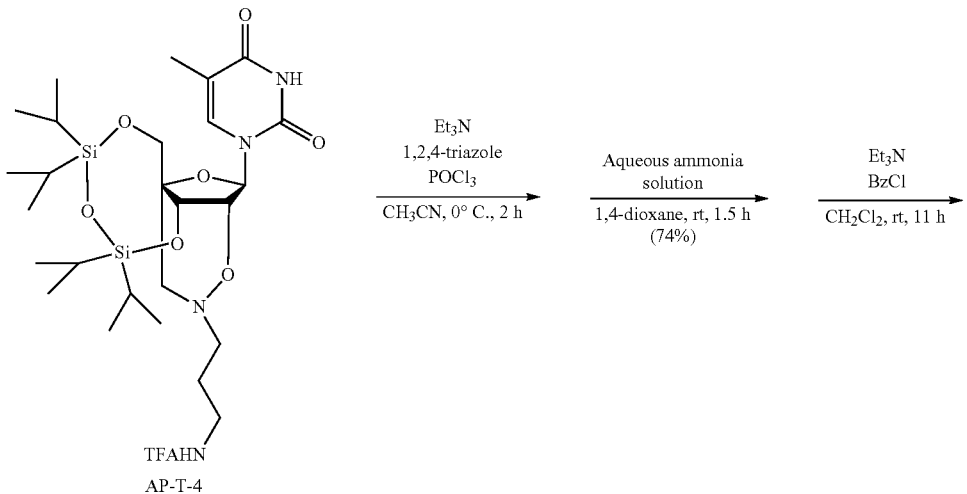

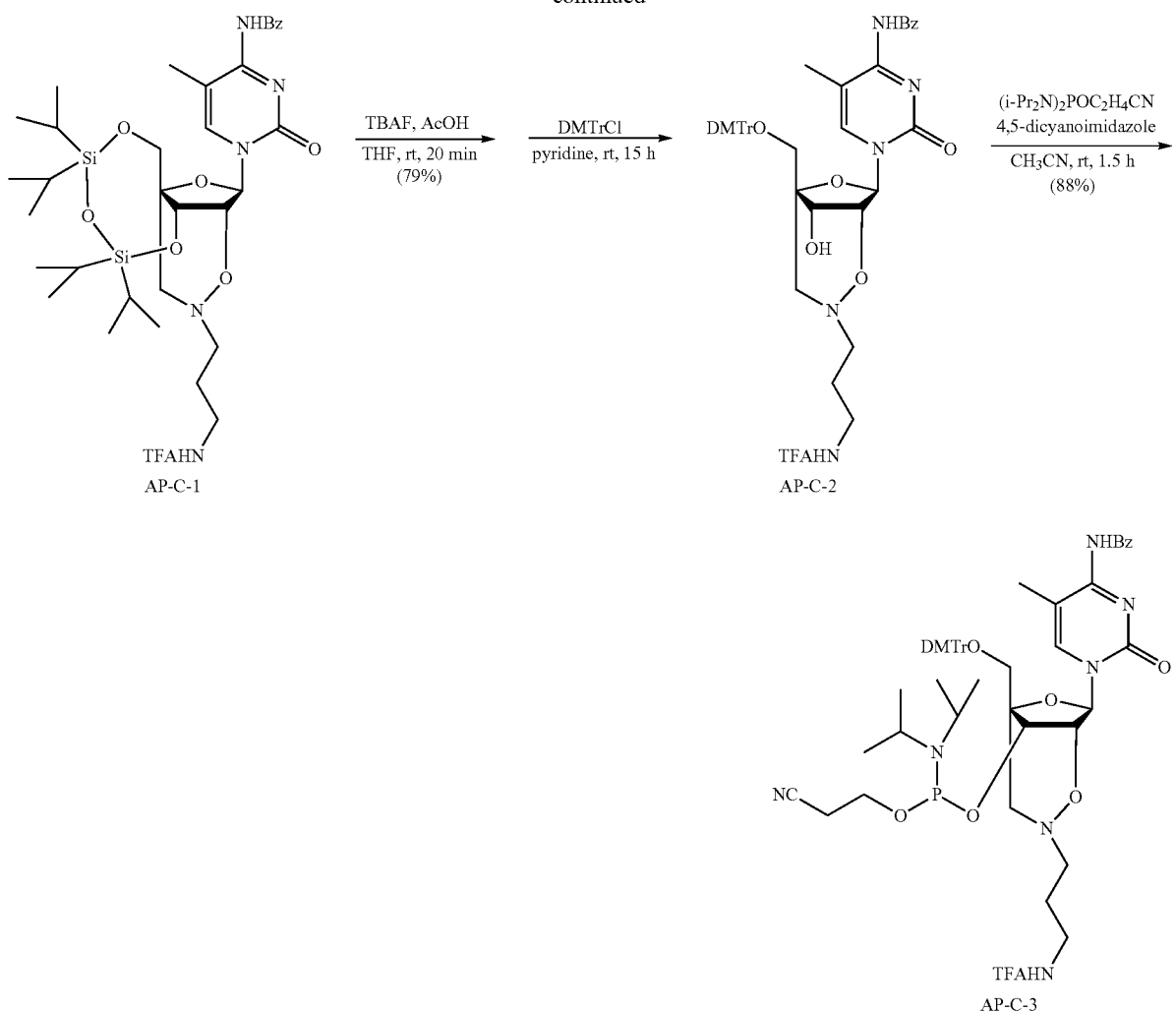

(Synthesis of Compound AP-C-1)

Under a nitrogen stream, compound AP-T-4 (0.34 g, 0.50 mmol) was dissolved in acetonitrile (4.3 mL), then triethylamine (0.88 mL, 6.34 mmol), 1,2,4-triazole (0.29 g, 4.22 mmol) and phosphoryl chloride (99 µL, 1.06 mmol) were added in this order to the resultant solution under ice cooling, and the resultant solution was stirred under ice cooling for 2 hours. The reaction in the reaction solution was terminated with an aqueous sodium bicarbonate solution, the resultant solution was diluted with ethyl acetate and water, and a diluted solution was then fractionated into an organic layer and an aqueous layer. The resultant organic layer was washed with saturated saline, was then dried over anhydrous sodium sulfate, and was then subjected to distillation under reduced pressure to produce an intermediate. The intermediate was dissolved in 1,4-dioxane (4.4 mL), then a 28% aqueous ammonia solution (1.1 mL) was added to the solution, and the resultant solution was stirred under room temperature for 1.5 hours. The resultant reaction solution was subjected to distillation under reduced pressure to produce an intermediate. The intermediate was azeotropically dehydrated with toluene, then the resultant product was dissolved in methylene chloride (4.3 mL) under a nitrogen stream, then triethylamine (0.14 mL, 1.06 mmol) and benzoyl chloride (0.11 mL, 0.95 mmol) were then added in this order to the resultant solution under ice cooling, and the resultant solution was stirred under room temperature for 11 hours. The reaction in the reaction solution was terminated with an aqueous sodium bicarbonate solution, then the reaction solution was diluted with methylene chloride and water, the diluted solution was fractionated into an organic layer and an aqueous layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=7:1 to 3:3) to produce compound AP-C-1 (0.29 g, 74%) as a yellow foam-like solid substance.

$^1$H NMR (CDCl$_3$) δ 0.95-1.12 (28H, m), 1.84-1.95, 2.00-2.09 (2H, m), 2.13 (3H, d, J=1 Hz), 2.61, 2.99 (2H, ABq, J=11 Hz), 2.74-2.83, 3.00-3.09 (2H, m), 3.49-3.56 (2H, m), 3.68, 4.07 (2H, ABq, J=13 Hz), 3.99 (1H, d, J=3 Hz), 4.39 (1H, d, J=3 Hz), 6.20 (1H, s), 7.01 (1H, m), 7.42-7.47 (2H, m), 7.51-7.57 (1H, m), 7.90 (1H, d, J=1 Hz), 8.30-8.33 (2H, m), 13.46 (1H, s).

(Synthesis of Compound AP-C-2)

Compound AP-C-1 (1.98 g, 2.47 mmol) was dissolved in tetrahydrofuran (20 mL), then acetic acid (0.20 mL, 3.57 mmol) and tetra-n-butylammonium fluoride (a 1-M tetrahydrofuran solution, 5.4 mL, 5.4 mmol) were added in this order to the solution, and the resultant solution was stirred at room temperature for 20 minutes. The resultant reaction solution was subjected to distillation under reduced pressure, and a reaction residue was removed by silica gel column chromatography (ethyl acetate:methanol=80:1 to 60:1) to produce an intermediate. The intermediate was azeotropically dried with pyridine, and the resultant product was dissolved in pyridine (25 mL) under a nitrogen stream. 4,4'-Dimethoxytrityl chloride (1.21 g, 3.57 mmol) was added to the solution, and the resultant solution was stirred at room temperature for 15 hours. The reaction solution was cooled, then the reaction was terminated with an aqueous sodium bicarbonate solution and was then diluted with water and ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus produced was purified by silica gel column chromatography (hexane:ethyl acetate=2:1 to 1:1) to produce compound AP-C-2 (1.64 g, 79%) as a yellow foam-like solid substance.

$^1$H NMR (CDCl$_3$) δ 1.64 (3H, s), 1.81-1.91, 1.98-2.08 (2H, m), 2.51 (1H, d, J=9 Hz), 2.70-2.77, 2.94-3.02 (2H, m), 2.77, 2.86 (2H, ABq, J=12 Hz), 3.34, 3.42 (2H, ABq, J=11 Hz), 3.47-3.56 (2H, m), 3.80 (6H, d=1 Hz), 4.28 (1H, dd, J=3.9 Hz), 4.43 (1H, d, J=3 Hz), 6.33 (1H, s), 6.84-6.88 (5H, m), 7.23-7.48 (11H, m), 7.50-7.56 (1H, m), 7.95 (1H, s), 8.28-8.30 (2H, m), 13.45 (1H, brs).

(Synthesis of Compound AP-C-3)

Under a nitrogen stream, compound AP-C-2 (8.49 g, 5.26 mmol) was azeotropically dried with acetonitrile, and was then dissolved in acetonitrile (95 mL). 4,5-Dicyanoimidazole (1.32 g, 11.17 mmol) and 2-cyanoethyl N,N,N',N'-tetraisopropylphosphordiamidite (4.0 mL, 12.18 mmol) were added in this order to the solution, and the resultant solution was stirred at room temperature for 1.5 hours. The reaction solution was cooled, then the reaction was terminated with water, then the solution was diluted with ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus obtained was purified by silica gel column chromatography to produce compound AP-C-3 (8.31 g, 86%) as a yellow foam-like solid substance.

$^{31}$P NMR (CDCl$_3$) δ 148.9, 149.6.

HRMS (MALDI): calcd for C$_{53}$H$_{61}$F$_3$N$_7$NaO$_{10}$P [M+Na$^+$] 1066.4062, found 1066.4037.

Synthesis Example 3

A compound (1) in which "Base" was an N-benzoyl-adenin-9-yl group, A$^1$ was a methylene group, A$^2$ was a single bond, X was a n-propylene group, R$^1$ was DMTr, R$^2$ was —P(N(i-Pr)$_2$)(OC$_2$H$_4$CN), and R$^3$ was a trifluoromethylcarbonylamino group (hereinafter, also referred to as "compound AP-A-3") was synthesized according to the reaction scheme shown below.

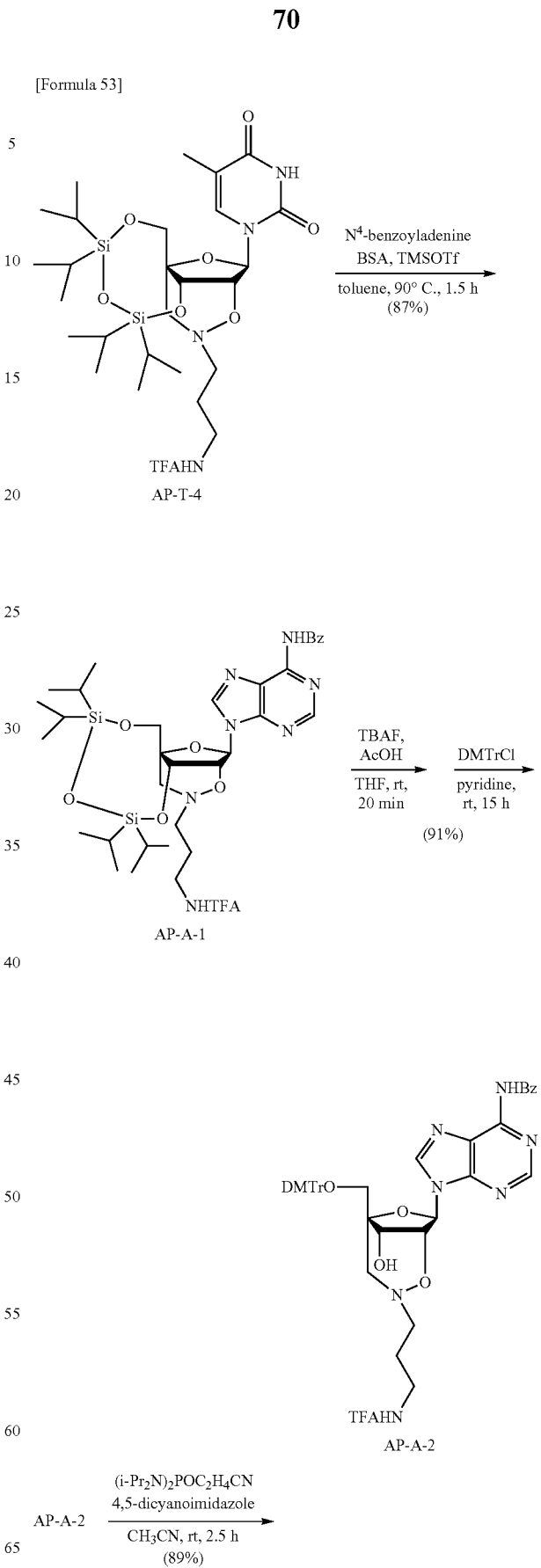

[Formula 53]

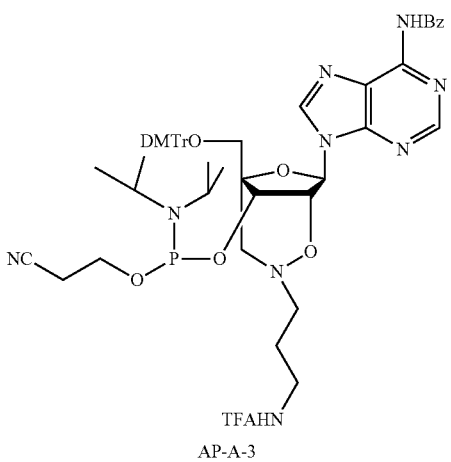

AP-A-3

(Synthesis of Compound AP-A-1)

Under a nitrogen stream, compound AP-T-4 (4.80 g, 7.05 mmol) was dissolved in toluene (75 mL), then $N^6$-benzoyladenine (2.78 g, 11.63 mmol) and N,O-bis(trimethylsilyl)acetamide (9.0 mL, 36.35 mmol) were added in this order to the solution, and the resultant solution was stirred at 90° C. for 0.5 hour. Subsequently, trimethylsilyl trifluoromethanesulfonate (2.0 mL, 11.63 mmol) was added to the solution, and the resultant solution was stirred at 90° C. for 1 hour. The reaction solution was cooled, then the reaction was terminated with an aqueous sodium bicarbonate solution, then the resultant solution was diluted with ethyl acetate and water, and the reaction solution was subjected to filtration through celite to collect a filtrate. The collected filtrate was fractionated into an organic layer and an aqueous layer, the organic layer was washed with saturated saline and was then dried over anhydrous sodium sulfate, and the resultant product was subjected to distillation under reduced pressure. A crude product thus obtained was purified by silica gel column chromatography (hexane:ethyl acetate=1:1 to 1:2) to produce compound AP-A-1 (5.06 g, 87%) as a yellow foam-like solid substance.

$^1$H NMR (CDCl$_3$) δ 0.99-1.13 (28H, m), 1.90-1.98, 2.05-2.16 (2H, m), 2.68, 3.07 (2H, ABq, J=11 Hz), 2.81-2.90, 3.05-3.16 (2H, m), 3.51-3.63 (2H, m), 3.72, 4.04 (2H, ABq, J=13 Hz), 4.50 (1H, d, J=3 Hz), 4.82 (1H, d, J=3 Hz), 6.67 (1H, s), 7.09 (1H, m), 7.51-7.57 (2H, m), 7.60 (1H, m), 8.02-8.05 (2H, m), 8.36 (1H, s), 8.81 (1H, s), 9.10 (11H, s).

(Synthesis of Compound AP-A-2)

Compound AP-A-1 (5.05 g, 6.36 mmol) was dissolved in tetrahydrofuran (60 mL), then acetic acid (0.48 mL, 8.44 mmol) and tetra-n-butylammonium fluoride (a 1-M tetrahydrofuran solution, 13.7 mL, 13.7 mmol) were added in this order to the solution, and the resultant solution was stirred at room temperature for 20 minutes. The resultant reaction solution was subjected to distillation under reduced pressure, and a reaction residue was removed by silica gel column chromatography (ethyl acetate:methanol=30:1 to 10:1) to produce an intermediate. The intermediate was azeotropically dried with pyridine (40 mL). Subsequently, under a nitrogen stream, the resultant product was dissolved in pyridine (40 mL). 4,4'-Dimethoxytrityl chloride (2.86 g, 8.44 mmol) was added to the solution, and the resultant solution was stirred at room temperature for 14 hours. The reaction solution was cooled, then the reaction was terminated with an aqueous sodium bicarbonate solution and was then diluted with water and ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus obtained was purified by silica gel column chromatography (chloroform:methanol=60:1) to produce compound AP-A-2 (5.05 g, 91%) as a white foam-like solid substance.

$^1$H NMR (CDCl$_3$) δ 1.88-1.97, 2.07-2.13 (2H, m), 2.63 (1H, d, J=9 Hz), 2.79-2.88, 3.03-3.09 (2H, m), 2.94, 3.00 (2H, ABq, J=12 Hz), 3.38, 3.42 (2H, ABq, J=11 Hz), 3.50-3.63 (2H, m), 3.79 (6H, s), 4.46 (1H, dd, J=3.8 Hz), 4.73 (1H, d, J=3 Hz), 6.75 (1H, s), 6.81-6.86 (4H, m), 7.00 (1H, m), 7.20-7.46 (9H, m), 7.50-7.55 (2H, m), 7.59-7.64 (1H, m), 8.00-8.03 (2H, m), 8.36 (1H, s), 8.81 (1H, s), 9.14 (1H, s).

(Synthesis of Compound AP-A-3)

Under a nitrogen stream, compound AP-A-2 (5.05 g, 5.91 mmol) was azeotropically dried with acetonitrile, and the resultant product was dissolved in acetonitrile (67 mL). 4,5-Dicyanoimidazole (0.77 g, 6.50 mmol) and 2-cyanoethyl N,N,N',N'-tetraisopropylphosphordiamidite (2.4 mL, 7.33 mmol) were added in this order to the solution, and the resultant solution was stirred at room temperature for 2.5 hours. The reaction was terminated with an aqueous sodium bicarbonate solution, and the solution was diluted with water and ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus obtained was purified by silica gel column chromatography (hexane:ethyl acetate=45:55 to 20:80) to produce compound AP-A-3 (5.57 g, 89%) as a white foam-like solid substance.

$^{31}$P NMR (CDCl$_3$) δ 149.1, 149.4.

HRMS (MALDI): calcd for $C_{53}H_{59}F_3N_9NaO_9P$ [M+Na$^+$] 1076.4018, found 1076.4013.

Synthesis Example 4

A compound (1) wherein "Base" was an N-isobutyrylguanin-9-yl group, $A^1$ was a methylene group, $A^2$ was a single bond, X was a n-propylene group, $R^1$ was DMTr, $R^2$ was —P(N(i-Pr)$_2$)(OC$_2$H$_4$CN), and $R^3$ was a trifluoromethylcarbonylamino group (hereinafter, also referred to as "compound AP-G-2") was synthesized according to the reaction scheme shown below.

[Formula 54]

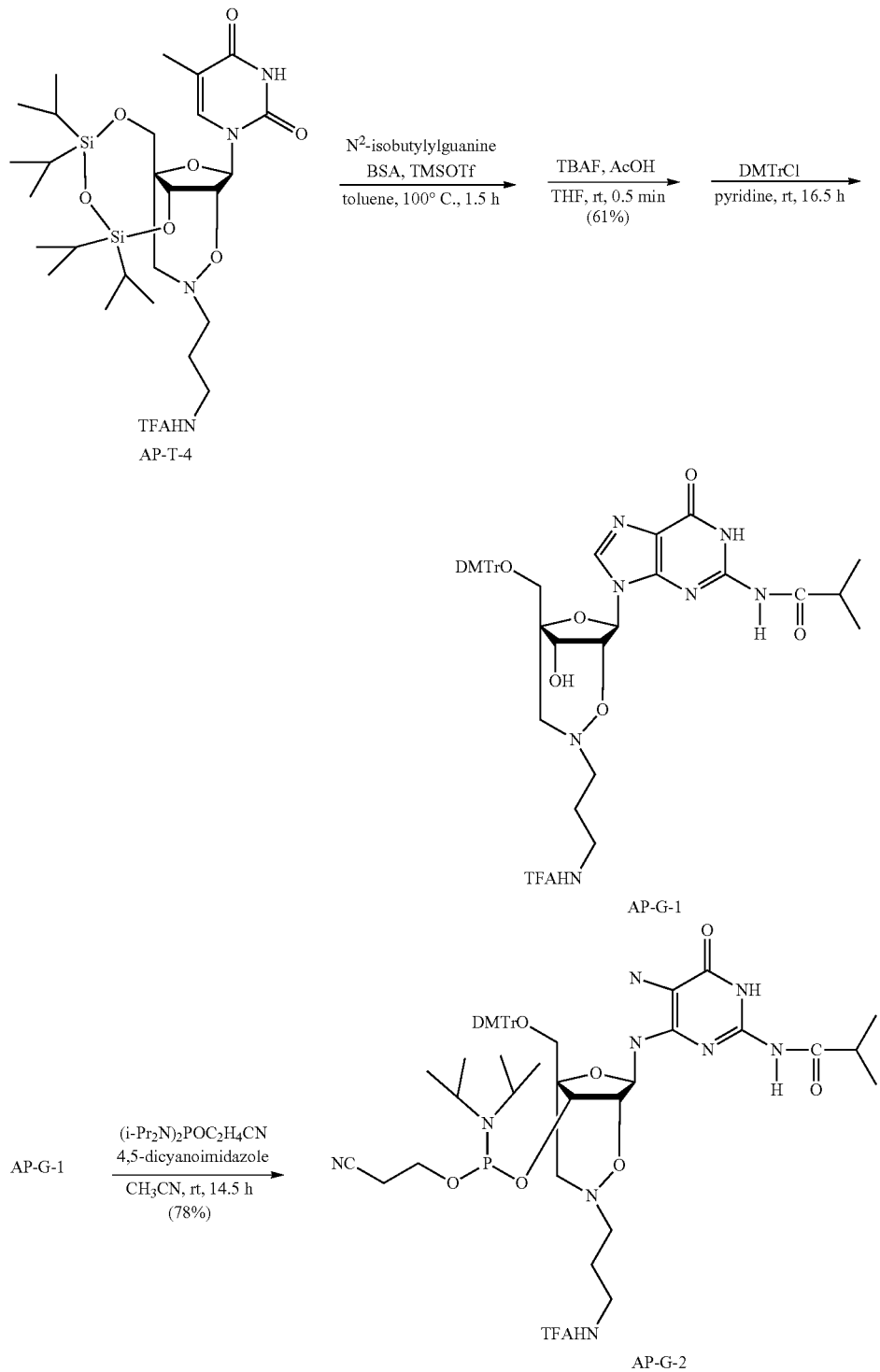

(Synthesis of Compound AP-G-1)

Under a nitrogen stream, compound AP-T-4 (9.31 g, 13.67 mmol) was dissolved in toluene (154 mL) at 60° C., then $N^2$-isobutyrylguanine (4.66 g, 21.06 mmol) and N,O-bis(trimethylsilyl)acetamide (22.3 mL, 90.24 mmol) were added in this order to the solution, and the resultant solution was stirred at 100° C. for 0.5 hour. Subsequently, trimethylsilyl trifluoromethanesulfonate (3.8 mL, 21.06 mmol) was added to the solution, and the resultant solution was stirred at 100° C. for 1 hour. The reaction solution was cooled, then the reaction was terminated with an aqueous sodium bicarbonate solution, then the resultant solution was diluted with ethyl acetate and water, and the reaction solution was subjected to filtration through celite to collect a filtrate. The collected filtrate was fractionated into an organic layer and an aqueous layer, the organic layer was washed with saturated saline and was then dried over anhydrous sodium sulfate, and the resultant product was subjected to distillation under reduced pressure. A reaction residue was removed from a crude product thus produced by silica gel column chromatography (hexane:ethyl acetate=1:1 to 1:2) to produce an intermediate. The resultant intermediate was dissolved in tetrahydrofuran (150 mL), then acetic acid (1.1 mL, 19.89 mmol) and tetra-n-butylammonium fluoride (a 1-M tetrahydrofuran solution, 27.8 mL, 27.8 mmol) were added in this order to the solution, and the resultant solution was stirred at room temperature for 30 minutes. The resultant reaction solution was subjected to distillation under reduced pressure, then a reaction residue was removed by silica gel column chromatography (ethyl acetate:methanol=15:1 to 7:1) to produce an intermediate. The intermediate was azeotropically dried with pyridine. Subsequently, under a nitrogen stream, the resultant product was dissolved in pyridine (120 mL). 4,4'-Dimethoxytrityl chloride (6.29 g, 18.56 mmol) was added, and the resultant solution was stirred at room temperature for 16.5 hours. The reaction solution was cooled, then the reaction was terminated with methanol, then the reaction solution was diluted with water and ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus obtained was purified by silica gel column chromatography (hexane:ethyl acetate=4:1 to ethyl acetate:methanol to 100:1, chloroform:methanol=98:2 to 96:4) to produce compound AP-G-1 (7.69 g, 61%) as a white foam-like solid substance.

$^1$H NMR (CDCl$_3$) δ 1.23 (6H, dd, J=2.7 Hz), 1.76-1.82, 2.18-2.22 (2H, m), 2.69-2.76 (1H, m), 2.78-2.87, 3.03-3.07 (2H, m), 2.97, 3.02 (2H, ABq, J=12 Hz), 3.20 (1H, d, J=8 Hz), 3.36-3.48, 4.07-4.18 (2H, m), 3.41, 3.46 (2H, ABq, J=11 Hz), 3.77 (6H, s), 4.22 (1H, d, J=3 Hz), 4.36 (1H, dd, J=3.7 Hz), 6.80-6.84 (5H, m), 6.97 (1H, m), 7.16-7.50 (9H, m), 7.83 (1H, s), 9.82 (1H, s), 12.14 (1H, s).

(Synthesis of Compound AP-G-2)

Under a nitrogen stream, compound AP-G-1 (7.52 g, 9.00 mmol) was azeotropically dried with acetonitrile, and the resultant product was dissolved in acetonitrile (91 mL). 4,5-Dicyanoimidazole (1.18 g, 10.0 mmol) and 2-cyanoethyl N,N,N',N'-tetraisopropylphosphordiamidite (3.5 mL, 10.91 mmol) were added in this order to the solution, and the resultant solution was stirred at room temperature for 14.5 hours. The reaction solution was cooled, then the reaction was terminated with an aqueous sodium bicarbonate solution and was then diluted with water and ethyl acetate, and the resultant solution was fractionated to obtain an organic layer. The organic layer was washed with saturated saline, and was then dried over anhydrous sodium sulfate, and the dried product was subjected to distillation under reduced pressure. A crude product thus obtained was purified by was purified by silica gel column chromatography (hexane:ethyl acetate=45:55 to 20:80) to produce compound AP-G-2 (7.27 g, 78%) as a white foam-like solid substance. $^{31}$P NMR (CDCl$_3$) δ 149.1, 149.2.

HRMS (MALDI): calcd for $C_{50}H_{61}F_3N_9NaO_{10}P$ [M+Na$^+$] 1058.4123, found 1058.4139.

Synthesis Example 5

A compound (1) wherein "Base" was a thymin-1-yl group, A$^1$ was a methylene group, A$^2$ was a single bond, X was a n-propylene group, R$^1$ was DMTr, R$^2$ was —P(N(i-Pr)$_2$)(OC$_2$H$_4$CN), and R$^3$ was a dimethylamino group (hereinafter, also referred to as "compound DT-3") was synthesized according to the reaction scheme shown below.

[Formula 55]

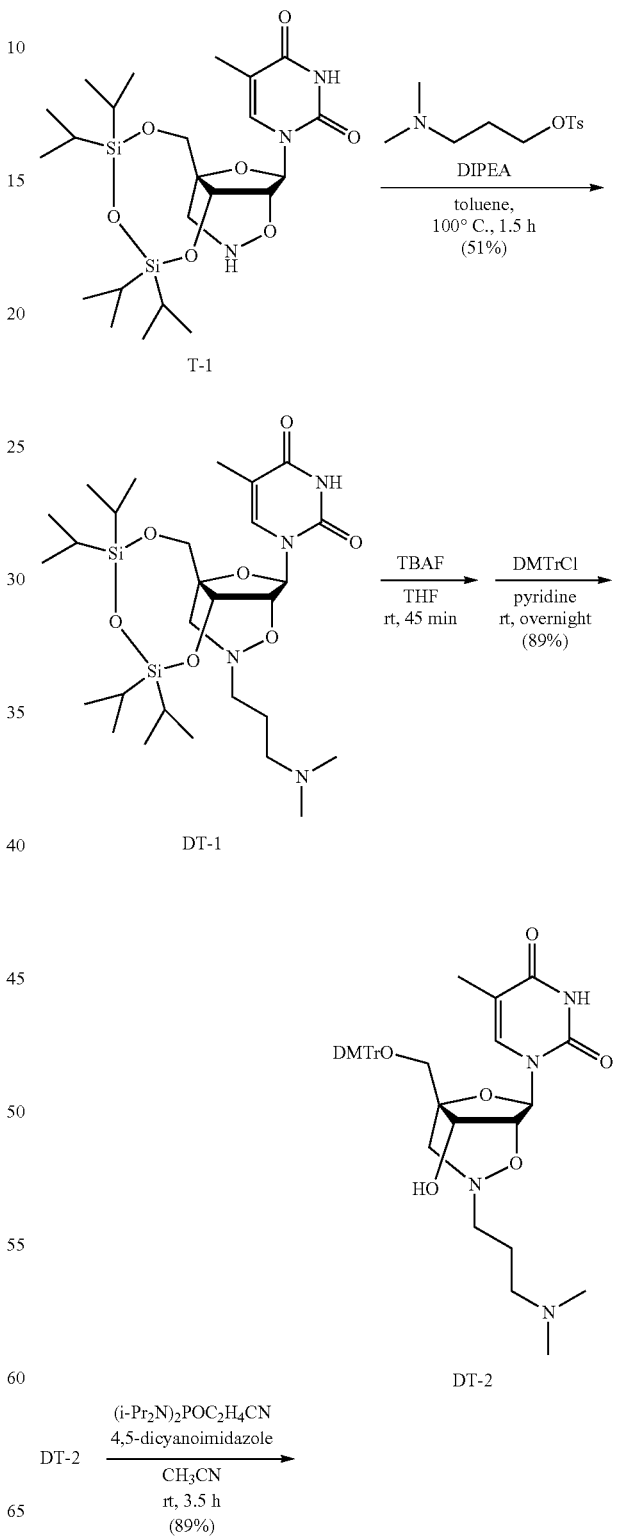

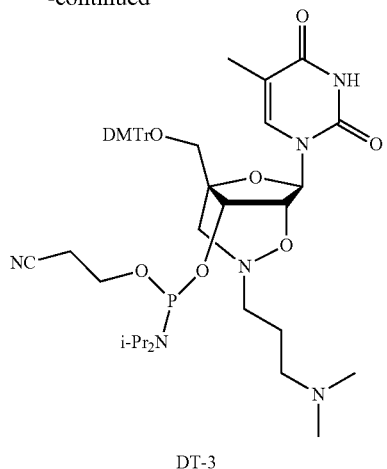

DT-3

(Synthesis of Compound DT-1)

Under a nitrogen stream, 3-(dimethylamino)-1-propanol (15.9 mL, 136.2 mmol) was added dropwise slowly to a suspension of sodium hydride (60% in oil, 4.58 g, 11.45 mmol) in toluene (200 mL) under ice cooling, and the resultant solution was stirred under ice cooling for 30 minutes. Subsequently, p-toluenesulfonyl chloride (21.67 g, 113.7 mmol) was added in three portions, then an ice bath was removed, and the solution was stirred at room temperature for 2 hours and 30 minutes. Subsequently, the solution was placed under ice cooling, then 3-(dimethylamino)-1-propanol (3.0 mL, 25.7 mmol) was added dropwise slowly, and the resultant solution was stirred at room temperature for 35 minutes. Subsequently, the solution was placed under ice cooling again, then 3-(dimethylamino)-1-propanol (1.0 mL, 8.6 mmol) was added dropwise slowly, and the resultant solution was stirred at room temperature for 30 minutes. Water was added under ice cooling, and the resultant solution was extracted with toluene, and then an organic layer thus obtained was washed with saturated saline and was then dried over anhydrous sodium sulfate. Anhydrous sodium sulfate was removed by filtration, then the resultant solution was subjected to distillation under reduced pressure until a filtrate was made slightly cloudy, then a solution of 3-(dimethylamino)-1-propyl p-toluenesulfonate in toluene thus obtained was used in the subsequent reaction without any modification.

N,N-Diisodiisopropylethylamine (30 mL, 175 mmol) was added to a solution of compound T-1 (40 g, 75.8 mmol) in toluene (240 mL) at room temperature, and the reaction solution was warmed to 100° C. A 3-(dimethylamino)-1-propyl p-toluenesulfonate in toluene which had been prepared previously was added dropwise over 1 hour and 10 minutes, and was then further stirred at 100° C. for 30 minutes. Subsequently, the reaction solution was cooled to room temperature, then a solvent was distilled away under reduced pressure to produce a residue, and the residue was purified by silica gel column chromatography (ethyl acetate:triethylamine:methanol=20:1:0 to 20:1:2) to produce compound DT-1 (23.47 g, 51%) as a white foam-like solid substance.

$^1$H NMR (DMSO-$d_6$) δ 0.90-1.12 (28H, m), 1.61-1.83 (2H, m), 1.74 (3H, s), 2.11 (6H, s), 2.19-2.34 (2H, m), 2.69-2.81 (4H, m), 3.64 (1H, d, J=13 Hz), 3.92 (1H, d, J=3 Hz), 4.04 (1H, d, J=13 Hz), 4.36 (1H, d, J=3 Hz), 6.11 (1H, s), 7.49 (1H, s), 11.40 (1H, brs).

(Synthesis of Compound DT-2)

Under a nitrogen stream, tetra-n-butylammonium fluoride (a 1-M tetrahydrofuran solution, 10.3 mL, 10.3 mmol) was added to a solution of compound DT-1 (3.00 g, 4.90 mmol) in tetrahydrofuran (60 mL) under ice cooling, and the resultant solution was stirred at room temperature for 45 minutes. A residue obtained by the distillation of the solvent away under reduced pressure was subjected to alumina column chromatography (chloroform:methanol=7:1 to 6:1) using a short column to remove a reaction residue, thereby producing an intermediate. The intermediate was azeotropically distilled with pyridine and then with a pyridine: toluene (=1:1) mixed solution, then the intermediate was dissolved in pyridine (60 mL), then 4,4'-dimethoxytrityl chloride (4.31 g, 12.72 mmol) was added under ice cooling, then an ice bath was removed, and the solution was stirred overnight at room temperature. Next morning, an aqueous sodium bicarbonate solution was added under ice cooling, then the resultant solution was diluted with water, and then the distilled solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by alumina column chromatography (chloroform:methanol=1:0 to 10:1) and then by silica gel column chromatography (ethyl acetate:methanol:triethylamine=20: 1:1 to 20:2:1) to produce compound DT-2 (2.92 g, 89%) as a white foam-like solid substance (a portion thereof was a pale yellow foam-like solid substance).

$^1$H NMR (CDCl$_3$) δ 1.44 (3H, s), 1.63-1.90 (2H, m), 2.22 (6H, s), 2.29-2.46 (2H, m), 2.78-2.96 (2H, m), 2.73 (1H, d, J=12 Hz), 2.85 (1H, d, J=12 Hz), 3.33 (1H, d, J=11 Hz), 3.37 (1H, d, J=12 Hz), 3.79 (6H, s), 4.24 (1H, d, J=3 Hz), 4.36 (1H, d, J=3 Hz), 6.33 (1H, s), 6.83-6.86 (4H, m), 7.21-7.46 (9H, m), 7.76 (1H, s).

(Synthesis of Compound DT-3)

Under a nitrogen stream, 4,5-dicyanoimidazole (0.354 g, 3.00 mmol) and 2-cyanoethyl N,N,N',N'-tetraisopropylphosphordiamidite (1.20 mL, 3.78 mmol) were added to a solution of compound DT-2 (1.68 g, 2.50 mmol) in acetonitrile (40 mL) under ice cooling, and the resultant solution was stirred at room temperature for 3 hours and 30 minutes. An aqueous sodium bicarbonate solution was added under ice cooling, then the solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:methanol:triethylamine=20:0:1 to 20:2:1) to produce compound DT-3 (1.95 g, 89%) as a white foam-like solid substance. $^{31}$P NMR (DMSO-$d_6$) δ 148.62, 147.25.

HRMS (MALDI): calcd for $C_{46}H_{61}N_6NaO_9P$ [M+Na$^+$] 895.4130, found 895.4117.

Synthesis Example 6

A compound (1) wherein "Base" was an N-benzoyl-5-methylcytosin-1-yl group, $A^1$ was a methylene group, $A^2$ was a single bond, X was a n-propylene group, $R^1$ was DMTr, $R^2$ was —P(N(i-Pr)$_2$)(OC$_2$H$_4$CN), and $R^3$ was a dimethylamino group (hereinafter, also referred to as "compound DC-3") was synthesized according to the reaction scheme shown below.

[Formula 56]

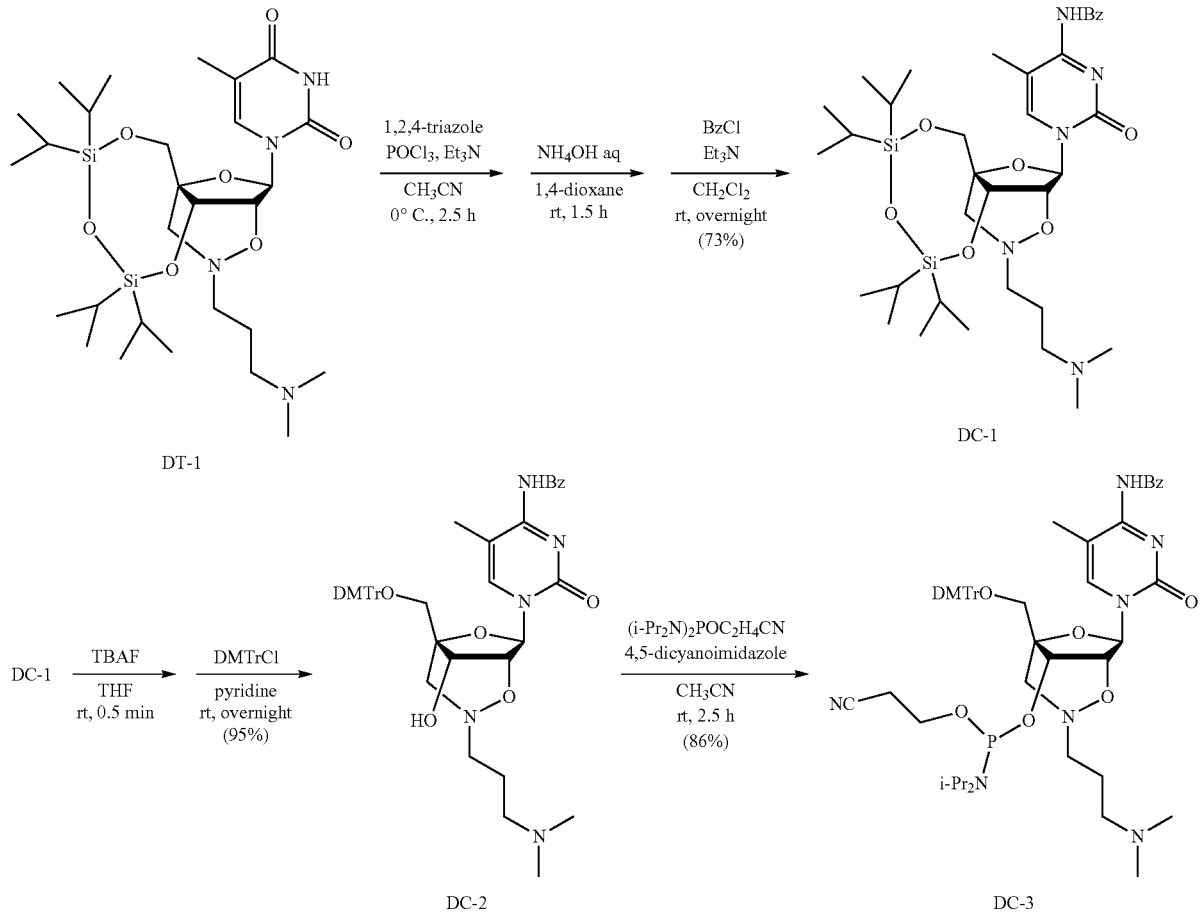

(Synthesis of Compound DC-1)

Under a nitrogen stream, triethylamine (10.9 ml, 78.4 mmol) and 1,2,4-triazole (3.61 g, 52.2 mmol) were added to a solution of compound DT-1 (4.0 g, 6.53 mmol) in acetonitrile (60 mL) under ice cooling, then phosphoryl chloride (1.25 ml, 13.41 mmol) was added dropwise to the solution slowly, and then the resultant solution was stirred while ice-cooling for 2 hours and 30 minutes. Subsequently, an aqueous sodium bicarbonate solution was added to the solution while ice-cooling, the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a white solid substance (4.94 g). Subsequently, the white solid substance was dissolved in 1,4-dioxane (60 mL), then a 28% aqueous ammonia solution (15 ml) was added to the solution, and the stirring of the resultant solution was continued at room temperature for 1 hour and 30 minutes. The solvent was distilled away under reduced pressure to obtain a residue, the residue was azeotropically distilled once with a (pyridine:toluene=1:1) mixed solvent and was then dissolved in dichloromethane (60 mL), then triethylamine (1.72 ml, 12.37 mmol) and benzoyl chloride (1.14 ml, 9.89 mmol) were added to the solution under ice cooling, and the resultant solution was stirred at room temperature overnight. Under ice cooling, an aqueous sodium bicarbonate solution was added to the solution, the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to obtain a crude product, and the crude product was purified by silica gel column chromatography (ethyl acetate:methanol:triethylamine=100:0:1 to 80:1:1) to produce compound DC-1 (3.42 g, 73%) as a white foam-like solid substance.

$^1$H NMR (DMSO-$d_6$) δ 0.92-1.12 (28H, m), 1.62-1.75 (2H, m), 1.99 (3H, d, J=1 Hz), 2.11 (6H, s), 2.19-2.32 (2H, m), 2.67-2.83 (2H, m), 2.73 (1H, d, J=11 Hz), 2.81 (1H, d, J=12 Hz), 3.65 (1H, d, J=13 Hz), 3.91 (1H, d, J=3 Hz), 4.07 (1H, d, J=13 Hz), 4.43 (1H, d, J=3 Hz), 6.13 (1H, s), 7.46-7.51 (2H, m), 7.56-7.61 (1H, m), 7.78 (1H, d, J=1 Hz), 8.14-8.17 (2H, m), 12.8 (1H, brs).

(Synthesis of Compound DC-2)

Under a nitrogen stream, tetra-n-butylammonium fluoride (a 1-M tetrahydrofuran solution, 3.55 mL, 3.55 mmol) was added to a solution of compound DC-1 (1.21 g, 1.69 mmol) in tetrahydrofuran (25 mL) under ice cooling, and the resultant solution was stirred at room temperature for 30 minutes. A residue obtained by the distillation of the solvent away under reduced pressure was subjected to alumina column chromatography (chloroform:methanol=15:1) using a short column to remove a reaction residue, thereby producing an intermediate. The intermediate was azeotropically distilled once with pyridine and then once with a pyridine:toluene (=1:1) mixed solution, then the intermediate was dissolved in pyridine (32 mL), then 4,4'-dimethoxytrityl chloride (1.26 g, 3.72 mmol) was added to the solution under ice cooling, and the resultant solution was stirred overnight at room temperature while removing an ice bath. Next morning, 4,4'-dimethoxytrityl chloride (0.23 g, 0.68 mmol) was added to the solution under ice cooling, and the resultant solution was stirred at room temperature for 3 hours. Under ice cooling, an aqueous sodium bicarbonate solution was added to the solution, the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by alumina column chromatography (chloroform:methanol=100:1 to 30:1) to produce compound DC-2 (1.25 g, 95%) as a yellow foam-like solid substance.

$^1$H NMR (DMSO-$d_6$) δ 1.54 (3H, s), 1.60-1.76 (2H, m), 2.12 (6H, s), 2.19-2.34 (2H, m), 2.63-2.87 (4H, m), 3.23 (1H, d, J=11 Hz), 3.27 (1H, d, J=11 Hz), 3.75 (6H, s), 4.08-4.11 (1H, m), 4.33 (1H, d, J=3 Hz), 5.63 (1H, d, J=5 Hz), 6.16 (1H, s), 6.91-6.95 (4H, m), 7.24-7.52 (11H, m), 7.57-7.62 (1H, m), 7.93 (1H, s), 8.13-8.16 (2H, m), 12.8 (1H, brs).

(Synthesis of Compound DC-3)

Under a nitrogen stream, 4,5-dicyanoimidazole (0.417 g, 3.53 mmol) and 2-cyanoethyl N,N,N',N'-tetraisopropylphosphordiamidite (1.40 mL, 4.41 mmol) were added to a solution of compound DC-2 (2.28 g, 2.94 mmol) in acetonitrile (47 mL) under ice cooling, and the resultant solution was stirred at room temperature for 2 hours and 30 minutes. Subsequently, under ice cooling, an aqueous sodium bicarbonate solution was added to the solution, then the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:triethylamine=30:1 to 20:1) to produce compound DC-3 (2.46 g, 86%) as a white foam-like solid substance.

$^{31}$P NMR (DMSO-$d_6$) δ 148.89, 147.22.

HRMS (MALDI): calcd for $C_{53}H_{66}N_7NaO_9P[M+Na^+]$ 998.4552, found 998.4556.

Synthesis Example 7

A compound (1) wherein "Base" was an N-benzoyladenin-9-yl group, $A^1$ was a methylene group, $A^2$ was a single bond, X was a n-propylene group, $R^1$ was DMTr, $R^2$ was —P(N(i-Pr)$_2$)(OC$_2$H$_4$CN) and $R^3$ was a dimethylamino group (hereinafter, also referred to as "compound DA-3") was synthesized according to the reaction scheme shown below.

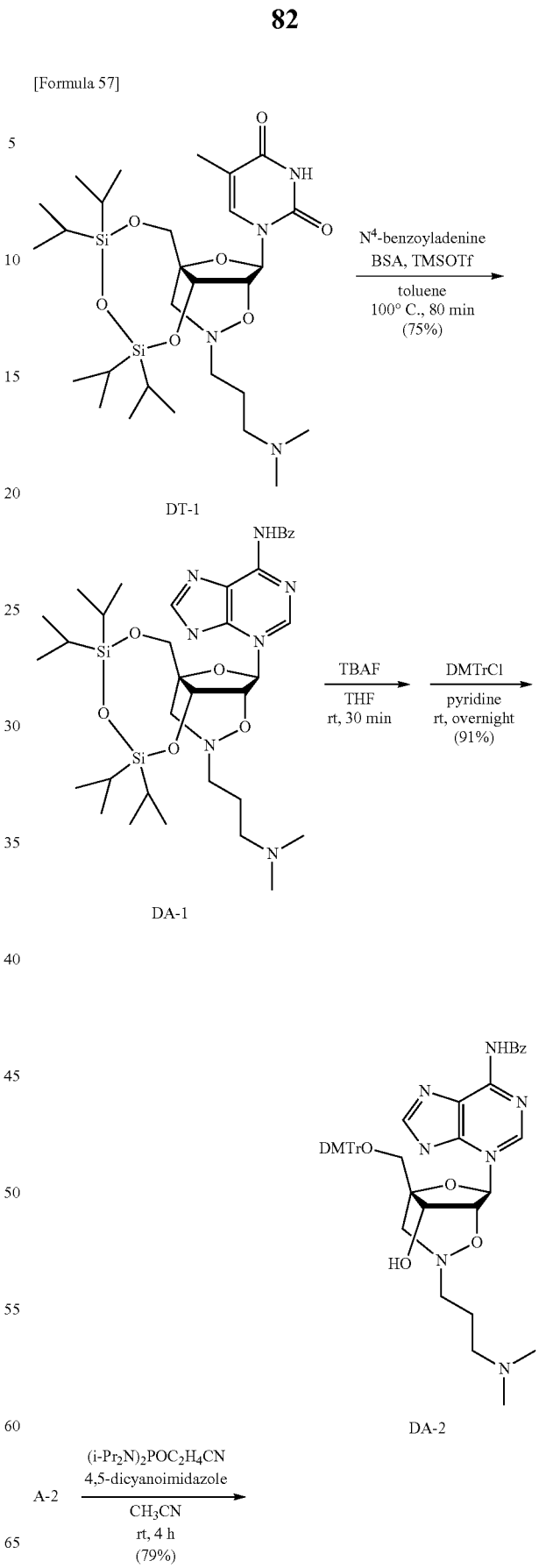

-continued

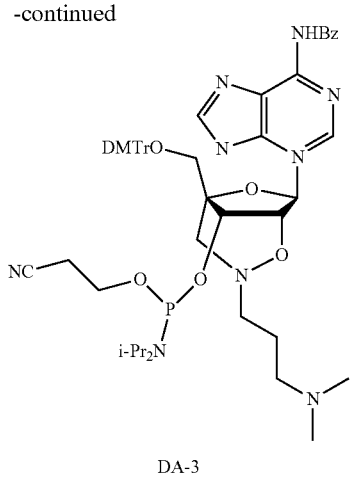

DA-3

(Synthesis of Compound DA-1)

Under a nitrogen stream, N$_6$-benzoyladenine (0.820 g, 3.43 mmol) and N,O-bis(trimethylsilyl)acetamide (3.25 mL, 13.2 mmol) were added in this order to a solution of compound DT-1 (2.00 g, 3.26 mmol) in toluene (35 mL), the resultant solution was warmed to 100° C. and was then stirred at 100° C. for 20 minutes. Subsequently, the solution was stirred the under room temperature for 5 minutes, then trimethylsilyl trifluoromethanesulfonate (0.620 mL, 3.43 mmol) was added dropwise to the solution, the resultant solution was warmed to 100° C. and was then stirred at 100° C. for 1 hour and 20 minutes. Subsequently, an aqueous sodium bicarbonate solution was added to the solution under ice cooling, then the resultant solution was diluted with water and ethyl acetate, and the diluted solution was filtrated through celite. A filtrate was extracted with ethyl acetate, then an organic layer thus obtained was washed with saturated saline and was then dried over anhydrous sodium sulfate. Anhydrous sodium sulfate was removed by filtration, and then a filtrate was subjected to distillation under reduced pressure to produce a crude product, and the crude product was purified by alumina column chromatography (chloroform:methanol=50:1) to produce compound DA-1 (1.78 g, 75%) as a yellow foam-like solid substance. $^1$H NMR (DMSO) 0.93-1.17 (28H, m), 1.71-1.78 (2H, m), 2.15 (6H, s), 2.25-2.38 (2H, m), 2.77-2.92 (4H, m), 3.68 (1H, d, J=13 Hz), 4.00 (1H, d, J=13 Hz), 4.62 (1H, d, J=3 Hz), 4.98 (1H, d, J=3 Hz), 6.71 (1H, s), 7.54-7.57 (2H, m), 7.63-7.67 (1H, m), 8.03-8.06 (2H, m), 8.44 (1H, s), 8.69 (1H, s), 11.3 (1H, brs).

(Synthesis of Compound DA-2)

Under a nitrogen stream, tetra-n-butylammonium fluoride (a 1-M tetrahydrofuran solution, 3.65 mL, 3.65 mmol) was added to a solution of compound DA-1 (1.26 g, 1.74 mmol) in tetrahydrofuran (32 mL) under ice cooling, and the resultant solution was stirred at room temperature for 30 minutes. A residue obtained by the distillation of the solvent away under reduced pressure was subjected to alumina column chromatography (chloroform:methanol=10:1) using a short column to remove a reaction residue, thereby producing an intermediate. The intermediate was azeotropically distilled with pyridine and then with a pyridine:toluene (=1:1) mixed solution, then the intermediate was dissolved in pyridine (32 mL), 4,4'-dimethoxytrityl chloride (1.18 g, 3.48 mmol) was added to the solution under ice cooling, and the resultant solution was stirred overnight at room temperature while removing an ice bath. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:methanol:triethylamine=20: 0:1 to 20:4:1) to produce compound DA-2 (1.24 g, 91%) as a white foam-like solid substance.

$^1$H NMR (DMSO) δ 1.69-1.79 (2H, m), 2.15 (6H, s), 2.24-2.40 (2H, m), 2.73-2.98 (4H, m), 3.18 (1H, d, J=11 Hz), 3.27-3.32 (1H, m), 3.72 (6H, s), 4.40-4.43 (1H, m), 4.68 (1H, d, J=3 Hz), 5.52 (1H, d, J=6 Hz), 6.73 (1H, s), 6.84-6.87 (4H, m), 7.19-7.41 (9H, m), 7.52-7.58 (2H, m), 7.62-7.68 (1H, m), 8.03-8.06 (2H, m), 8.52 (1H, s), 8.78 (1H, s), 11.2 (1H, brs).

(Synthesis of Compound DA-3)

Under a nitrogen stream, 4,5-dicyanoimidazole (34.5 mg, 0.29 mmol) and 2-cyanoethyl N,N,N',N'-tetraisopropylphosphorodiamidite (0.116 mL, 0.37 mmol) were added to a solution of compound DA-2 (191.3 mg, 0.24 mmol) in acetonitrile (5 mL) under ice cooling, and the resultant solution was stirred at room temperature for 4 hours. Subsequently, an aqueous sodium bicarbonate solution was added under ice cooling, then the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by alumina column chromatography (chloroform:methanol=80:1) to produce compound DA-3 (189.8 mg, 79%) as a pale yellow foam-like solid substance (partly a white foam-like solid substance).

$^{31}$P NMR (DMSO-d$_6$) δ 148.76, 148.06.

HRMS (MALDI): calcd for C$_{53}$H$_{64}$N$_9$NaO$_8$P [M+Na$^+$] 1008.4508, found 1008.4513.

Synthesis Example 8

A compound (1) wherein "Base" was an N-isobutyrylguanin-9-yl group, A$^1$ was a methylene group, A$^2$ was a single bond, X was a n-propylene group, R$^1$ was DMTr, R$^2$ was —P(N(i-Pr)$_2$)(OC$_2$H$_4$CN) and R$^3$ was a dimethylamino group (hereinafter, also referred to as "compound DG-3") was synthesized according to the reaction scheme shown below.

[Formula 58]
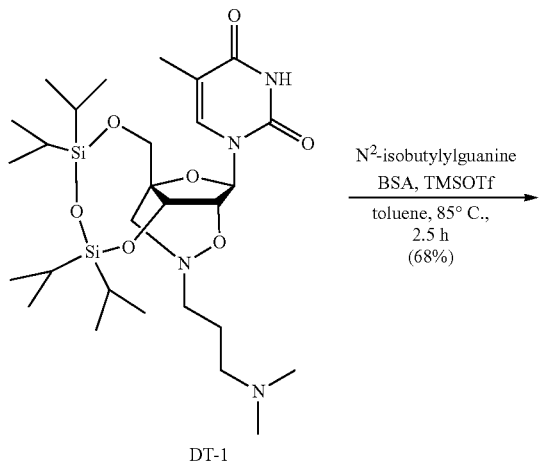
DT-1
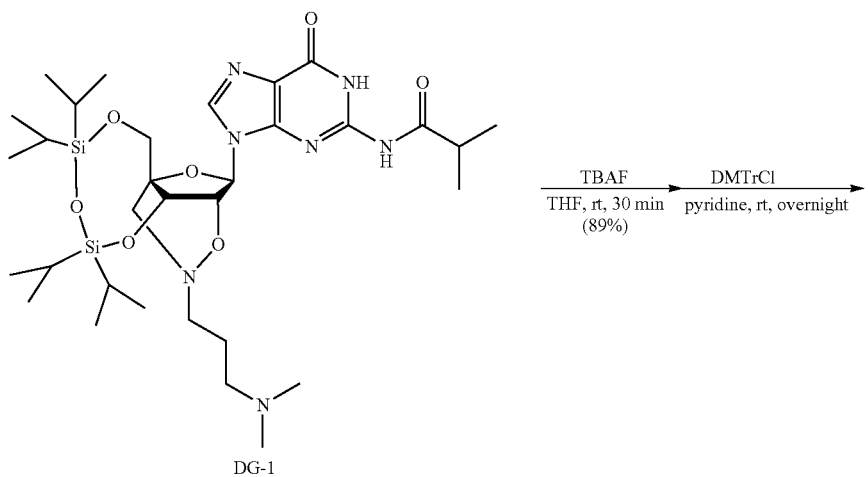
DG-1
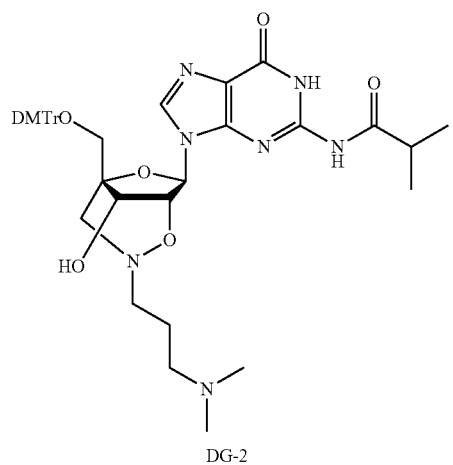
DG-2

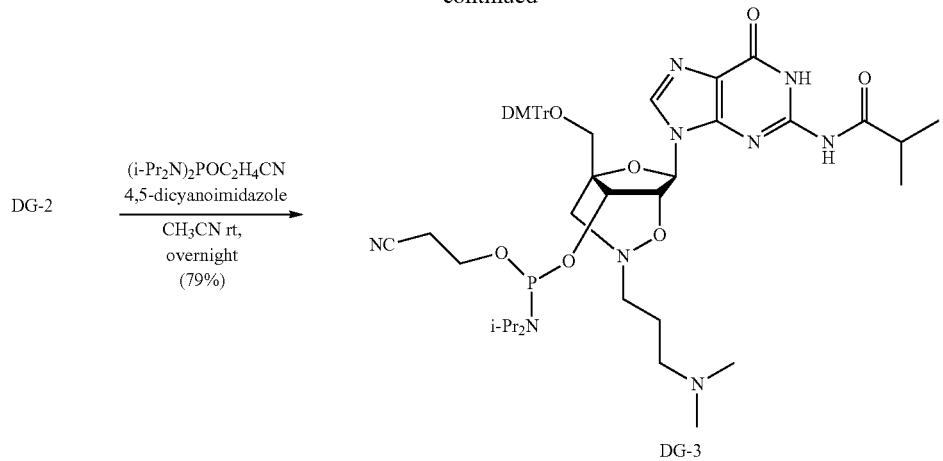

(Synthesis of Compound DG-1)

Under a nitrogen stream, N2-isobutyrylguanine (65.3 mg, 0.30 mmol) and N,O-bis(trimethylsilyl)acetamide (0.275 ml, 1.113 mmol) were added in this order to a solution of compound DT-1 (113.1 mg, 0.18 mmol) in toluene (2.0 mL), the resultant solution was warmed to 95° C. and was then stirred at 95° C. for 50 minutes. Subsequently, the solution was stirred under room temperature for 5 minutes, then trimethylsilyl trifluoromethanesulfonate (0.052 mL, 0.29 mmol) was added dropwise to the solution, and the resultant solution was stirred at 95° C. for 2 hours and 30 minutes. Subsequently, an aqueous sodium bicarbonate solution was added to the solution under ice cooling, then the resultant solution was diluted with water and ethyl acetate, and the diluted solution was filtrated through celite. A filtrate thus obtained was extracted with ethyl acetate, an organic layer thus obtained was washed with saturated saline and was then dried over anhydrous sodium sulfate. Anhydrous sodium sulfate was removed by filtration, and then a filtrate was subjected to distillation under reduced pressure to produce a crude product, and the crude product was purified by alumina column chromatography (chloroform:methanol=30:1 to 20:1) to produce compound DG-1 (88.8 mg, 68%) as a yellow foam-like solid substance.

$^1$H NMR (DMSO-d$_6$) δ 0.93-1.09 (28H, m), 1.12 (6H, d, J=7 Hz), 1.67-1.71 (2H, m), 2.13 (6H, s), 2.20-2.37 (2H, m), 2.73-2.89 (5H, m), 3.68 (1H, d, J=13 Hz), 4.03 (1H, d, J=13 Hz), 4.21 (1H, d, J=3 Hz), 4.70 (1H, d, J=3 Hz), 6.40 (1H, s), 7.91 (1H, s), 12.2 (1H, brs).

(Synthesis of Compound DG-2)

Under a nitrogen stream, tetra-n-butylammonium fluoride (a 1-M tetrahydrofuran solution, 7.6 mL, 7.6 mmol) was added to a solution of compound DG-1 (2.56 g, 3.61 mmol) in tetrahydrofuran (58 mL) under ice cooling, and the resultant solution was stirred at room temperature for 30 minutes. Subsequently, a residue obtained by the distillation of the solvent away under reduced pressure was subjected to alumina column chromatography (chloroform:methanol=8:1 to 5:1) using a short column to remove a reaction residue, thereby producing an intermediate. The intermediate was azeotropically distilled with pyridine and then with a pyridine:toluene (=1:1) mixed solution, then the intermediate was dissolved in pyridine (60 mL), then 4,4'-dimethoxytrityl chloride (3.18 g, 9.40 mmol) was added under ice cooling, and the resultant solution was stirred overnight at room temperature while removing an ice bath. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (chloroform:methanol=50:1 to 7:1), and was then purified by silica gel column chromatography (chloroform:methanol=15:1 to 5:1) to produce compound DG-2 (2.47 g, 89%) as a white foam-like solid substance.

$^1$H NMR (DMSO-d6) δ 1.12 (6H, dd, J=1.2 Hz, J=6.8 Hz), 1.78-1.86 (2H, m), 2.43 (6H, brs), 2.67 (1H, brs), 2.77-2.94 (4H, m), 3.14-3.22 (5H, m), 3.73 (6H, s), 4.25 (1H, brs), 4.62 (1H, d, J=2.8 Hz), 5.57 (1H, brs), 6.45 (1H, s), 6.84-6.88 (4H, m), 7.20-7.38 (9H, m), 8.08 (1H, s), 12.15 (1H, brs).

(Synthesis of Compound DG-3)

Under a nitrogen stream, 4,5-dicyanoimidazole (0.21 g, 1.75 mmol) and 2-cyanoethyl N,N,N',N'-tetraisopropylphosphorodiamidite (0.69 mL, 2.18 mmol) were added to a solution of compound DG-2 (1.11 g, 1.45 mmol) in acetonitrile (50 mL) under ice cooling, and the resultant solution was stirred at room temperature overnight. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:methanol:triethylamine=20:0:1 to 20:2:1) to produce compound DG-3 (1.11 g, 79%) as a white foam-like solid substance.

$^{31}$P NMR (DMSO-d$_6$) δ 148.97, 147.81.

HRMS (MALDI): calcd for $C_{50}H_{66}N_9NaO_9P$ [M+Na$^+$] 990.4613, found 990.4604.

Synthesis Example 9

A compound (1) wherein "Base" was a thymin-1-yl group, A$^1$ was a methylene group, A$^2$ was a single bond, X was a n-hexylene group, $R^1$ was DMTr, $R^2$ was —P(N(i-Pr)$_2$)(OC$_2$H$_4$CN), and $R^3$ was a dimethylamino group (hereinafter, also referred to as "compound DH-3") was synthesized according to the reaction scheme shown below.

[Formula 59]

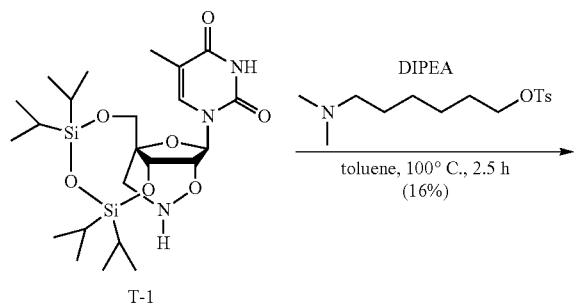

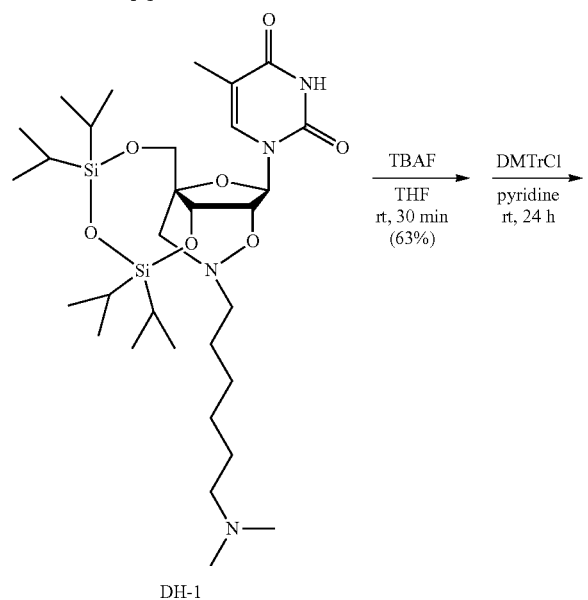

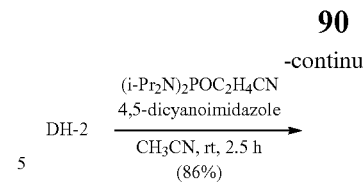

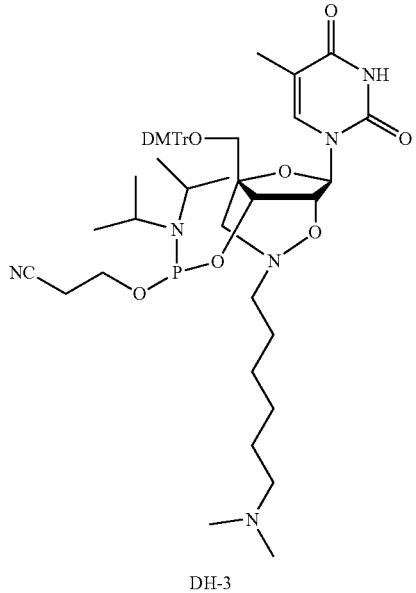

(Synthesis of Compound DH-1)

Under a nitrogen stream, sodium hydride (2.27 g, 56.82 mmol) was suspended in toluene (86 mL), then 6-dimethylamino-1-hexanol (8.6 mL, 51.65 mmol) was added to the solution, and the resultant solution was stirred under ice cooling for 30 minutes. Subsequently, p-toluenesulfonyl chloride (10.83 g, 56.82 mmol) was added to the solution, and the resultant solution was stirred for 4 hours under room temperature while adding 6-dimethylamino-1-hexanol (7.38 mL, 44.44 mmol) in three divided portions. The reaction solution was cooled, then the reaction was terminated with water, the resultant solution was diluted with toluene, and the diluted solution was fractionated into an organic layer and an aqueous layer. The organic layer was washed with saturated saline, and then the organic layers were combined together, and the resultant solution was dried over anhydrous sodium sulfate distillation under reduced pressure to produce a solution of 3-(dimethylamino)-1-hexyl p-toluenesulfonate in toluene (90 mL).

Under a nitrogen stream, compound T-1 (5.0 g, 9.47 mmol) was dissolved in toluene (35 mL), then N,N-diisopropylamine (13.1 mL, 75.76 mmol) was added to the solution, then the solution of 3-(dimethylamino)-1-hexyl p-toluenesulfonate in toluene which had been prepared previously at 100° C. was added dropwise over 1.5 hours, and the resultant solution was stirred under this condition for 1 hour. The reaction solution was cooled to room temperature, then the solution was filtrated to collect a filtrate. The collected filtrate was subjected to distillation under reduced pressure to produce a crude product, and the crude product was purified by silica gel column chromatography (hexane:ethyl acetate:triethylamine=16:4:1 to 20:1:1) to produce compound DH-1 (1.02 g, 16%) as a pale yellow foam-like solid substance.

$^1$H NMR (DMSO-d6) δ 0.95-1.14 (28H, m), 1.29-1.54 (8H, m), 1.74 (3H, d, J=1 Hz), 2.09 (6H, s), 2.16 (3H, t, J=7 Hz), 2.70, 2.78 (2H, ABq, J=11 Hz), 2.61-2.83 (2H, m), 3.64, 4.04 (2H, ABq, J=13 Hz), 3.92 (1H, d, J=3 Hz), 4.35 (1H, d, J=3 Hz), 6.10 (1H, s), 7.49 (1H, d, J=1 Hz), 11.34 (1H, s).

(Synthesis of Compound DH-2)

Compound DH-1 (1.02 g, 1.55 mmol) was dissolved in tetrahydrofuran (10 mL), then tetra-n-butylammonium fluoride (a 1-M tetrahydrofuran solution, 3.3 mL, 3.3 mmol) was added, and the resultant solution was stirred at room temperature for 30 minutes. The reaction solution was subjected to distillation under reduced pressure, then a reaction residue was removed by silica gel column chromatography (chloroform:methanol=10:1 to 8:1) to produce an intermediate. The intermediate was azeotropically dried with pyridine. Subsequently, under a nitrogen stream, the resultant product was dissolved in pyridine (20 mL). 4,4'-Dimethoxytrityl chloride (1.05 g, 3.10 mmol) was added to the solution, and the resultant solution was stirred at room temperature for 14.5 hours. 4,4'-Dimethoxytrityl chloride (1.05 g, 3.10 mmol) was further added to the solution, the resultant solution was stirred at room temperature for 9 hours, then 4,4'-dimethoxytrityl chloride (0.54 g, 1.59 mmol) was further added, and the resultant solution was stirred at room temperature for 15 hours. The reaction solution was cooled, then the reaction was terminated with methanol, then the reaction solution was diluted with water and ethyl acetate, and the resultant solution was fractionated to obtain an organic layer. The organic layer was washed with an aqueous sodium bicarbonate solution and saturated saline and was then dried over anhydrous sodium sulfate, and the dried product was subjected to distillation under reduced pressure. A crude product thus obtained was purified by silica gel column chromatography (ethyl acetate:methanol:triethylamine=20:1:1 to 20:3:1) to produce compound DH-2 (0.70 g, 63%) as a pale yellow foam-like solid substance.

$^1$H NMR (DMSO-d6) δ 1.27-1.50 (8H, m), 1.31 (3H, s), 2.08 (6H, s), 2.15 (2H, t, J=7 Hz), 2.57-2.68, 2.72-2.84 (2H, m), 2.72 (2H, s), 3.20 (2H, s), 3.74 (6H, s), 4.04-4.06 (1 H, m), 4.21 (2H, d, J=3 Hz), 5.54 (1H, d, J=5 Hz), 6.11 (1H, s), 7.22-7.44 (9H, m), 7.62 (1H, d, J=1 Hz), 11.25 (1H, s).

(Synthesis of Compound DH-3)

Under a nitrogen gas stream, compound DH-2 (294 mg, 0.41 mmol) was azeotropically dried with acetonitrile, and the resultant product was dissolved in acetonitrile (4.5 mL). 4,5-Dicyanoimidazole (54 mg, 0.46 mmol) and 2-cyanoethyl N,N,N',N'-tetraisopropylphosphordiamidite (164 μL, 0.50 mmol) were added in this order to the solution, and the resultant solution was stirred at room temperature for 2.5 hours. The reaction solution was cooled, then the reaction was terminated with an aqueous sodium bicarbonate solution, then the resultant solution was diluted with ethyl acetate and water, and the diluted solution was fractionated to obtain an organic layer. The organic layer was washed with water and saturated saline and was then dried over anhydrous sodium sulfate and was then concentrated to produce a crude product. The crude product was purified by silica gel column chromatography (hexane:ethyl acetate:triethylamine=20:1:1 to 20:2:1, ethyl acetate:hexane=4:1 to 6:1) to produce compound DH-3 (255 mg, 66%) as a white foam-like solid substance.

$^{31}$P NMR (CDCl$_3$) δ 148.7, 148.9.

HRMS (MALDI): calcd for $C_{49}H_{67}N_6NaO_9P$ [M+Na$^+$] 937.4599, found 937.4611.

Synthesis Example 10

A compound (1) wherein "Base" was a thymin-1-yl group, A$^1$ was a methylene group, A$^2$ was a single bond, X was a n-propylene group, R$^1$ was DMTr, R$^2$ was —P(N(i-Pr)$_2$)(OC$_2$H$_4$CN), and R$^3$ was a 4-methylpiperazin-1-yl group (hereinafter, also referred to as "compound Pip-T-3") was synthesized according to the reaction scheme shown below.

[Formula 60]

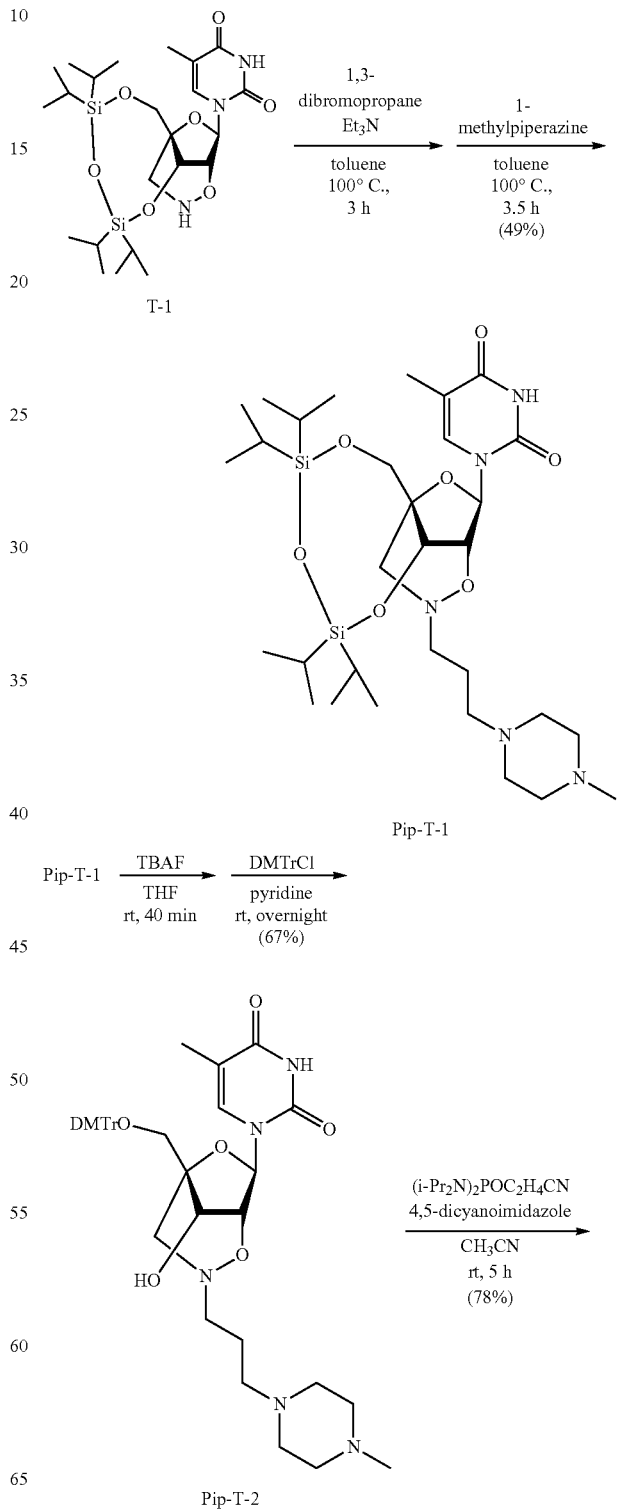

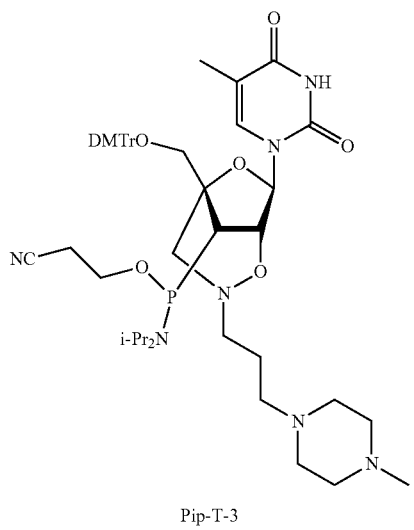

Pip-T-3

(Synthesis of Compound Pip-T-1)

1,3-Dibromopropane (3.45 mL, 33.8 mmol) and triethylamine (7.4 mL, 53.2 mmol) were added to a solution of compound T-1 (4.0 g, 7.58 mmol) in toluene (100 mL) at room temperature, then the resultant solution was warmed to 100° C. and was then stirred for 3 hours. The reaction solution was cooled to room temperature, then 1-methylpiperazine (3.8 mL, 34.1 mmol) was added to the solution, the resultant solution was warmed to 100° C. again and was then stirred for 3 hours and 30 minutes. Subsequently, the reaction solution was cooled to room temperature, was then filtrated through celite, then a residue produced by subjecting a filtrate to distillation under reduced pressure was purified by silica gel column chromatography (ethyl acetate:methanol:triethylamine:dichloromethane=22:2:1:75) to produce compound Pip-T-1 (2.46 g, 49%) as a white solid substance. $^1$H NMR (DMSO-$d_6$) δ 0.90-1.04 (28H, m), 1.67-1.80 (5H, m), 2.20-2.58 (13H, m), 2.67-2.80 (4H, m), 3.64 (1H, d, J=14 Hz), 3.92 (1H, d, J=3 Hz), 4.04 (1H, d, J=14 Hz), 4.37 (1H, d, J=3 Hz), 6.11 (1H, s), 7.49 (1H, d, J=1 Hz), 11.41 (1H, s).

(Synthesis of Compound Pip-T-2)

Under a nitrogen stream, tetra-n-butylammonium fluoride (a 1-M tetrahydrofuran solution, 2.80 mL, 2.80 mmol) was added to a solution of compound Pip-T-1 (0.894 g, 1.34 mmol) in tetrahydrofuran (24 mL) under ice cooling, and the resultant solution was stirred at room temperature for 40 minutes. A residue obtained by the distillation of the solvent away under reduced pressure was subjected to alumina column chromatography (chloroform:methanol=10:1) using a short column to remove a reaction residue, thereby producing an intermediate. Subsequently, the intermediate was azeotropically distilled with a pyridine:toluene (=1:1) mixed solution, then the intermediate was dissolved in pyridine (22 mL), then 4,4'-dimethoxytrityl chloride (1.179 g, 3.48 mmol) was added to the solution under ice cooling, and the resultant solution was stirred overnight at room temperature while removing an ice bath. Next morning, 4,4'-dimethoxytrityl chloride (0.181 g, 0.534 mmol) was further added under ice cooling, and the resultant solution was stirred at room temperature for 2 hours and 30 minutes. Subsequently, an aqueous sodium bicarbonate solution was added under ice cooling, the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:methanol:triethylamine=20:0:1 to 20:1:1) to produce compound Pip-T-2 (0.656 g, 67%) as a white solid substance.

$^1$H NMR (DMSO-$d_6$) δ 1.31 (3H, s), 1.60-1.71 (2H, m), 2.07-2.56 (13H, m), 2.61-2.83 (4H, m), 3.16-3.23 (2H, m), 4.05-4.07 (1H, m), 4.21-4.22 (1H, m), 5.54 (1H, d, J=6 Hz), 6.11 (1H, s), 6.90-6.92 (4H, m), 7.23-7.44 (9H, m), 7.62 (1H, s), 11.36 (1H, s).

(Synthesis of Compound Pip-T-3)

Under a nitrogen stream, 4,5-dicyanoimidazole (0.121 g, 1.02 mmol) and 2-cyanoethyl N,N,N',N'-tetraisopropylphosphordiamidite (0.390 mL, 1.23 mmol) were added to a solution of compound Pip-T-2 (0.496 g, 0.68 mmol) in acetonitrile (25 mL) under ice cooling, and the resultant solution was stirred at room temperature for 5 hours. An aqueous sodium bicarbonate solution was added under ice cooling, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:methanol:triethylamine=20:0:1 to 20:1:1) to produce compound Pip-T-3 (0.490 g, 78%) as a white foam-like solid substance. $^{31}$P NMR (DMSO-$d_6$) δ 148.62, 147.22.

HRMS (MALDI): calcd for $C_{49}H_{66}N_7NaO_9P$ [M+Na$^+$] 950.4552, found 950.4546.

Synthesis Example 11

A compound (1) wherein "Base" was a thymin-1-yl group, $A^1$ was a methylene group, $A^2$ was a single bond, X was a n-propylene group, $R^1$ was DMTr, $R^2$ was —P(N(i-Pr)$_2$)(OC$_2$H$_4$CN), and $R^3$ was NHC(=NCOC$_2$H$_4$CN) (NHCOC$_2$H$_4$CN) (hereinafter, also referred to as "compound Gua-T-3") was synthesized according to the reaction scheme shown below.

[Formula 61]
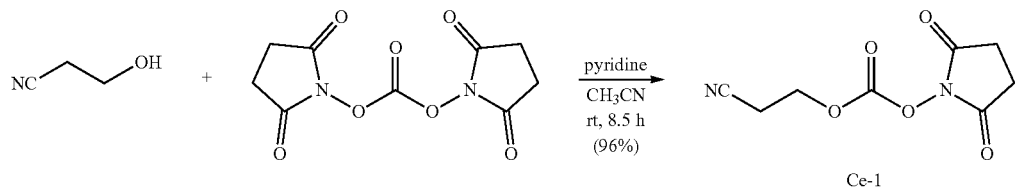
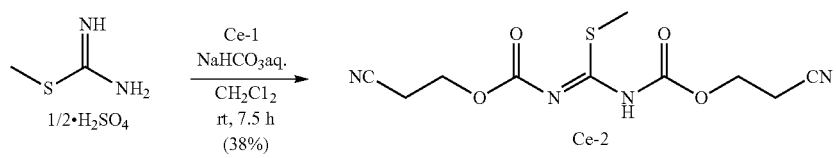
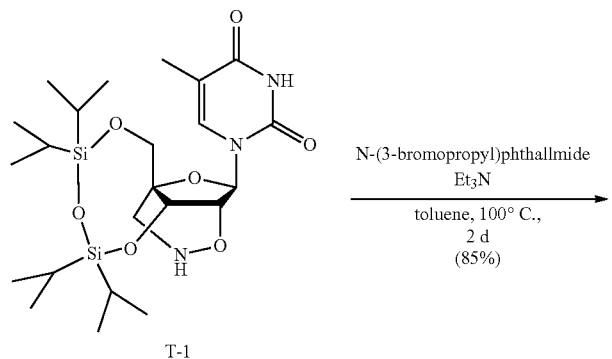
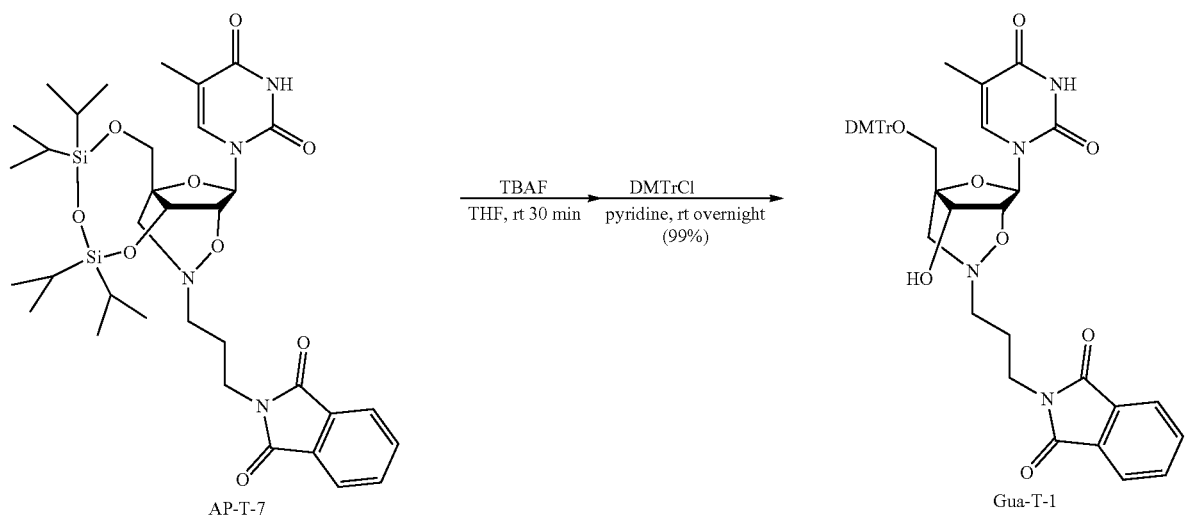

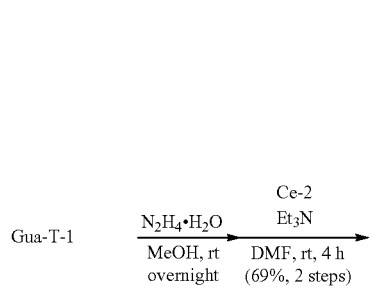
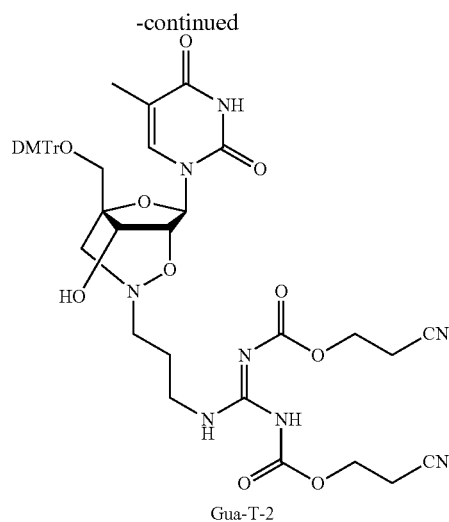
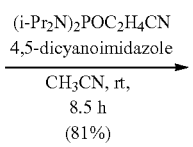
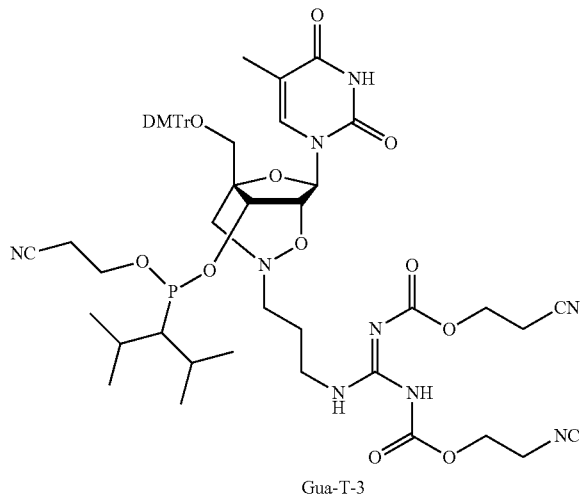

(Synthesis of Compound Ce-1)

N,N'-Disuccinimidyl carbonate (8.0 g, 31.2 mmol) and pyridine (2.7 mL, 33.5 mmol) were added to a solution of 2-cyanoethanol (1.85 ml, 27.3 mmol) in acetonitrile (160 mL) under ice cooling, and the resultant solution was stirred at room temperature for 8 hours and 30 minutes. The reaction solution was subjected to distillation under reduced pressure, then dichloromethane and an aqueous sodium bicarbonate solution were added to a residue, and the resultant solution was extracted with dichloromethane. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (dichloromethane:acetonitrile=1:0 to 4:1) to produce compound Ce-1 (5.58 g, 96%) as a white solid substance.

$^1$H NMR (CDCl$_3$) δ 2.86 (2H, t, J=6 Hz), 2.87 (4H, s), 4.53 (2H, t, J=7 Hz).

(Synthesis of Compound Ce-2)

S-Methylisothiourea sulfate (0.78 g, 5.6 mmol) and a 1.0-M aqueous sodium hydrogen carbonate solution (22.4 ml, 22.4 mmol) were added to a solution of compound Ce-1 (2.5 g, 11.8 mmol) in dichloromethane (50 mL), and the resultant solution was stirred vigorously at room temperature for 7 hours and 30 minutes. Subsequently, an aqueous sodium bicarbonate solution was added, and the resultant solution was extracted with dichloromethane, an organic layer obtained was dried over anhydrous sodium sulfate. Anhydrous sodium sulfate was removed by filtration, and then a filtrate was subjected to distillation under reduced pressure to produce a crude product, and the crude product was purified by silica gel column chromatography (dichloromethane:ethyl acetate=1:0 to 10:1) to produce compound Ce-2 (0.60 g, 38%) as a pale yellow oily substance.

$^1$H NMR (CDCl$_3$) δ 2.46 (3H, s), 2.80 (4H, t, J=6 Hz), 4.37-4.42 (4H, m), 11.81 (1H, brs).

(Synthesis of Compound Gua-T-1)

Under a nitrogen stream, tetra-n-butylammonium fluoride (a 1-M tetrahydrofuran solution, 4.1 mL, 4.1 mmol) was added to a solution of compound AP-T-7 (1.40 g, 1.96 mmol) in tetrahydrofuran (30 mL) under ice cooling, and the resultant solution was stirred at room temperature for 30 minutes. A residue obtained by the distillation of the solvent away under reduced pressure was subjected to silica gel column chromatography (ethyl acetate:methanol=20:1 to 6:1) using a short column to remove a reaction residue, thereby producing an intermediate. The intermediate was azeotropically distilled with pyridine and then with a pyridine:toluene (=1:1) mixed solution, then the intermediate was dissolved in pyridine (30 mL), then 4,4'-dimethoxytrityl chloride (1.00 g, 2.95 mmol) was added under ice cooling, and the resultant solution was stirred overnight at room temperature while removing an ice bath. Next morning, an aqueous sodium bicarbonate solution was added to the solution under ice cooling, then the resultant solution was diluted with water, and the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (ethyl acetate:hexane=1:1 to 1:0) to produce compound Gua-T-1 (1.51 g, 99%) as a white foam-like solid substance. $^1$H NMR (CDCl$_3$) δ 1.45 (3H, d, J=1 Hz), 1.95-2.12 (2H, m), 2.57 ($^1$H, d, J=9 Hz), 2.70-2.83 (3H, m), 2.90-3.00 (1H, m), 3.31 (1H, d, J=10 Hz), 3.37 (1H, d, J=10 Hz), 3.76-3.87 (8H, m), 4.23 (1H, dd, J=3 Hz, J=9 Hz), 4.36 (1H, d, J=3 Hz), 6.30 (1H, s), 6.82-6.87 (4H, m), 7.22-7.45 (9H, m), 7.66-7.71 (2H, m), 7.73 (1H, d, J=1 Hz), 7.80-7.85 (2H, m), 8.23 (1H, s).

(Synthesis of Compound Gua-T-2)

Hydrazine monohydrate (0.19 mL, 3.91 mmol) was added to a solution of compound Gua-T-1 (1.01 g, 1.30 mmol) in methanol, and the resultant solution was stirred at room temperature for 8 hours and 40 minutes. Subsequently, hydrazine monohydrate (0.075 mL, 1.54 mmol) was further added, and the resultant solution was stirred at room temperature overnight. A residue obtained by the distillation of the solvent away under reduced pressure was subjected to amino silica gel column chromatography (dichloromethane:methanol=5:1 to 4:1) using a short column to remove a reaction residue, thereby producing an intermediate. Subsequently, the intermediate was dissolved in dimethylformamide (7.5 ml), then compound Ce-2 (0.38 g, 1.34 mmol) and triethylamine (0.182 ml, 1.31 mmol) were added, and the resultant solution was stirred at room temperature for 4 hours. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was purified by silica gel column chromatography (dichloromethane:ethyl acetate:hexane=1:2:2 to 0:1:0) to produce compound Gua-T-2 (0.79 g, 69%) as a white foam-like solid substance.

$^1$H NMR (CDCl$_3$) δ 1.45 (3H, s), 1.88-2.05 (2H, m), 2.61 (1H, d, J=9 Hz), 2.72-2.87 (7H, m), 2.91-2.98 (1H, m), 3.33 (1H, d, J=10 Hz), 3.38 (1H, d, J=11 Hz), 3.54-3.61 (2H, m), 3.80 (6H, s), 4.24-4.31 (3H, m), 4.35-4.42 (3H, m), 6.32 (1H, s), 6.86-6.84 (4H, m), 7.23-7.45 (9H, m), 7.75 (1H, s), 8.36 (1H, t, J=6 Hz), 8.39 (1H, s), 11.73 (1H, s).

(Synthesis of Compound Gua-T-3)

Under a nitrogen stream, 4,5-dicyanoimidazole (81.2 mg, 0.69 mmol) and 2-cyanoethyl N,N,N',N'-tetraisopropylphosphordiamidite (0.275 mL, 0.87 mmol) were added to a solution of compound Gua-T-2 (0.50 g, 0.57 mmol) in acetonitrile (25 mL) under ice cooling, and the resultant solution was stirred at room temperature for 5 hours and 30 minutes. The solution was placed under ice-cooling condition again, then 4,5-dicyanoimidazole (67.6 mg, 0.57 mmol) and 2-cyanoethyl N,N,N',N'-tetraisopropylphosphordiamidite (0.220 mL, 0.69 mmol) were further added, and the resultant solution was stirred at room temperature for additional 3 hours. Subsequently, the solution was ice-cooled, then an aqueous sodium bicarbonate solution was added to the solution, the resultant solution was diluted with water, and then the diluted solution was extracted with ethyl acetate. An organic layer thus obtained was washed with saturated saline, and was then dried over anhydrous sodium sulfate. Anhydrous sodium sulfate was removed by filtration, and then a filtrate was subjected to distillation under reduced pressure to produce a crude product, and the crude product was then purified by silica gel column chromatography (chloroform:methanol=50:1) silica gel column chromatography (ethyl acetate:hexane=4:1 to 10:1) to produce compound Gua-T-3 (0.50 g, 81%) as a white foam-like solid substance. $^{31}$P NMR (CDCl$_3$) δ 149.27, 148.76.

HRMS (FAB): calcd for C$_{53}$H$_{66}$N$_{10}$O$_{13}$P[M+H$^+$] 1081.4548, found 1081.4551.

<<Oligonucleotide Synthesis Examples>>

Oligonucleotides were synthesized in accordance with a standard phosphoramidite protocol using the compounds (AP-T-6, DT-3, DH-3, Pip-T-3, Gua-T-3) produced in the Synthesis Examples by using a nucleic acid automatic synthesizer (Expedite (registered tradename), manufactured by 8909/ABI). Each of the five types of oligonucleotides thus produced had a unit represented by formula (4), wherein X and R$^3$ were as follows.

X=(CH$_2$)$_3$, R$^3$=NH$_2$ (hereinafter, also referred to as "(CH$_2$)$_3$NH$_2$")

X=(CH$_2$)$_3$, R$^3$=NMe$_2$ (hereinafter, also referred to as "(CH$_2$)$_3$NMe$_2$")

X=(CH$_2$)$_6$, R$^3$=NMe$_2$ (hereinafter, also referred to as "(CH$_2$)$_6$NMe$_2$")

X=(CH$_2$)$_3$, R$^3$=4-methylpiperazin-1-yl group (hereinafter, also referred to as "(CH$_2$)$_3$Pip-Me")

X=(CH$_2$)$_3$, R$^3$=NHC(=NH)NH$_2$ (hereinafter, also referred to as "(CH$_2$)$_3$Gua")

Each of the oligonucleotides of which the 5'-terminal was protected by a dimethoxytrityl group and which was supported on a solid phase was subjected to the cleavage from a column with a 28% aqueous ammonia solution (for 1.5 hours), and then the cleaved oligonucleotide was reacted in a 28% aqueous ammonia solution for 16 hours at 60° C. to deprotect all of the protecting groups. With respect to (CH$_2$)$_3$Gua, the cleavage from a column was carried out using a 50% aqueous piperidine solution for 24 hours at room temperature.

The oligonucleotide was subjected to a simple purification using an NAP-10 column, and was then purified by reversed-phase HPLC [WakoPak (registered tradename) WS-DNA column, 10.0 mm×250 mm) [conditions: a gradient of 8 to 16% of acetonitrile in a 0.1-M triethylammonium acetate buffer (pH 7.0) at 3 ml/min. for 30 minutes, column temperature of 50° C.].

The purities of the synthesized oligonucleotides were confirmed by reversed-phase HPLC [WakoPak (registered tradename) WS-DNA column, 4.6 mm×250 mm) [conditions: a gradient of 8 to 16% of acetonitrile in a 0.1-M triethylammonium acetate buffer (pH7.0) at 1 ml/min. for 30 minutes, column temperature of 50° C., detection wavelength of 254 nm]. Each of the synthesized oligonucleotides had purity of 90% or more.

The molecular weights of the synthesized oligonucleotides were determined by a MALDI-TOF-MASS measurement. The calculated values and the found values (measurement results) of the molecular weights are shown in the table below. The unit represented by formula (4) was incorporated in a site corresponding to X in each of the antisense strands (SEQ ID NOs: 1 to 4) shown in the table, in which "Base" was thymine. Each of the nucleotide sequences excluding X was composed of DNA (formula (5) wherein $R^a$=H). As references, the calculated values and the found values of the molecular weights of an oligonucleotide in which 2',4'-BNA$^{NC}$(N-Me) (formula (7) wherein $R^b$=Me) was integrated at a site corresponding to X (hereinafter, referred to as "Me" in the table) and an oligonucleotide in which 2',4'-BNA$^{NC}$(N—H) (formula (7) wherein $R^b$=H) was integrated at a site corresponding to X (hereinafter, referred to as "H" in the table) are also shown in the table.

(AGCAAAAAACGC)-3'; SEQ ID NO: 7) (a sense strand). As references, oligonucleotides each of which was synthesized by incorporating each of LNA (formula (6)), 2',4'-BNA$^{NC}$(N-Me) (formula (7) wherein R=Me) and 2',4'-BNA$^{NC}$(N—H) (formula (7) wherein R=H) into a part of the sequence represented by SEQ ID NO: 5 were provided as antisense strands.

A sample solution (120 μl) in which the final concentrations of sodium chloride, a sodium phosphate buffer solution (pH7.2), each of the antisense strands and each of the sense strands were adjusted to 100 mM, 10 mM, 4 μM and 4 μM,

TABLE 1

| MALDI-TOF-MASS | Calculated values [M − H]$^-$/Found values [M − H]$^-$ | | | |
|---|---|---|---|---|
| Antisense strand | Me | H | $(CH_2)_3NH_2$ | $(CH_2)_3NMe_2$ |
| 5'-d(GCGTT<u>X</u>TTTGCT)-3' | 3689.47/3687.54 | — | 3732.53/3733.64 | 3760.59/3761.97 |
| 5'-d(GCG<u>X</u>T<u>X</u>T<u>X</u>TGCT)-3' | 3803.57/3804.88 | 3761.48/3760.11 | 3932.75/3932.84 | 4016.93/4017.32 |
| 5'-d(GCG<u>XXXXXX</u>GCT)-3' | 3974.72/3973.40 | 3890.54/3889.73 | 4233.08/4232.82 | 4401.44/4401.50 |
| 5'-d(TTTTTTTT<u>X</u>T)-3' | 3036.08/3036.65 | 3022.05/3023.60 | 3079.14/3079.17 | 3107.20/3109.16 |

| MALDI-TOF-MASS | Calculated values [M − H]$^-$/Found values [M − H]$^-$ | | |
|---|---|---|---|
| Antisense strand | $(CH_2)_6NMe_2$ | $(CH_2)_3Pip$-Me | $(CH_2)_3Gua$ |
| 5'-d(GCGTT<u>X</u>TTTGCT)-3' | 3802.67/3802.05 | 3815.67/3815.54 | 3774.58/3774.69 |
| 5'-d(GCG<u>X</u>T<u>X</u>T<u>X</u>TGCT)-3' | 4143.17/4144.01 | 4182.17/4180.25 | 4058.90/4056.97 |
| 5'-d(GCG<u>XXXXXX</u>GCT)-3' | 4653.92/4654.40 | 4731.92/4730.22 | 4485.38/4484.50 |
| 5'-d(TTTTTTTT<u>X</u>T)-3' | 3149.28/3150.33 | 3162.28/3160.82 | 3121.19/3121.19 |

TEST EXAMPLES

[Test Example 1] Measurement of Melting Temperatures (Tm) of Oligonucleotides (Evaluation of Double Strand Forming Capability)

The double strand forming capability of antisense strands was examined by measuring a melting temperature (Tm) between each of five oligonucleotides (4) (i.e., $(CH_2)_3NH_2$, $(CH_2)_3NMe_2$, $(CH_2)_6NMe_2$, $(CH_2)_3Pip$-Me, $(CH_2)_3Gua$) (antisense strands) according to the present invention each of which was synthesized by incorporating each of the compounds (AP-T-6, DT-3, DH-3, Pip-T-3, Gua-T3) produced in the above-mentioned Synthesis Examples into a part of the sequence represented by SEQ ID NO: 5 and single-stranded DNA (5'-d(AGCAAAAAACGC)-3'; SEQ ID NO: 6) or single-stranded RNA (5'-r respectively, was prepared, then the sample solution was warmed from 15° C. to 110° C. at a rate of 0.5° C./min., and an absorbance at 260 nm was measured at 0.5-° C. intervals using a spectrophotometer (UV-1800, manufactured by Shimadzu Corporation).

A Tm value was calculated from a measurement value by a differentiation method, and an average value of at least two independent measurement results was determined as a Tm value. The results are shown in the table below. The results are shown in the table below.

Capability of forming double strand with single-stranded DNA (Tm value)

[TABLE 2]

| | Tm (° C.) | | | | | | | |
|---|---|---|---|---|---|---|---|---|
| Antisense strand | LNA-T | Me | H | $(CH_2)_3NH_2$ | $(CH_2)_3NMe_2$ | $(CH_2)_6NMe_2$ | $(CH_2)_3Pip$-Me | $(CH_2)_3Gua$ |
| 5'-d(GCGTTTTTTGCT)-3' | 52 | 52 | 52 | 52 | 52 | 52 | 52 | 52 |
| 5'-d(GCGTT<u>X</u>TTGCT)-3' | — | 50 | — | 55 | 55 | 52 | 52 | 57 |
| 5'-d(GCG<u>XTXTX</u>TGCT)-3' | 57 | 52 | 56 | 62 | 62 | 55 | 56 | 62 |
| 5'-d(GCG<u>XXXXXX</u>GCT)-3' | — | 63 | 73 | 75 | 77 | 69 | 68 | 83 |

Sense strand = 5'-d(AGCAAAAAACGC)-3'
Conditions: 100 nM NaCl, 10 mM sodium phosphate buffer (pH 7.2), containing 4 μM of each strand; scanning rate: 0.5° C./min. (15° C. to 110° C.)

Capability of forming double strand with single-stranded RNA (Tm value)

[TABLE 3]

| Antisense strand | Tm (° C.) | | | | | | | |
|---|---|---|---|---|---|---|---|---|
| | LNA-T | Me | H | $(CH_2)_3NH_2$ | $(CH_2)_3NMe_2$ | $(CH_2)_6NMe_2$ | $(CH_2)_3$Pip-Me | $(CH_2)_3$Gua |
| 5'-d(GCGTTTTTTGCT)-3' | 48 | 48 | 48 | 48 | 48 | 48 | 48 | 52 |
| 5'-d(GCGGTTXTTTGCTGCT)-3' | — | 51 | — | 51 | 52 | 50 | 51 | 52 |
| 5'-d(GCGXTXTXTGCT)-3' | 65 | 64 | 65 | 64 | 65 | 61 | 63 | 63 |
| 5'-d(GCGXXXXXXGCT)-3' | — | 80 | 83 | 79 | 82 | 79 | 81 | 83 |

Sense strand = 5'-r(AGCAAAAAACGC)-3'

Conditions: 100 nM NaCl, 10 mM sodium phosphate buffer (pH 7.2), containing 4 µM of each strand; scanning rate: 0.5° C./min. (15° C. to 110° C.)

In each of the oligonucleotides (4) according to the present invention, it was demonstrated that the Tm value with respect to the single-stranded DNA or the single-stranded RNA increased with the increase in the number of the unit represented by formula (4) or (4a) and therefore excellent double strand formation capability was exerted. Accordingly, the oligonucleotides (4) according to the present invention are suitable for use in DNA- and RNA-targeting nucleic acid therapeutics and genetic diagnosis for which excellent double strand formation capability is required.

[Test Example 2] Measurement of Enzyme Resistance Capability of Oligonucleotides 1) Preparation of Oligonucleotides for Use in Measurement of Enzyme Resistance Capability Oligonucleotides shown in the table below, each having a sequence in which the sequence represented by SEQ ID NO: 8 or a part thereof was modified, were prepared in the same manner as in the above-mentioned Synthesis Examples of the oligonucleotides.

[TABLE 4]

| No. | Name of oligonucleotide | Sequence (5'→3') | Length (mer) |
|---|---|---|---|
| 1 | DNA oligo | TTTTTTTTTT | 10 |
| 2 | $NH_2$ oligo | TTTTTTTTt$^\alpha$T | 10 |
| 3 | $NMe_2$ oligo | TTTTTTTTt$^\beta$T | 10 |
| 4 | S oligo | TTTTTTTT^T | 10 |
| 5 | NH oligo | TTTTTTTTt$^\alpha$T | 10 |
| 6 | LNA oligo | TTTTTTTTtT | 10 |

T = DNA-T
$t^\alpha$ = 2',4'-BNA$^{NC}$(N—$(CH_2)_3NH_2$)-T
$t^\beta$ = 2',4'-BNA$^{NC}$(N—$(CH_2)_3NMe_2$)-T
$t^\alpha$ = 2',4'-BNA$^{NC}$(N—H)-T
t = LNA-T
^ = Phosphorothioate bond 2) Preparation of Sample Solutions Sample solutions each having the composition shown in the table below were prepared.

TABLE 5

| Reagent | Final concentration |
|---|---|
| Tris HCl pH 8.0 | 50 mM |
| $MgCl_2$ | 10 mM |
| Oligonucleotide | 7.5 µM |

3) Enzymatic Reaction

The operations mentioned below were carried out at a temperature of 37° C. using a device (MD-MINI, manufactured by Major Science).
 (1) The sample solution was incubated (for 5 minutes).
 (2) An enzyme CAVP (Crotalus adamanteus Venom phosphodiesterase I) was added at a 0.625 µg/mL to initiate a reaction.
 (3) EDTA was added in such a manner that the concentration of EDTA became 5.0 mM in a reaction solution at the time point of the completion of the reaction to terminate the reaction.
 (4) The reaction times were 0 minute, 5 minutes, 10 minutes, 40 minutes and 80 minutes.

4) Evaluation of Enzyme Resistance Capability

Each of the sample solutions in each of which the enzymatic reaction had been completed was subjected to a HPLC analysis under the following conditions.
(Conditions)
 Device: LC-2010A HT (manufactured by Shimadzu Corporation)
 Column: XBridge Oligonucleoties BEH C18 column 130 Å, 2.5 µm, 4.6 mm×50 mm mobile phase
 Solution A: a 0.1-M triethylammonium acetate buffer (pH 7.0)
 Solution B: a 0.1-M triethylammonium acetate buffer (pH 7.0): acetonitrile=1:1 (v/v) gradient: 5 to 30% ((v/v) solution B), 15 minutes)
 flow rate: 0.8 mL/min.
 Column temperature: 50° C.
 Detection wavelength: 268 nm
 Injection amount: 15 µL (101.2 pmol)

The amount of each of the oligonucleotides which was undigested with the enzyme was measured from a HPLC analysis result, and a residual ratio of the undigested oligonucleotide at each of the reaction times was calculated in accordance with the following formula.

[Mathematical formula 1]
$$\text{Residual ratio (\%) of undigested oligonucleotides at each reaction time} = \frac{\text{Area of undigested oligonucleotide at each reaction time}}{\text{Area of undigested oligonucleotide at 0 minute reaction time}} \times 100$$

5) Results

The results are shown in the table below and FIG. 2.

TABLE 6

| No. | Name of oligonucleotide | Residual ratio (%) of undigested oligonucleotide at each reaction time | | | | |
|---|---|---|---|---|---|---|
| | | 0 min. | 5 min. | 10 min. | 40 min. | 80 min. |
| 1 | DNA oligo | 100.0 | 0.0 | 0.0 | 0.0 | 0.0 |
| 2 | NH$_2$ oligo | 100.0 | 97.1 | 96.8 | 91.6 | 87.4 |
| 3 | NMe$_2$ oligo | 100.0 | 98.5 | 98.8 | 87.3 | 83.0 |
| 4 | S oligo | 100.0 | 98.2 | 96.6 | 88.6 | 84.6 |
| 5 | NH oligo | 100.0 | 96.5 | 95.4 | 73.0 | 57.0 |
| 6 | LNA oligo | 100.0 | 74.2 | 48.8 | 1.3 | 1.1 |

As apparent from the above-shown results, the oligonucleotides (4) according to the present invention had superior enzyme resistance compared with the naturally occurring oligonucleotide and other non-naturally-occurring oligonucleotides.

[Test Example 3] Clamping Capability of Oligonucleotides

1) Preparation of Oligonucleotides for which Clamping Capability was to be Measured Oligonucleotides shown in the table below were prepared in the same manner as in the above-mentioned oligonucleotide synthesis examples. Each of clamp nucleic acid 1 (SEQ ID NO: 12) and clamp nucleic acid 3 corresponds to the conventional 2',4'-BNA$^{NC}$(N-Me) (formula (7) wherein R=Me), and each of clamp nucleic acid 2 (SEQ ID NO: 12) and clamp nucleic acid 4 corresponds to the oligonucleotides (4) according to the present invention.

[TABLE 7]

| No. | Name of oligonucleotide | Sequence (5'→3') | Length (mer) |
|---|---|---|---|
| 1 | Forward primer | ACTGAATATAAACTTGTGGTAG | 22 |
| 2 | Reverse primer | ATTGTTGGATCATATTCGTC | 20 |
| 3 | Amplification confirmation probe | j-CTTGACGATACAGCTAATTCAGAATCAT-R | 28 |
| 4 | Clamp nucleic acid 1 | gCCt$^\beta$Ac$^\beta$Gc$^\beta$c$^\beta$Ac$^\beta$c$^\beta$AGc$^\beta$TCC-P | 18 |
| 5 | Clamp nucleic acid 2 | gCCt$^\alpha$Ac$^\alpha$Gc$^\alpha$c$^\alpha$Ac$^\alpha$c$^\alpha$AGc$^\alpha$TCC-P | 18 |

[TABLE 7]-continued

| No. | Name of oligonucleotide | Sequence (5'→3') | Length (mer) |
|---|---|---|---|
| 6 | Clamp nucleic acid | 3c$^\beta$c$^\beta$a$^\beta$c$^\beta$c$^\beta$a$^\beta$g$^\beta$c$^\beta$-P | 8 |
| 7 | Clamp nucleic acid | 4c$^\alpha$c$^\alpha$a$^\alpha$c$^\alpha$c$^\alpha$a$^\alpha$g$^\alpha$c$^\alpha$-P | 8 |

A, C, G, T = DNA-A, -C, -G, -T a$^\beta$, c$^\beta$, g$^\beta$, t$^\beta$ = 2',4'-BNA$^{NC}$[N-Me]-A, $^m$C, G, T a$^\alpha$, c$^\alpha$, g$^\alpha$, t$^\alpha$ = 2',4'-BNA$^{NC}$(N (CH$_2$)$_3$NH$_2$)-A, -$^m$C, -G, -T G = 2'-OMe-RNA-G;

j = JOE;

R = TAMRA;

P = Monophosphorylated

2) Preparation of Test Specimen

As a wild-type gene specimen of KRAS gene, a commercially available Human genomic DNA (Promega Corporation) was used as a template. As a G12V mutant gene specimen, DNA extracted from SW480 cultured cells (DS Pharma) was used as a template.

The amount of each DNA was determined from an UV spectrum of each specimen and a Ct value obtained by a real-time PCR using a forward primer (SEQ ID NO: 9), a reverse primer (SEQ ID NO: 10) and an amplification confirmation probe (SEQ ID NO: 11).

Based on the DNA amount, model test specimens respectively having mutant contents of 10%, 1.0%, 0.1%, 0.01% and 0% were prepared. Each of the model test specimens was used in an amount of 50 ng in each experiment.

3) Nucleic Acid Amplification Device and Nucleic Acid Amplification Reagent

StepOnePlus (ABI) was used as a real-time PCR device, and TaqMan™ Fast Advanced Master Mix (ABI) was used as a nucleic acid amplification reagent. The amount of each of the reagents to be used was as directed in the appended instructions.

4) Primer, Amplification Confirmation Probe, Clamp Nucleic Acid

Each of the forward and reverse primers was used in an amount of 10 pmol in each experiment, and the amplification confirmation probe was used in an amount of 2.5 pmol in each experiment. As clamp nucleic acids, clamp nucleic acids 1 to 4 each having the sequence for wild-type KRAS gene were used each in an amount of 10 pmol or 1.0 pmol in each experiment.

5) Nucleic Acid Amplification Operation and Results

A mixture of a test specimen, a nucleic acid amplification reagent, a primer, an amplification confirmation probe and a clamp nucleic acid was applied to a nucleic acid amplification device under the conditions of (i) 2 minutes at 50° C., (ii) 20 seconds at 95° C., (iii) 10 seconds at 95° C., and (iv) 60 seconds at 57° C., then (v) the operations (iii) to (iv) were repeated 55 cycles. The nucleic acid amplification process (until 55 cycles) using each test specimen, each clamp nucleic acid and each amplification confirmation probe was monitored.

6) Results

Nucleic acid amplification curves when a clamp nucleic acid was used in an amount of 10 pmol is shown in FIGS. 3A-3E. Ct value data are shown in the table below. In the table, "M" means "mutant", and "W" means "wild-type".

The term "Ct value" refers to the number of cycles at which the amount of a PCR amplification product reaches a certain amount, and the term "ΔCt value" refers to the difference between a Ct value of a specimen having a mutant content of 0% and a Ct value of each of the test specimens.

The Ct value data in real-time PCR using clamp nucleic acids 1 to 4 (the amount of clamp nucleic acid used: 10 pmol)

TABLE 8

| Clamp nucleic acid | | X = M/(M + W) | | | | |
|---|---|---|---|---|---|---|
| | | 10% | 1% | 0.10% | 0.01% | 0% |
| Without clamp | Ct value | 24.88 | 24.9 | 24.83 | 24.88 | 24.89 |
| | ΔCt$_{0\%-x\%}$ value | 0.02 | 0 | 0.07 | 0.02 | |
| Clamp nucleic acid 1 | Ct value | 29.59 | 33.33 | 36.51 | 37.96 | 37.96 |
| | ΔCt$_{0\%-x\%}$ value | 8.37 | 4.63 | 1.46 | 0.01 | |
| Clamp nucleic acid 2 | Ct value | 31.54 | 35.4 | 37.69 | 39 | 38.96 |
| | ΔCt$_{0\%-x\%}$ value | 7.41 | 3.56 | 1.27 | −0.05 | |
| Clamp nucleic acid 3 | Ct value | 26.96 | 27.67 | 27.72 | 27.59 | 27.69 |
| | ΔCt$_{0\%-x\%}$ value | 0.74 | 0.02 | −0.03 | 0.11 | |
| Clamp nucleic acid 4 | Ct value | 28.3 | 31.44 | 33.66 | 34.37 | 34.6 |
| | ΔCt$_{0\%-x\%}$ value | 6.31 | 3.16 | 0.94 | 0.23 | |

When no clamp nucleic acid was used, in PCRs respectively using the templates, any difference was not observed in the amplification. In contrast, when clamp nucleic acids 1 and 2 each having a length of 8-mer were used, such a difference was observed in the amplification that the Ct value increased with the increase in the content of the wild-type gene in the template. These results demonstrate that oligonucleotides of both of clamp nucleic acids 1 and 2 had clamping capability.

When clamp nucleic acids 3 and 4 each having a length of 8-mer were used, substantially no clamping capability was observed with respect to clamp nucleic acid 3 (the prior art technique), while clamp nucleic acid 4 (the present invention) clamping capability exhibited clamping capability even though clamp nucleic acid 4 had a length as short as 8-mer. From these results, it was demonstrated that the oligonucleotide (4) according to the present invention could be used as a short clamp nucleic acid, and could also be used as a clamp nucleic acid even when a short gene region in which mutations are concentrated in cancer and viruses is targeted.

Nucleic acid amplification curves obtained when a clamp nucleic acid was used in an amount of 1.0 pmol is shown in FIGS. 3G and 3H. Ct value data are shown in the table below.

Ct value data in real-time PCR using clamp nucleic acids 1 and 2 (the amount of clamp nucleic acid used: 1.0 pmol)

TABLE 9

| Clamp nucleic acid | | X = M/(M + W) | | | | |
|---|---|---|---|---|---|---|
| | | 10% | 1% | 0.10% | 0.01% | 0% |
| Clamp nucleic acid 1 | Ct value | 28.13 | 29.81 | 30.06 | 30.12 | 30.07 |
| | $\Delta Ct_{0\%-x\%}$ value | 1.94 | 0.25 | 0 | −0.05 | |
| Clamp nucleic acid 2 | Ct value | 30.64 | 34.59 | 37.31 | 38.97 | 38.96 |
| | $\Delta Ct_{0\%-x\%}$ value | 8.32 | 4.37 | 1.65 | −0.01 | |

When the amount of a clamp nucleic acid used was reduced to 1/10, i.e., from 10 pmol to 1.0 pmol, in the clamp nucleic acid 1 (the prior art technique), the clamping effect was decreased greatly. In contrast, in the clamp nucleic acid 2 (the present invention), any change was observed in the clamping effect. Accordingly, it was demonstrated that the oligonucleotide (4) according to the present invention can realize a high-sensitivity clamp PCR even when the amount of the oligonucleotide (4) used was further reduced.

[Test Example 4] Measurement of Strand Invasion of Oligonucleotide

1) Preparation of Oligonucleotides for Strand Invasion

Oligonucleotides shown in the table below were prepared in the same manner as in the above-mentioned oligonucleotide synthesis examples.

[TABLE 10]

| No. | Name of oligo-nucleotide | Sequence (5'→3') | Length (mer) |
|---|---|---|---|
| 1 | PNA20 | H-(Lys)ggcatgttcatcatcagtaa(Lys)-NH$_2$ | 20 |
| 2 | LSI-1 | 5'-ggcatGttcatcAtcagtaA-3' | 20 |
| 3 | BSI-4 | 5'-c$^\alpha$a$^\beta$t$^\alpha$Gt$^\alpha$t$^\alpha$Ca$^\beta$t$^\alpha$c$^\alpha$at$^\alpha$c$^\alpha$a$^\beta$Gt$^\alpha$-3' | 16 |
| 4 | BSI-5 | 5'-g$^\alpha$g$^\alpha$c$^\alpha$a$^\alpha$t$^\beta$Gt$^\beta$t$^\beta$c$^\alpha$a$^\alpha$t$^\beta$c$^\alpha$At$^\beta$c$^\alpha$a$^\alpha$g$^\alpha$t$^\beta$a$^\alpha$A-3' | 20 |
| 5 | BSI-6 | 5'-g$^\beta$g$^\beta$c$^\alpha$a$^\beta$t$^\beta$Gt$^\beta$t$^\beta$c$^\alpha$a$^\beta$t$^\beta$c$^\alpha$At$^\beta$c$^\alpha$a$^\beta$g$^\beta$t$^\beta$a$^\beta$A-3' | 20 |
| 6 | BSI-11 | 5'-g$^\alpha$g$^\alpha$c$^\alpha$a$^\alpha$t$^\alpha$Gt$^\alpha$t$^\alpha$c$^\alpha$a$^\alpha$t$^\alpha$c$^\alpha$At$^\alpha$c$^\alpha$a$^\alpha$g$^\alpha$t$^\alpha$a$^\alpha$A-3' | 20 |
| 7 | BSI-12 | 5'-g$^\beta$g$^\beta$c$^\beta$a$^\beta$t$^\beta$Gt$^\beta$t$^\beta$c$^\beta$a$^\beta$t$^\beta$c$^\beta$At$^\beta$c$^\beta$a$^\beta$g$^\beta$t$^\beta$a$^\beta$A-3' | 20 |
| 8 | BSI-18 | 5'-ggc$^\alpha$at$^\alpha$Gt$^\alpha$t$^\alpha$c$^\alpha$at$^\alpha$c$^\alpha$At$^\alpha$c$^\alpha$agt$^\alpha$aA-3' | 20 |
| 9 | BSI-19 | 5'-ggc$^\beta$at$^\beta$Gt$^\beta$t$^\beta$c$^\beta$at$^\beta$c$^\beta$At$^\beta$c$^\beta$agt$^\beta$aA-3' | 20 |
| 10 | BSI-21 | 5'-a$^\beta$c$^\alpha$Ga$^\beta$t$^\beta$a$^\beta$c$^\alpha$Gg$^\beta$Gt$^\beta$t$^\beta$a$^\beta$c$^\alpha$t$^\beta$-3' | 15 |
| 11 | BSI-22 | 5'-c$^\alpha$g$^\alpha$t$^\beta$g$^\alpha$a$^\beta$Gc$^\alpha$a$^\alpha$t$^\beta$c$^\alpha$Ct$^\beta$c$^\alpha$t$^\beta$c$^\alpha$t$^\beta$c$^\alpha$Gt$^\beta$t$^\alpha$-3' | 20 |

A, C, G, T = DNA-A, C, G, T
a, c, g, t = PNA-A, C, G, T
a, c, g, t = LNA-A, $^m$C, G, T
c$^\alpha$, t$^\alpha$ = 2',4'-BNA$^{NC}$[N-(CH$_2$)$_3$NH$_2$]-$^m$C, T
a$^\beta$, c$^\beta$, t$^\beta$ = 2',4'-BNA$^{NC}$[N-(CH$_2$)$_3$NMe$_2$]-A, $^m$C, T
a$^\alpha$, c$^\alpha$, g$^\alpha$, t$^\alpha$ = 2',4'-BNA$^{NC}$[N-H]-A, $^m$C, G, T
a$^\beta$, c$^\beta$, g$^\beta$, t$^\beta$ = 2',4'-BNA$^{NC}$[N-Me]-A, $^m$C, G, T Each of LSI-1 and BSI-5, 6, 11, 12, 18 and 19 had the sequence represented by SEQ ID NO: 13, BSI-4 had the sequence represented by SEQ ID NO: 14, BSI-21 had the sequence represented by SEQ ID NO: 25, and BSI-22 had the sequence represented by SEQ ID NO: 26.

2) Target Double-Stranded DNA [in Accordance with Chem. Commun., 2009, 1225-1227]

Target double-stranded DNA molecules are as follows.

(DNA-1) A 203-bp PCR product produced using pBR322 plasmid (commercially available product) as a template (SEQ ID NOs: 23 and 24).

(DNA-2) A 203-bp PCR product produced using artificial gene T1825G (commercially available product) based on pBR322 plasmid as a template.

(DNA-3) A 203-bp PCR product produced using artificial gene T1825C (commercially available product) based on pBR322 plasmid as a template.

(DNA-4) A 203-bp PCR product produced using artificial gene T1825A (commercially available product) based on pBR322 plasmid as a template.

[TABLE 11]

| No. | Name of target double-stranded DNA | Mutant type | Size (bp) | Sequences for target site (the position indicated by ↓ is mutating site) |
|---|---|---|---|---|
| 1 | DNA-1 | Wild-type | 203 | ↓<br>5'------GGCATGTTCATCATCAGTAA-----3'<br>3'------CCGTACAAGTAGTAGTCATT-----5' |
| 2 | DNA-2 | T1825G | 203 | ↓<br>5'------GGCATGTTCAGCATCAGTAA-----3'<br>3'------CCGTACAAGTCGTAGTCATT-----5' |
| 3 | DNA-3 | T1825C | 203 | ↓<br>5'------GGCATGTTCACCATCAGTAA-----3'<br>3'------CCGTACAAGTGGTAGTCATT-----5' |
| 4 | DNA-9 | T1825A | 203 | ↓<br>5'------GGCATGTTCAACATCAGTAA-----3'<br>3'------CCGTACAAGTTGTAGTCATT-----5' |

The sequences for a target site in DNA-1 are the sequences represented by SEQ ID NOs:15 and 16, the sequences for a target site in DNA-2 are the sequences represented by SEQ ID NOs: 17 and 18, the sequences for a target site in DNA-3 are the sequences represented by SEQ ID NOs:19 and 20, and the sequences for a target site in DNA-4 are the sequences represented by SEQ ID NOs: 21 and 22.

3) Method in Accordance with Chem. Commun., 2009, 1225-1227

(1) Preparation of Sample Solutions

Sample solutions each having the composition shown in the table below were prepared.

TABLE 12

| Reagent | Final concentration | Ratio |
|---|---|---|
| HEPES pH 7.0 (Buffer solution) | 5 mM | |
| NaCl | 20 mM | |
| SSB (Single-Stranded DNA Binding Protein) | 6 μM | 200 |
| Target double-stranded DNA (DNA-1) | 30 nM | 1 |
| Oligonucleotide for strand invasion (PNA20, BSI-4~6) | 200 nM | 6.7 |

(2) Reaction

Each of the sample solutions was reacted at 37° C. for 120 minutes, 60 minutes, or 30 minutes using a thermal cycler (StepOnePlus, Applied Biosystems).

(3) Gel Shift Assay and Staining

After the completion of the reaction, two gels respectively having the sample solutions applied thereon prepared, and PAGE (Poly-Acrylamide Gel Electrophoresis) was carried out on the gels simultaneously under the following conditions. Electrophoresis device: pageRun AE-6531 (ATTO Corporation) was used, and the conditions for electrophoresis were as directed in the instructions appended to the device.

(Conditions)
Gel: 15% polyacrylamide gel
Running buffer: tris-glycine buffer
(25 mM tris, 0.192 M glycine, pH 8.4, for Davis method)
Amount of sample applied: 12 μL (sample 10 μL+loading buffer 2 μL)

After the completion of the electrophoresis, one of the gel was subjected to fluorescence staining (GelGreen Nucleic Acid Stain 10,000×, Biotium) for staining a nucleic acid, and the other gel was subjected to silver staining (EzStain Silver, ATTO corporation) for staining a nucleic acid and a protein simultaneously. The staining methods were carried out following the appended instructions.

(4) Results

The results are shown in FIGS. 4A and 4B and FIGS. 5A and 5B.

In the presence of a single-stranded DNA binding protein (SSB), the occurrence of strand invasion of a PNA oligonucleotide against target double-stranded DNA was observed. That is, the results were reproduced under the literature conditions.

With respect to BSI-4 to 6 which correspond to the oligonucleotide (4) according to the present invention, as in the case of the PNA oligonucleotides, the occurrence of strand invasion was observed in the presence of a SSB.

4) Strand Invasion by Oligonucleotides in the Absence of SSB (1) Preparation of Sample Solutions Sample solutions each having the composition shown in the table below were prepared.

TABLE 13

| Reagent | Final concentration | Ratio |
|---|---|---|
| HEPES pH 7.0 (Buffer solution) | 5 mM | |
| NaCl | 20 mM | |
| Target double-stranded DNA (DNA-1) | 30 nM | 1 |
| Oligonucleotide for strand invasion (PNA20, BSI-5, 6) | 100 nM | 3.3 |

(2) Reaction

The reaction was carried out using a thermal cycler (StepOnePlus, Applied Biosystems), in which each of the sample solutions was cooled from 94° C. to 54° C. at a cooling rate of 2° C./30 seconds or was kept at 37° C. for a certain period (24 hours, 48 hours).

The condition that the sample solution was cooled from 94° C. to 54° C. at a cooling rate of 2° C./30 seconds was a condition where a target double-stranded DNA (in this case, a 203-bp PCR product) can be converted to a single strand by the action of a heat energy and strand invasion can be caused by cooling slowly. Therefore, the condition simulated the use in a gene analysis technique.

The condition that temperature is kept at 37° C. for a certain period simulated an in vivo reaction, and therefore simulated the use in a nucleic acid medicine or genome edition.

(3) Gel Shift Assay and Staining

The same procedures as in the step (3) above were carried out. In this experiment, only the staining using GelGreen (fluorescence staining) was carried out.

(4) Results

The results are shown in FIGS. 6A-6C.

With respect to BSI-5 and 6 which corresponded to the oligonucleotide (4) according to the present invention, even when the used amount was reduced to half of the amount of (3) (i.e., 3.3 equivalents relative to the amount of target dsDNA), the occurrence of strand invasion was confirmed under the condition where the specimen was cooled from 94° C. to 54° C. or the condition where the specimen was allowed to leave at 37° C. In contrast, with respect to the PNA oligonucleotide, the occurrence of strand invasion was not confirmed under this condition.

5) Strand Invasion Nucleotide Recognition Capability of Oligonucleotide in Single-Nucleotide Mismatch Sequence (1) Preparation of sample solutions Sample solutions each having the composition shown in the table below were prepared.

TABLE 14

| Reagent | Final concentration | Ratio |
| --- | --- | --- |
| HEPES pH 7.0 (Buffer solution) | 5 mM | |
| NaCl | 20 mM | |
| Target double-stranded DNA (DNA-1~4) | 15 nM | 1 |
| Oligonucleotide for strand invasion (PNA20, BSI-5, 6) | 200 nM | 13.3 |

(2) Reaction

The reaction was carried out using a thermal cycler (StepOnePlus, Applied Biosystems), in which each of the sample solutions was cooled from 94° C. to 54° C. at a cooling rate of 2° C./30 seconds or was kept at 37° C. for a certain period (24 hours, 48 hours).

(3) Gel Shift Assay and Staining

The same procedures as in the step (3) above were carried out. In this experiment, only the staining using GelGreen (fluorescence staining) was carried out.

(4) Results

The results are shown in FIGS. 7A-7L.

The occurrence of strand invasion into the sequence for wild-type of each of BSI-5 and 6 was observed. In contrast, the occurrence of strand invasion into a single-nucleotide mismatch sequence was not observed. That is, it was demonstrated that the oligonucleotides for strand invasion which had been prepared using the oligonucleotides (4) of the present invention had high sequence specificity.

In this regard, the PNA oligonucleotide did not cause strand invasion into the wild-type sequence under this condition.

6) Comparison of Strand Invasion Functionality of Oligonucleotides (1) Preparation of Sample Solutions Sample solutions each having the composition shown in the table below were prepared.

TABLE 15

| Reagent | Final concentration | Ratio |
| --- | --- | --- |
| HEPES pH 7.0 (Buffer solution) | 5 mM | |
| NaCl | 20 mM | |
| Target double-stranded DNA (DNA-1) | 30 nM | 1 |
| Oligonucleotide for strand invasion (PNA20, LSI-1, BSI-5, 6, 11, 12) | 100 nM | 3.3 |

(2) Reaction

The reaction was carried out using a thermal cycler (StepOnePlus, Applied Biosystems), in which each of the sample solutions was cooled from 94° C. to 54° C. at a cooling rate of 2° C./30 seconds or was kept at 37° C. for a certain period (24 hours, 48 hours).

(3) Gel Shift Assay and Staining

The same procedures as in the step (3) above were carried out. In this experiment, only the staining using GelGreen (fluorescence staining) was carried out.

(4) Results

The results are shown in FIGS. 8A-8C.

With respect to PNA20 and LSI-1, the occurrence of strand invasion was not observed under all of these conditions. With respect to BSI-11 and 12 which had been prepared using the oligonucleotides according to the prior art inventions, the occurrence of strand invasion of BSI-11 was observed although the degree of strand invasion was smaller than those observed in BSI-5 and 6, while the occurrence of strand invasion of BSI-12 was not observed.

With respect to BSI-5 and 6 which correspond to the oligonucleotide (4) according to the present invention, the occurrence of strand invasion was observed even after the lapse of 2 hours while keeping at 37° C.

That is, BSI-5 and 6 which correspond to the oligonucleotide (4) according to the present invention had most superior strand invasion capability.

7) Strand Invasion of Oligonucleotides BSI-18 and 19 Respectively Having Structure Such that LNA was Used as One or Some Bases in BSI-5 and 6

(1) Preparation of Sample Solutions

Sample solutions each having the composition shown in the table below were prepared.

TABLE 16

| Reagent | Final concentration | Ratio |
| --- | --- | --- |
| HEPES pH 7.0 (Buffer solution) | 5 mM | |
| NaCl | 20 mM | |
| Target double-stranded DNA (DNA-1) | 30 nM | 1 |
| Oligonucleotide for strand invasion (PNA20, LSI-1, BSI-5, 6, 18, 19) | 200 nM | 6.7 |

(2) Reaction

The reaction was carried out using a thermal cycler (StepOnePlus, Applied Biosystems), in which each of the sample solutions was cooled from 94° C. to 54° C. at a cooling rate of 2° C./30 seconds or was kept at 37° C. for a certain period (24 hours, 48 hours).

(3) Gel Shift Assay and Staining

The same procedures as in the step (3) above were carried out. In this experiment, only the staining using GelGreen (fluorescence staining) was carried out.

(4) Results

The results are shown in FIGS. 9A-9C.

In the oligonucleotides BSI-18 and 19 in each of which LNA was used as one or some bases, the occurrence of strand invasion was observed.

8) Strand Invasion Using Two or More Oligonucleotides (1) Preparation of Sample Solutions Sample solutions each having the composition shown in the table below were prepared.

TABLE 17

| Reagent | | Sample solution | | | | | | | | | |
|---|---|---|---|---|---|---|---|---|---|---|---|
| | | A | | B | | C | | D | | E | |
| | | Final concentration | Ratio | Final concentration | Ratio | Final concentration | Ratio | Final concentration | Ratio | Final concentration | Ratio |
| HEPES pH 7.0 (Buffer solution) | | 5 mM | — | 5 mM | — | 5 mM | — | 5 mM | — | 5 mM | — |
| NaCl | | 20 mM | — | 20 mM | — | 20 mM | — | 20 mM | — | 20 mM | — |
| Target double-stranded DNA (DNA-1) | | 30 nM | 1 | 30 nM | 1 | 30 nM | 1 | 30 nM | 1 | 30 nM | 1 |
| Oligonucleotide for strand invasion | BSI-22 | — | — | 1000 nM | 33 | 1000 nM | 33 | 1000 nM | 33 | 1000 nM | 33 |
| | BSI-5 | — | — | — | — | 1000 nM | 33 | — | — | 1000 nM | 33 |
| | BSI-21 | — | — | — | — | — | — | 1000 nM | 33 | 1000 nM | 33 |

(2) Reaction

The reaction was carried out using a thermal cycler (StepOnePlus, Applied Biosystems), in which each of the sample solutions was cooled from 94° C. to 54° C. at a cooling rate of 2° C./30 seconds.

(3) Gel Shift Assay and Staining

The same procedures as in the step (3) above were carried out. In this experiment, only the staining using GelGreen (fluorescence staining) was carried out.

(4) Results

The results are shown in FIG. 10.

When BSI-22 was used alone, a different band pattern was observed compared with a negative control, and it was also observed that a part of the band of the template DNA (DNA-1) was still left. From these results, it was suggested that strand invasion occurred even when BSI-22 was used alone. When BSI-22 and BSI-5 (which could hybridize with the same strand=cis type) were used in combination, or when BSI-22 and BSI-21 (which could hybridize with different strands from each other=trans type) were used in combination, a different band pattern was observed compared with the negative control, and the band of the template DNA was not observed. Therefore, it was confirmed that strand invasion occurred more efficiently. When BSI-22, BSI-21 and BSI-5 were used in combination, it was demonstrated that strand invasion was enhanced.

Sequence Listing

---

What is claimed is:

1. A compound represented by formula (1) or a salt thereof:

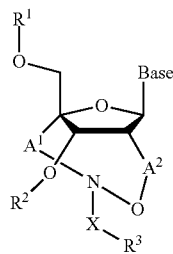

(1)

wherein

Base represents an aromatic heterocyclic group which may have a substituent or an aromatic hydrocarbon ring group which may have a substituent;

$A^1$ represents a linear alkylene group;

$A^2$ represents a single bond or an alkylene group;

X represents an alkylene group which may have a substituent or an alkylene group in which at least one methylene group moiety is substituted by —N($R^X$)— wherein $R^X$ represents a hydrogen atom or an alkyl) group, —O— or —S(=O)$_k$— wherein k represents 0, 1, or 2;

$R^1$ and $R^2$ are the same as or different from each other and independently represent a hydrogen atom, an alkyl group which may have a substituent, an alkenyl group which may have a substituent, a cycloalkyl group which may have a substituent, an aryl group which may have a substituent, a protecting group for a hydroxyl group, a phosphino group which has a substituent, a dihydroxyphosphinyl group which may have a substituent, or a hydroxymercaptophosphinyl group which may have a substituent, or $R^1$, $R^2$, two oxygen atoms respectively adjacent to $R^1$ and $R^2$ and carbon atoms at position-3 and position-5 in a furanose together form a ring which may have a substituent; and $R^3$ represents an amino group which may have a substituent.

2. The compound or the salt thereof according to claim 1, wherein $A^1$ represents a methylene group and $A^2$ represents a single bond.

3. The compound or the salt thereof according to claim 1, wherein X represents —$C_nH_{2n}$— wherein n represents an integer of 1 to 10.

4. The compound or the salt thereof according to claim 1, wherein $R^3$ represents a group represented by formula (A):

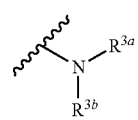

(A)

wherein $R^{3a}$ and $R^{3b}$ are the same as or different from each other and independently represent a hydrogen atom, an alkyl group which may have a substituent, an alkenyl group which may have a substituent, a cycloalkyl group which may have a substituent, a cycloalkenyl group which may have a substituent, an aryl group which may have a substituent, or a protecting group for an amino group, or $R^{3a}$, $R^{3b}$ and an adjacent nitrogen atom together form a ring which may have a substituent, or a group represented by formula (B):

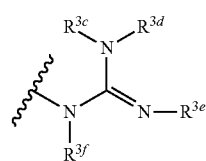

(B)

wherein $R^{3c}$ to $R^{3f}$ are the same as or different from each other and independently represent a hydrogen atom, an alkyl group, or a protecting group for an amino group.

5. The compound or the salt thereof according to claim 4, wherein, in formula (A), $R^{3a}$ and $R^{3b}$ are the same as or different from each other and independently represent a hydrogen atom, an alkyl group, an aryl group, an aralkyl group, or a protecting group for an amino group, or $R^{3a}$, $R^{3b}$ and an adjacent nitrogen atom together form a 5- to 10-membered nitrogenated aliphatic heterocyclic ring which may have an alkyl group as a substituent, and, in formula (B), $R^{3c}$ to $R^{3f}$ are the same as or different from each other and independently represent a hydrogen atom, or a protecting group for an amino group.

6. The compound or the salt thereof according to claim 1, wherein $R^1$ and $R^2$ are the same as or different from each other and independently represent a hydrogen atom, an alkyl group which may have an alkoxy group as an substituent, an aryl group which may have an alkoxy group as a substituent, an aralkyl group which may have an alkoxy group as a substituent, an alkylcarbonyl group, an arylcarbonyl group, an alkylsulfonyl group, an arylsulfonyl group, a group represented by the formula: —Si($R^4$)$_3$ wherein $R^4$s are the same as or different from each other and independently represent an alkyl group or an aryl group, a group represented by the formula: —P($R^5$)($R^6$) wherein $R^5$ and $R^6$ are the same as or different from each other and independently represent a hydroxyl group, a mercapto group, an amino group, an alkoxy group, a haloalkoxy group, a cyanoalkoxy group, an alkylthio group, a haloalkylthio group, a cyanoalkylthio group, or an alkylamino group, a dihydroxyphosphinyl group, or a hydroxymercaptophosphinyl group, or $R^1$, $R^2$, two oxygen atoms respectively adjacent to $R^1$ and $R^2$ and carbon atoms at position-3 and position-5 in a furanose together form a 6- to 10-membered aliphatic heterocyclic ring which may have an alkyl group as a substituent.

7. The compound or the salt thereof according to claim 1, wherein Base represents a 2,4-dioxo-1,2,3,4-tetrahydropyrimidin-1-yl group which may have a substituent, a 2-oxo-1,2-dihydropyrimidin-1-yl group which may have a substituent, a purin-9-yl group which may have a substituent, or a 6-oxo-1,6-dihydro-9H-purin-9-yl group which may have a substituent.

8. The compound or the salt thereof according to claim 1, wherein the compound is represented by any one of formulae (1A) to (1C):

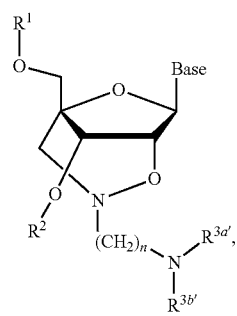

(1A)

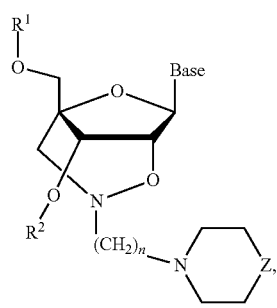

(1B)

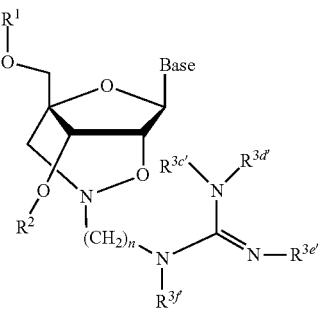

(1C)

wherein:

$R^{3a'}$ and $R^{3b'}$ are the same as or different from each other and independently represent a hydrogen atom, an alkyl group or a protecting group for an amino group;

Z represents a single bond, an oxygen atom, S(=O)$_m$ wherein m represents 0, 1, or 2, C ($R^{13}$)($R^{14}$) wherein $R^{13}$ and $R^{14}$ are the same as or different from each other and independently represent a hydrogen atom or an alkyl group, or NR$^{15}$ wherein $R^{15}$ represents a hydrogen atom, an alkyl group, or a protecting group for an amino group; and $R^{3e'}$ to $R^{3f'}$ are the same as or different from each other and independently represent a hydrogen atom, or a protecting group for an amino group.

9. A method for producing the compound represented by formula (1) or the salt thereof according to claim 1, the method comprising:

(I) reacting a compound represented by formula (2A):

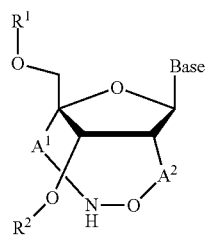

(2A)

with a compound represented by formula (3A): L¹-X—R³
wherein L¹ represents a leaving group; or (II) reacting a compound represented by formula (2B):

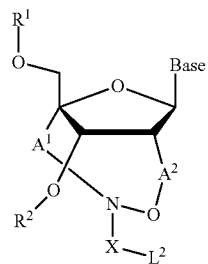

(2B)

wherein L² represents a leaving group
with a compound represented by formula (3B): R³—H.

10. D): A method for producing the compound represented by formula (1) or the salt thereof according to claim 1, wherein R³ represents an amino group which may be protected by a protecting group for an amino group, the method comprising:

(IIIa) reacting a compound represented by formula (2B):

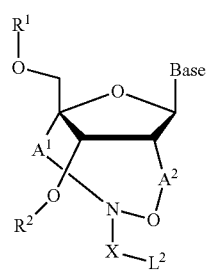

(2B)

wherein L² represents a leaving group with an azide salt to produce a compound represented by formula (1J):

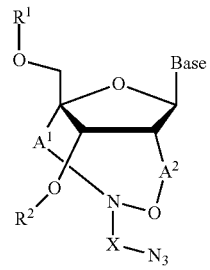

(1J)

(IIIb) reacting the compound represented by formula (1J) with a compound represented by formula (3C):

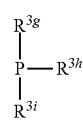

(3C)

wherein $R^{3g}$ to $R^{3i}$ are the same as or different from each other and independently represent an alkyl group or an aryl group,
and then hydrolyzing the resultant product to produce a compound represented by formula (1L):

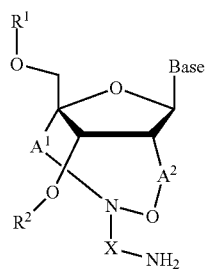

(1L)

(IIIc) optionally protecting an amino group in the compound represented by formula (1L).

11. D): A method for producing the compound represented by formula (1) or the salt thereof according to claim 1, wherein R³ represents a group represented by formula (B):

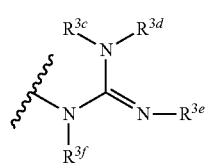

(B)

wherein $R^{3c}$ to $R^{3f}$ are the same as or different from each other and independently represent a hydrogen atom, an alkyl group, or a protecting group for an amino group, the method comprising guanidinylating a compound represented by formula (1) as recited in claim 1 or a salt thereof wherein R³ represents an amino group.

12. A method for producing the compound represented by formula (1) or the salt thereof according to claim 1, wherein Base represents formula (1K') or (1Q'):

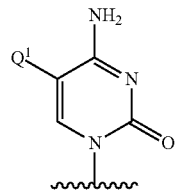
(1K')

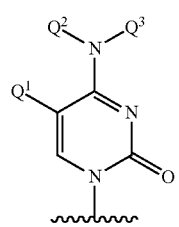
(1Q')

wherein $Q^1$ represents a hydrogen atom or a substituent; and $Q^2$ and $Q^3$ are the same as or different from each other and independently represent a hydrogen atom or a protecting group for an amino group provided that a case where each of $Q^2$ and $Q^3$ represents a hydrogen atom is excluded, the method comprising (VIb) reacting a compound represented by formula (1) as recited in claim 1 or a salt thereof wherein Base represents formula (1P'):

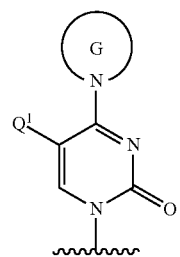
(1P')

wherein the ring G represents a 5- or 6-membered nitrogenated heterocyclic ring; and $Q^1$ is as defined above with ammonia.

13. The method according to claim 12, the method further comprises (VIc) protecting a compound produced by the reaction in the step (VIb) by a protecting group for an amino group.

14. A method for producing the compound represented by formula (1) or the salt thereof according to claim 1, wherein Base represents formula (1R') or (1S'):

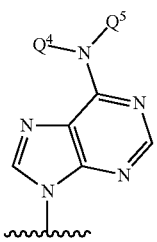
(1R')

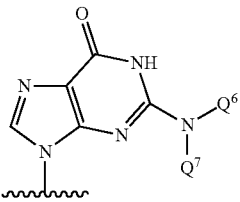
(1S')

wherein $Q^4$ to $Q^7$ are the same as or different from each other and independently represent a hydrogen atom or a protecting group for an amino group, the method comprising reacting the compound represented by formula (1) according to claim 1, wherein Base represents formula (1O'):

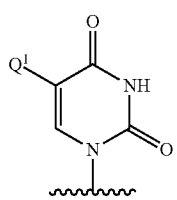
(1O')

wherein $Q^1$ represents a hydrogen atom or a substituent or a salt thereof with a compound represented by formula (3E) or (3F):

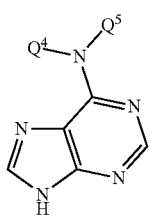
(3E)

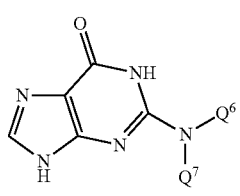
(3F)

wherein $Q^4$ to $Q^7$ are as defined above.

* * * * *